(12) United States Patent
Blake et al.

(10) Patent No.: US 9,315,831 B2
(45) Date of Patent: Apr. 19, 2016

(54) DIRECT STARCH TO FERMENTABLE SUGAR AS FEEDSTOCK FOR THE PRODUCTION OF ISOPRENE, ISOPRENOID PRECURSOR MOLECULES, AND/OR ISOPRENOIDS

(71) Applicants: Danisco US Inc., Palo Alto, CA (US); The Goodyear Tire & Rubber Company, Akron, OH (US)

(72) Inventors: Collette M. Blake, North Liberty, IA (US); Gopal K. Chotani, Cupertino, CA (US); Gang Duan, Shanghai (CN); Douglas Ko, Milpitas, CA (US); Floor Kooy, Leiden (NL); Sung Ho Lee, North Liberty, IA (US); Michael J. Pepsin, Castro Valley, CA (US); Ying Qian, Wuxi (CN); Matt Reboli, Palo Alto, CA (US); Vivek Sharma, North Liberty, IA (US); Jayarama K. Shetty, Pleasanton, CA (US); Bruce A. Strohm, Beloit, WI (US); Pauline Johanna Maria Teunissen, Saratoga, CA (US); Hongxian Xu, Wuxi (CN)

(73) Assignees: DANISCO US INC., Palo Alto, CA (US); THE GOODYEAR TIRE & RUBBER COMPANY, Akron, OH (US)

( * ) Notice: Subject to any disclaimer, the term of this patent is extended or adjusted under 35 U.S.C. 154(b) by 0 days.

(21) Appl. No.: 13/802,420

(22) Filed: Mar. 13, 2013

(65) Prior Publication Data

US 2013/0280774 A1 Oct. 24, 2013

Related U.S. Application Data

(60) Provisional application No. 61/618,556, filed on Mar. 30, 2012.

(51) Int. Cl.
*C12P 5/02* (2006.01)
*C12P 5/00* (2006.01)
(Continued)

(52) U.S. Cl.
CPC . *C12P 5/007* (2013.01); *C12N 9/88* (2013.01); *C12P 7/42* (2013.01); *C12P 7/46* (2013.01);
(Continued)

(58) Field of Classification Search
None
See application file for complete search history.

(56) References Cited

U.S. PATENT DOCUMENTS 4,318,927 A 3/1982 Marshall
RE32,153 E 5/1986 Tamura et al.
(Continued)

FOREIGN PATENT DOCUMENTS

JP 2008-61506 A 3/2008
WO WO-92/00381 A1 1/1992
(Continued)

OTHER PUBLICATIONS

Alexander, "Corn Dry Milling: Processes, Products, and Applications,"Chaper II in *Corn: Chemistry and Technology*, (Watson & Ramstead eds., American Association of Cereal Chemists, Inc., 1987, pp. 351-376.
(Continued)

*Primary Examiner* — Robert Mondesi
*Assistant Examiner* — Richard Ekstrom
(74) *Attorney, Agent, or Firm* — Mintz, Levin, Cohn, Ferris, Glovsky and Popeo, P.C.

(57) ABSTRACT

Provided herein are compositions and methods related to the direct conversion of the starch in a ground or fractionated grain into a fermentable sugar feedstock capable of serving as a carbon source for the industrial production of one or more products by a fermenting organism, such as isoprene, isoprenoid precursor molecules, and/or isoprenoids. Such conversions may be performed at temperatures at or below the initial gelatinization temperature of the starch present in the grain and may utilize one or more isolatable endogenous enzymes present in certain unrefined grains.

43 Claims, 9 Drawing Sheets

(51) Int. Cl.
*C12N 9/88* (2006.01)
*C12P 7/42* (2006.01)
*C12P 7/46* (2006.01)
*C12P 7/56* (2006.01)
*C12P 19/02* (2006.01)
*C12P 19/14* (2006.01)

(52) U.S. Cl.
CPC .................. *C12P 7/56* (2013.01); *C12Y 301/03* (2013.01); *C12P 19/02* (2013.01); *C12P 19/14* (2013.01); *Y02P 20/52* (2015.11)

(56) References Cited

U.S. PATENT DOCUMENTS

| | | | |
|---|---|---|---|
| 4,587,215 | A | 5/1986 | Hirsh |
| 4,618,579 | A | 10/1986 | Dwiggins et al. |
| 5,322,778 | A | 6/1994 | Antrim et al. |
| 5,756,714 | A * | 5/1998 | Antrim et al. ............... 536/102 |
| 5,763,385 | A | 6/1998 | Bott et al. |
| 5,824,532 | A | 10/1998 | Barnett et al. |
| 5,958,739 | A | 9/1999 | Mitchinson et al. |
| 6,008,026 | A | 12/1999 | Day |
| 6,361,809 | B1 | 3/2002 | Christophersen et al. |
| 6,566,125 | B2 | 5/2003 | Johnston et al. |
| 6,740,740 | B2 | 5/2004 | Garger et al. |
| 6,899,910 | B2 | 5/2005 | Johnston et al. |
| 7,037,704 | B2 | 5/2006 | Dunn-Coleman et al. |
| 7,303,899 | B2 | 12/2007 | Baldwin et al. |
| 7,618,795 | B2 * | 11/2009 | Vikso-Nielsen et al. ....... 435/41 |
| 7,659,097 | B2 * | 2/2010 | Renninger et al. ............ 435/157 |
| 7,915,026 | B2 | 3/2011 | Keasling et al. |
| 2003/0134395 | A1 * | 7/2003 | Shetty et al. .................. 435/96 |
| 2003/0180900 | A1 | 9/2003 | Lantero |
| 2004/0234649 | A1 | 11/2004 | Lewis et al. |
| 2006/0121589 | A1 | 6/2006 | Dunn-Coleman et al. |
| 2008/0199918 | A1 * | 8/2008 | Viksoe-Nielsen et al. .... 435/101 |
| 2008/0201807 | A1 | 8/2008 | Henry et al. |
| 2008/0299622 | A1 * | 12/2008 | Paulson et al. ................ 435/99 |
| 2008/0318284 | A1 * | 12/2008 | Soong et al. .................. 435/96 |
| 2009/0203102 | A1 | 8/2009 | Cervin et al. |
| 2009/0282545 | A1 | 11/2009 | Eichelberger et al. |
| 2009/0305360 | A1 | 12/2009 | Breneman et al. |
| 2009/0305935 | A1 | 12/2009 | Cascao-Pereira et al. |
| 2010/0003366 | A1 * | 1/2010 | Cuevas et al. .................. 426/20 |
| 2010/0003716 | A1 | 1/2010 | Cervin et al. |
| 2010/0048964 | A1 | 2/2010 | Calabria et al. |
| 2010/0055752 | A1 * | 3/2010 | Kumar .......................... 435/161 |
| 2010/0086978 | A1 | 4/2010 | Beck et al. |
| 2010/0167370 | A1 * | 7/2010 | Chotani et al. ................ 435/167 |
| 2010/0196977 | A1 | 8/2010 | Chotani et al. |
| 2010/0285549 | A1 | 11/2010 | Muramatsu et al. |
| 2010/0297749 | A1 | 11/2010 | Aravanis et al. |
| 2011/0045563 | A1 | 2/2011 | Melis |
| 2011/0178261 | A1 | 7/2011 | Feher et al. |

FOREIGN PATENT DOCUMENTS

| | | |
|---|---|---|
| WO | WO-99/28448 A1 | 6/1999 |
| WO | WO-00/04136 A1 | 1/2000 |
| WO | WO-2004/033646 A2 | 4/2004 |
| WO | WO-2004/033646 A3 | 4/2004 |
| WO | WO-2004/081193 A2 | 9/2004 |
| WO | WO-2004/081193 A3 | 9/2004 |
| WO | WO2009005704 A1 * | 1/2009 |
| WO | WO-2009/076676 A2 | 6/2009 |
| WO | WO-2009/076676 A3 | 6/2009 |
| WO | WO-2009/132220 A2 | 10/2009 |
| WO | WO-2009/132220 A3 | 10/2009 |
| WO | WO-2009/132220 A9 | 10/2009 |
| WO | WO-2009/134964 A2 | 11/2009 |
| WO | WO-2009/134964 A3 | 11/2009 |
| WO | WO-2010/003007 A2 | 1/2010 |
| WO | WO-2010/003007 A3 | 1/2010 |
| WO | WO-2010/013077 A1 | 3/2010 |
| WO | WO-2010/031062 A1 | 3/2010 |
| WO | WO-2010/031068 A1 | 3/2010 |
| WO | WO-2010/031076 A2 | 3/2010 |
| WO | WO-2010/031076 A3 | 3/2010 |
| WO | WO-2010/031079 A1 | 3/2010 |
| WO | WO-2010/078457 A2 | 7/2010 |
| WO | WO-2010/078457 A3 | 7/2010 |
| WO | WO-2010/124146 A2 | 10/2010 |
| WO | WO-2010/124146 A3 | 10/2010 |
| WO | WO-2010/148150 A1 | 12/2010 |
| WO | WO-2010/148256 A1 | 12/2010 |
| WO | WO-2011/034863 A1 | 3/2011 |
| WO | WO 2012/018775 A1 | 2/2012 |
| WO | WO-2012/019169 A1 | 2/2012 |

OTHER PUBLICATIONS

Belitz, et al., Food Chemistry, 3$^{rd}$ ed., *Springer*, 2004, p. 318-323.
Berka & Barnett, "The Development of Gene Expression Systems for Filamentous Fungi," *lotechnology Advances*, 1989, 7(2):127-154.
Bhayana, et al., "Amino Acid Sequence of *Escherichia coli* Citrate Synthase," *Biochemistry*, 1984, 23(13):2900-2905.
Boel, et al., "Two Different Types of Intervening Sequences in the Glucoamylase Gene from *Aspergillus niger*," *The EMBO Journal*, 1984, 3(7):1581-1585.
Bologna, et al., "*Escherichia coli* Malic Enzymes: Two Isoforms with Substantial Differences in Kinetic Properties, Metabolic Regulation, and Structure," *Journal of Bacteriology*, Aug. 2007, 189(16):5937-5946.
Bunch, et al., "The *IdhA* Gene Encoding the Fermentative Lactate Dehydrogenase of *Escherichia coli*," *Microbiology*, 1997, 143:187-195.
Campbell, et al., "Improved Transformation Efficiency of *Aspergillus niger* Using the Homologus niaD Gene for Nitrate Reductase," *Current Genetics*, 1989, 16:53-56.
Chen, et al., "Effect of Replacing Helical Glycine Residues With Alanines on Reversible and Irreversible Stability and Production of *Aspergillus awamori* Glucoamylase," *Prot. Eng.*, 1996, 9(6):499-505.
Danner, et al., "Four Terpene Synthases Produce Major Compounds of the Gypsy Moth Feeding-Induced Volatile Blend of *Populus Trichocarpa*," *Phytochemistry*, Jun. 2011, 72( 9):897-908.
Dawes, et al., "The Route to Ethanol Formation in *Zymomonas mobilis*," *Biochem. J.*, 1966, 98:795-803.
Duckworth, et al., "Structural Basis for Regulation in Gram-Negative Bacterial Citrate Synthases," *Biochem Soc Symp.*, 1987, 54:83-92.
Fowler, et. al, "Increased Malonyl Coenzyme A Biosynthesis by Tuning the *Escherichia coli* Metabolic Network and Its Application to Flavanone Production," *Applied and Environmental Microbiology*, 2009, 75(18):5831-5839.
Garms et al, "A Multiproduct Terpine Synthase from *Medicago truncatula* Generates Cadalane Sesquiterpenes via Two Different Mechanisms," *J Org Chem.*, Aug. 2010, 20;75(16):5590-5600.
GenBank Accession No. AB540131.1, last updated on Oct. 9, 2013, located at <http://www.ncbi.nlm.nih.gov/nuccore/299758081>, last visited on May 13, 2014, 2 pages.
GenBank Accession No. AJ457070, last updated on Apr. 15, 2005, located at <http://www.ncbi.nlm.nih.gov/nuccore/38092202>, last visited on Jun. 2, 2010, 2 pages.
GenBank Accession No. AY279379, last updated on Mar. 11, 2005, located at <http://www.ncbi.nlm.nih.gov/nuccore/30984014>, last visited on Jun. 2, 2010, 2 pages.
GenBank Accession No. AY316691, last updated on Feb. 15, 2005, located at <http://www.ncbi.nlm.nih.gov/nuccore/35187003>, last visited on Jun. 2, 2010, 2 pages.
GenBank Accession No. CAC35696, last updated Apr. 15, 2005, located at <http://www.ncbi.nlm.nih.gov/protein/CAC35696>, last visited on May 13, 2014, 2 pages.
GenBank Accession No. JN173042, created Jan. 19, 2012, last updated on Apr. 17, 2013, located at http://www.ebi.ac.uk/ena/data/view/JN173042&display=text, last visited on May 13, 2014, 2 pages.
GenBank Accession No. NC_001416, last updated on Mar. 11, 2011, located at http://www.ncbi.nlm.nih.gov/nuccore/9626243?report=genbank, last visited on May 13, 2014, 42 pages.

(56) References Cited

OTHER PUBLICATIONS

Gorinstein & Lii, "The Effects of Enzyme Hydrolysis on the Properties of Potato, Cassava and Amaranth Starches," *Starch/Stärk*, 1992, 44(12):461-466.

Hedl, et al. "*Enterococcus faecalis* Acetoacetyl-Coenzyme a Thiolase/3-Hydroxy-3-Methyglutaryl-Coenzyme a Reductase, a Dual-Function Protein of Isopentenyl Diphosphate Biosynthesis," *Journal of Bacteriology*, Apr. 2002, 184(8):2116-2122.

Hsieh, et al., "Structure and Mechanism of an Arabidopsis Medium/Long-Chain-Length Prenyl Pyrophosphate Synthase," *Plant Physiology*, Mar. 2011, 155(3):1079-1090.

Iwakura, et al., Studies on Regulatory Functions of Malic Enzymes, *J. Biochem.*, 1979, 85:1355-1365.

Jensen, et al., "Purification of Extracellular Amylolytic Enzymes from the Thermophilic Fungus *Thermomyces lanuginosus*," *Can. J. Microbiol.*, 1988 34:218-223.

Jones, et al.,"Sandalwood Fragrance Biosynthesis Involves Sesquiterpene Synthases of Both the Terpene Synthase (TPS)-a and TPS-b Subfamilies, including Santalene Synthases," *J. Biol. Chem.* 2011 286: 17445-17454.

Kakuda, et al., "Identification and Characterization of the ackA (Acetate Kinase a)-*pta* (Phosphotransacetylase) Operon and Complementation Analysis of Acetate Utilization by an ackA-pta Deletion Mutant of *Escherichia coli*,". *J. Biochem.*, 1994, 116:916-922.

Keeling, et al., "Transcriptome Mining, Functional Characterization, and Phylogeny of a Large Terpene Synthase Gene Family in Spruce (*Picea* spp.)," *BMC Plant Biol.*, Mar. 2011, 11:43, 14 pages.

Kotlarz, et al., "Regulation of the Amount and of the Activity of Phosphofructokinases and Pyruvate Kinases in *Escherichia coli*," *Biochim. Biophys. Acta*, 1975, 381:257-268.

Kumeta et al. "Characterization of δ-Guaiene Synthases from Cultured Cells of *Aquilaria*, Responsible for the Formation of the Sesquiterpenes in Agarwood," *Plant Physiol.*, Dec. 2010;154(4):1998-2007.

Lindberg, et al., "Engineering a Platform for Photosynthetic Isoprene Production in Cyanobacteria, Using *Synechocystis* as the Model Organism," *Metab. Eng.*, 2010, 12(1):70-79.

Martin, et al., "Functional Annotation, Genome Organization and Phylogeny of the Grapevine (*Vitis vinifera*) Terpene Synthase Gene Family Based on Genome Assembly, FLcDNA Cloning, and Enzyme Assays," *BMC Plant Biol.*,Oct. 21, 2010;10:226, 22 pages.

Martin, et al., "Engineering a Mevalonate Pathway in *Escherichia coli* for Production of Terpenoids," *Nature Biotechnology*, Jul. 2003, 21(7):796-802.

Maurus, et al., "Insights into the Evolution of Allosteric Properties. The NADH Binding Site of Hexameric Type II Citrate Synthases," *Biochemistry*, 2003, 42(19):5555-5565.

Meile, et al., "Characterization of the D-Xylulose 5-Phosphate/D-Fructose 6-Phosphate Phosphoketolase Gene (*xfp*) from *Bifidobacterium Lactis*," *J. Bact.*, 2001, 183(9):2929-2936.

Miller, et al., "First Isolation of an Isoprene Synthase Gene from Poplar and Successful Expression of the Gene in *Escherichia coli*," *Planta*, (e-pub. May 10, 2001) 213:483-487.

Ner, et al., "Complete Sequence of the glt A Gene Encoding Citrate Synthase in *Escherichia coli*," *Biochemistry*, Nov. 8, 1983, 22(23):5243-5249.

Newman, et. al., "High-Level Production of Amorpha-4,11-Diene in a Two-Phase Partitioning Bioreactor of Metabolically Engineered *Escherichia coli*," *Biotechnol. Bioeng.*, 2006, 95:684-691.

Ogasawara, et al., PdhR (Pyruvate Dehydrogenase Complex Regulator) Controls the Respiratory Electron Transport System in *Escherichia coli, J. Bact.*, 2007, 189(15):5534-5541.

Oh, et al., "Global Expression Profiling of Acetate-Grown *Escherichia coli*," *The Journal of Biological Chemistry*, Apr. 12, 2002, 277(15):13175-13183.

Okamura, et al., "Unprecedented Acetoacetyl-coenzyme a Synthesizing Enzyme of the Thiolase Superfamily Involved in the Mevalonate Pathway," *PNAS*, Jun. 22, 2010, 107(25):11265-11270.

Peekhaus and Conway, "What's for Dinner?: Entner-Doudoroff Metabolism in *Escherichia coli*," *J. Bact.*, 1998, 180(14):3495-3502.

Quant, et al., Treatment of Rats With Glucagon or Mannoheptulose Increases Mitochondrial 3-Hydroxy-3-Methylglutaryl-CoA Synthase Activity and Decreases Succinyl-CoA Content in Liver, *Biochem J.*, 1989, 262:159-164.

Rao, et al., "Purification and Characterization of a Thermostable Glucoamylase from the Thermophilic Fungus. *Thermomyces lanuginosus*," *Biochem. J*, 1981, 193:379-387.

Romanos et al., "Foreign Gene Expression in Yeast: a Review," *Yeast*, 1992, 8(6):423-488.

Sanchez, et al., "Novel Pathway Engineering Design of the Anaerobic Central Metabolic Pathway in *Escherichia coli* to Increase Succinate Yield and Productivity," *Metab. Eng.*, 2005, 7:229-239.

Sharkey et al., "Evolution of the Isoprene Biosynthetic Pathway in Kudzu," *Plant Physiology*, 2005, 137:700-712.

Shetty, et al., "An Acid-stable, Thermostable Alpha-amylase for Starch Liquefaction,"*Cereal Foods World*, 1988, 33:929-934.

Shimizu, et al., "Phosphotransacetylase of *Escherichia coli* B, Purification and Properties," *Biochim. Biophys., Acta*, 1969, 191:550-558.

Silver, et al., "Characterization of Aspen Isoprene Synthase, an Enzyme Responsible for Leaf Isoprene Emission to the Atmosphere," *J. Biol. Chem.*, Jun. 2, 1995, 270(22):13010-13016.

Sprenger, Genetics of Pentose-Phosphate Pathway Enzymes of *Escherichia coli* K-12, *Arch. Microbiol.*, 1995, 164:324-330.

Stokell et al., "Probing the Roles of Key Residues in the Unique Regulatory NADH Binding Site of Type II Citrate Synthase of *Eschenschia coli*," *J. Biol. Chem.*, Sep. 12, 2003, 278: 35435-35443.

Stulke and Hillen, "Regulation of Carbon Catabolism in *Bacillus Species*," *Annu. Rev. Microbiol.*, 2000, 54:849-880.

Swinkels, "Sources of Starch, its Chemistry and Physics," in *Starch Conversion Technology*, Van Beynum et al., eds. Marcel Dekker Inc., New York, 1985, p. 15-46.

Taylor, et al., "Some Properties of a Glucoamylase Produced by the Thermophilic Fungus *Humicola lanuginose*," *Carbohydrate Res.*, 1978, 61:301-308.

Underwood, et al., Flux through Citrate Synthase Limits the Growth of Ethanologenic *Escherichia coli* KO11 during Xylose Fermentation, *Appl. Environ. Microbiol.*, Mar. 2002, 68(3):1071-1081.

White, "Fructose Syrup: Production, Properties, and Applications," Shenck and Hebeda, eds. (1992; VCH Publishers, Inc., New York), 1992, 177-199.

Wiegand, et al., "Citrate Synthase: Structure, Control, and Mechanism," *Annual Rev. Biophysics Biophys. Chem.*, 1986, 15:97-117.

Wolfe, "The Acetate Switch," *Microb. Mol. Biol. Rev.*, Mar. 2005, 69(1):12-50.

Wu, et al., "Factors Impacting Ethanol Production from Grain Shorghum in the Dry-Grind Process," *Cereal Chem.*, 2007, 84(2):130-136.

Zhang & Hamaker, "Low α-Amylase Starch Digestibility of Cooked Sorghum Flours and the Effect of Protein," *Cereal Chem.*, 1998, 75(5):710-713.

Actinobacillus succinogenes (strain ATCC 55618 / 130Z), located at http://hamap.expasy.org/proteomes/ACTSZ.html 7/, retrieved on Jul. 14, 2014, 1 page.

International Search Report and the Written Opinion of the International Searching Authority for International Application No. PCT/US2013/034684, dated Jul. 4, 2013.

\* cited by examiner

SEQUENCE LISTING

```
<160> NUMBER OF SEQ ID NOS: 2

<210> SEQ ID NO 1
<211> LENGTH: 329
<212> TYPE: PRT
<213> ORGANISM: Streptomyces sp. CL190

<400> SEQUENCE: 1

Met Thr Asp Val Arg Phe Arg Ile Ile Gly Thr Gly Ala Tyr Val Pro
1               5                   10                  15

Glu Arg Ile Val Ser Asn Asp Glu Val Gly Ala Pro Ala Gly Val Asp
            20                  25                  30

Asp Asp Trp Ile Thr Arg Lys Thr Gly Ile Arg Gln Arg Arg Trp Ala
        35                  40                  45

Ala Asp Asp Gln Ala Thr Ser Asp Leu Ala Thr Ala Ala Gly Arg Ala
    50                  55                  60

Ala Leu Lys Ala Ala Gly Ile Thr Pro Glu Gln Leu Thr Val Ile Ala
65                  70                  75                  80

Val Ala Thr Ser Thr Pro Asp Arg Pro Gln Pro Pro Thr Ala Ala Tyr
                85                  90                  95

Val Gln His His Leu Gly Ala Thr Gly Thr Ala Ala Phe Asp Val Asn
            100                 105                 110

Ala Val Cys Ser Gly Thr Val Phe Ala Leu Ser Ser Val Ala Gly Thr
        115                 120                 125

Leu Val Tyr Arg Gly Gly Tyr Ala Leu Val Ile Gly Ala Asp Leu Tyr
    130                 135                 140

Ser Arg Ile Leu Asn Pro Ala Asp Arg Lys Thr Val Val Leu Phe Gly
145                 150                 155                 160

Asp Gly Ala Gly Ala Met Val Leu Gly Pro Thr Ser Thr Gly Thr Gly
                165                 170                 175

Pro Ile Val Arg Arg Val Ala Leu His Thr Phe Gly Gly Leu Thr Asp
            180                 185                 190

Leu Ile Arg Val Pro Ala Gly Gly Ser Arg Gln Pro Leu Asp Thr Asp
        195                 200                 205

Gly Leu Asp Ala Gly Leu Gln Tyr Phe Ala Met Asp Gly Arg Glu Val
    210                 215                 220
```

-continued

```
Arg Arg Phe Val Thr Glu His Leu Pro Gln Leu Ile Lys Gly Phe Leu
225                 230                 235                 240

His Glu Ala Gly Val Asp Ala Ala Asp Ile Ser His Phe Val Pro His
                245                 250                 255

Gln Ala Asn Gly Val Met Leu Asp Glu Val Phe Gly Glu Leu His Leu
            260                 265                 270

Pro Arg Ala Thr Met His Arg Thr Val Glu Thr Tyr Gly Asn Thr Gly
        275                 280                 285

Ala Ala Ser Ile Pro Ile Thr Met Asp Ala Ala Val Arg Ala Gly Ser
    290                 295                 300

Phe Arg Pro Gly Glu Leu Val Leu Leu Ala Gly Phe Gly Gly Gly Met
305                 310                 315                 320

Ala Ala Ser Phe Ala Leu Ile Glu Trp
                325

<210> SEQ ID NO 2
<211> LENGTH: 125
<212> TYPE: DNA
<213> ORGANISM: Enterobacteria phage lambda

<400> SEQUENCE: 2
aattcatata aaaacatac agataaccat ctgcggtgat aaattatctc tggcggtgtt        60
gacataaata ccactggcgg tgatactgag cacatcagca ggacgcactg accaccatga     120
aggtg                                                                  125
```

DIRECT STARCH TO FERMENTABLE SUGAR AS FEEDSTOCK FOR THE PRODUCTION OF ISOPRENE, ISOPRENOID PRECURSOR MOLECULES, AND/OR ISOPRENOIDS

CROSS-REFERENCE TO RELATED APPLICATIONS

This application claims benefit to U.S. Provisional patent application 61/618,556 filed on Mar. 30, 2012, the contents of which are hereby incorporated by reference in its entirety.

INCORPORATION BY REFERENCE

The content of the following submission on ASCII text file is incorporated herein by reference in its entirety: a computer readable form (CRF) of the Sequence Listing (file name: 643842003900_Sequence_Listing.txt, date created: Jun. 6, 2013, size: 3,713 bytes).

FIELD OF THE INVENTION

This disclosure is directed towards compositions and methods related to the direct conversion of starch in a ground or fractionated grain into a fermentable sugar feedstock capable of serving as a carbon source for the industrial production of one or more products, such as isoprene, isoprenoid precursor molecules, and/or isoprenoids, by a fermenting organism.

BACKGROUND OF THE INVENTION

Isoprene (2-methyl-1,3-butadiene) is the critical starting material for a variety of synthetic polymers, most notably synthetic rubbers. Isoprene is naturally produced by a variety of microbial, plant, and animal species. In particular, two pathways have been identified for the biosynthesis of isoprene: the mevalonate (MVA) pathway and the non-mevalonate (DXP) pathway. However, the yield of isoprene from naturally-occurring organisms is commercially unattractive. Isoprene can also be obtained by fractionating petroleum, the purification of this material is expensive and time-consuming. Petroleum cracking of the C5 stream of hydrocarbons produces only about 15% isoprene. About 800,000 tons per year of cis-polyisoprene are produced from the polymerization of isoprene; most of this polyisoprene is used in the tire and rubber industry. Isoprene is also copolymerized for use as a synthetic elastomer in other products such as footwear, mechanical products, medical products, sporting goods, and latex.

Isoprenoids are compounds derived from the isoprenoid precursor molecules IPP and DMAPP. Over 29,000 isoprenoid compounds have been identified and new isoprenoids are being discovered each year. Isoprenoids can be isolated from natural products, such as microorganisms and species of plants that use isoprenoid precursor molecules as a basic building block to form the relatively complex structures of isoprenoids. Isoprenoids are vital to most living organisms and cells, providing a means to maintain cellular membrane fluidity and electron transport. In nature, isoprenoids function in roles as diverse as natural pesticides in plants to contributing to the scents associated with cinnamon, cloves, and ginger. Moreover, the pharmaceutical and chemical communities use isoprenoids as pharmaceuticals, nutraceuticals, flavoring agents, and agricultural pest control agents. Given their importance in biological systems and usefulness in a broad range of applications, isoprenoids have been the focus of much attention by scientists.

Methods for the production of isoprene, isoprenoid precursor molecules, and/or isoprenoids by recombinant cells at high rates, titers, and purities have been disclosed (see, for example, International Patent Application Publication No. WO 2009/076676 A2. However, industrial production of these molecules by engineered cells requires a fermentable feed stock carbon source, typically derived from an agriculturally-based starch, on which the cells can grow. A less expensive source of carbon used during the production process has the potential to lower the cost of industrial production for isoprene, isoprenoid precursor molecules, and/or isoprenoids.

A number of agricultural crops are viable candidates for the conversion of starch to fermentable feed stock. Such fermentable feedstocks can be fed to various microbes to produce a variety of biochemicals. Typically, corn is used as the primary starch source for producing fermentable glucose. However other high-starch content sources like sorghum, wheat, barley, rye and cassava are beginning to gain more attention as a viable feedstock for the industrial production of biochemicals and fuel. The conventional process for producing a fermentable high glucose syrup feedstock from insoluble starch involves heating whole ground grain or starch slurry to temperatures in excess of 95° C. in the presence of alpha amylase (a process known as "liquefaction"), followed by cooling, pH adjustment, and subsequent glucoamylase hydrolysis (otherwise known as "saccharification"). Such processes can produce fermentable feed stocks containing greater than 90% glucose. However, these conventional approaches are highly energy-intensive.

Various industrial processes have been adopted by the starch sweetener industry for enzyme-mediated liquefaction (see, e.g. U.S. Pat. No. 5,322,778). Some of these processes are performed at lower temperatures with relatively low steam requirements (e.g., 105-110° C. for 5-8 min) while others are high temperature processes (e.g., 148° C.+/−5° C. for 8-10 sec), resulting in improved gelatinization of starch granules leading to improved filtration characteristics and quality of the liquefied starch substrate (Shetty, et al., (1988) *Cereal Foods World* 33:929-934). Further advances in the liquefaction process have been demonstrated by multiple additions of thermostable alpha amylases in the pre/post jet cooking step, which results in significant improvements with respect to yield loss, processing costs, energy consumption, pH adjustments, temperature thresholds, calcium requirements and levels of retrograded starch.

The drastic conditions required for liquefaction (e.g. high temperature and pH), negatively affect the bioconversion efficiency of whole ground grains into feedstocks, resulting in the loss of fermentable sugars, production of Maillard reaction products, destruction of essential nutrients (e.g., free sugars, free amino acids, minerals, vitamins), deactivation of native beneficial enzymes (e.g. amylases, proteases, and phytases) and/or cross-linking or condensation of cellular components such as tannins and starch proteins (Wu et al., *Cereal Chem.,* 2007, 84:130-13). Furthermore, significant energy costs are associated with high-temperature cooking of grain to aid in enzymatic digestion. In addition, in the context of the dry grind process for ethanol, the incomplete gelatinization during high temperature cooking (i.e. temperatures exceeding the starch gelatinization temperature) for solubilizing granular starch in ground whole grain is believed to be the principle reason for lower digestibility by alpha amylases. The digestibility of starch is also negatively affected by starch-lipid and starch-protein complexes formed during the interaction of reactive proteins and lipids with starch at liquefaction conditions (Zhang & Hamaker, *Cereal Chem.*, 1998, 75:710-713). Another major problem associated with liquefaction at high temperature is high viscosity due to the rapid swelling of starch and non-starch polysaccharide components such as beta-glucan.

Due to increasing concern for the environment and the need to limit greenhouse gases, sources of renewable energy are gaining wide-spread attention. The recent development of no-cook processes using enzymes capable of hydrolyzing granular starch directly into fermentable glucose have made significant improvements in the energy required for ethanol production (see, e.g., U.S. Pat. No. 7,037,704; U.S. Patent Application Publication Nos.: 2003/0180900 A1, 2006/0121589 A1, and US 2004/0234649 A1; and International Patent Application Publication No.: 2004/081193 A2). However, these processes require extensive milling for fine grind particles, longer fermentation times, and potential risk of microbial infection.

Another major problem associated with current processes for the production of high fermentable glucose syrup (such as syrups with greater than 96% fermentable sugar) is loss of glucose yield due to the production of the reversion reaction product, isomaltose (6 O-α-D-glucopyranosyl-a [1-6]-α-D-Glucopyranoside). This reversion reaction can be catalyzed by glucoamylases during saccharification. Many microorganisms used for the production of valuable biochemicals cannot ferment isomaltose, and such approaches also result in downstream processing losses during recovery, and yield losses. What is needed, therefore, is a low temperature process for the direct production of fermentable feedstocks from ground or fractionated grain that avoids the drawbacks associated with currently available no-cook enzymatic starch hydrolysis processes which contains reduced amounts of reversion products and which can serve as a carbon source for the production of isoprene, isoprenoid precursor molecules, and/or isoprenoids.

The invention described herein addresses these problems and provides additional benefits as well.

All patents, patent applications, publications, documents, nucleotide and protein sequence database accession numbers, the sequences to which they refer, and articles cited herein are all incorporated herein by reference in their entireties.

BRIEF SUMMARY OF THE INVENTION

The invention provided herein discloses, inter alia, compositions and methods for a low temperature process for hydrolyzing granular starch within ground whole or fractionated grains into highly fermentable sugars for use as feedstocks for the production of isoprene, isoprenoid precursor molecules, and/or isoprenoids.

In one aspect, provided herein are methods for the production of isoprene by recombinant host cells in culture, wherein the host cells comprise one or more heterologous nucleic acids encoding an isoprene synthase polypeptide and one or more mevalonate (MVA) pathway polypeptides, the method comprising: (a) inactivating endogenous enzyme activity in a whole or fractionated grain; (b) treating the whole or fractionated grain with a starch solubilizing alpha amylase and a glucoamylase, wherein the treatment is at a temperature at or below the initial gelatinization temperature of the starch in the grain, wherein the concentration of the alpha amylase is between about 5 to 20 AAU/gds, and wherein the treatment produces a fermentable sugar feedstock; (c) culturing the recombinant host cells in culture media comprising the fermentable sugar feedstock; and (d) producing isoprene. In some aspects, the treatment is at a temperature of about 0 to about 30° C. below the initial gelatinization temperature of the starch in the grain. In some aspects, the concentration of alpha amylase is about 6 AAU/g ds to about 10 AAU/g ds. In some aspects, the isoprene synthase polypeptide is a plant isoprene synthase polypeptide. In some aspects, the plant isoprene synthase polypeptide is a kudzu isoprene synthase polypeptide. In some aspects, the isoprene synthase polypeptide is a polypeptide from *Pueraria* or *Populus* or a hybrid, *Populus alba×Populus tremula*. In some aspects, the isoprene synthase polypeptide is selected from the group consisting of *Pueraria montana* or *Pueraria lobata*, *Populus tremuloides*, *Populus alba*, *Populus nigra*, and *Populus trichocarpa*. In some aspects, the recombinant cells further comprise one or more heterologous nucleic acids encoding a 1-Deoxyxylulose-5-phosphate synthase (DXS) polypeptide. In some aspects, said one or more heterologous nucleic acids is placed under the control of an inducible promoter or a constitutive promoter. In some aspects, said one or more heterologous nucleic acids is cloned into a multicopy plasmid. In some aspects, said one or more heterologous nucleic acids is integrated into a chromosome of the cells. In some aspects of any of the aspects provided above, the host cells are bacterial, algal, fungal or yeast cells. In some aspects, the bacterial cells are gram-positive bacterial cells or gram-negative bacterial cells. In some aspects, the bacterial cells are selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells. In some aspects, the algal cells are selected from the group consisting of green algae, red algae, glaucophytes, chlorarachniophytes, euglenids, chromista, or dinoflagellates. In some aspects, the host cells are fungal cells. In some aspects, the fungal cells are filamentous fungi. In some aspects, the host cells are yeast cells. In some aspects, the yeast cells are is selected from the group consisting of *Saccharomyces* sp., *Schizosaccharomyces* sp., *Pichia* sp., or *Candida* sp. In some aspects, the yeast cells are *Saccharomyces cerevisiae*. In some aspects, the whole or fractionated grain is whole crown corn or corn endosperm. In some aspects, endogenous enzyme activity is inactivated by exposing the whole or fractionated grain to low pH. In some aspects, the fermentable sugar feedstock comprises a reduced concentration of DP-2 saccharides in comparison to fermentable sugar feedstocks that are not made by the inactivation of step (a) and the treatment of step (b). In some aspects, the reduced concentration of DP-2 saccharides comprises reduced concentration of kojibiose and/or nigerose. In some aspects, greater than about 90% of the starch from the whole or fractionated grain is solubilized. In some aspects, the solubilized starch comprises greater than about 90% fermentable sugars. In some aspects, the alpha amylase is selected from the group consisting of SPEZYME® XTRA, SPEZYME® Alpha, SPEZYME® RSL, Liquozyme SC, and Fuelzyme. In some aspects of any of the aspects above, the method further comprises treating the whole or fractionated grain with one or more enzymes selected from the group consisting of: cellulases, hemicellulases, pullulanases, pectinases, phytases, and proteases. In some aspects of any of the aspects above, the method further comprises treating the aqueous slurry with an acid fungal alpha amylase. In some aspects of any of the aspects above, the method further comprises treating the aqueous slurry with AmyE or an AmyE variant. In some aspects of any of the aspects above and herein, the method further comprises treating the aqueous slurry with a phytase. In some aspects of any of the aspects above, the treatment is at a temperature of about 55 to about 65° C. In some aspects of any of the aspects above, glucoamylase is at a concentration of about 0.025 GAU/g ds to about 0.075 GAU/g ds. In some aspects of any of the aspects above, glucoamylase is at a concentration of about 0.075 GAU/g ds to about 0.2 GAU/g ds. In some aspects of any of the aspects above, the method further comprises recovering the isoprene.

In one aspect, provided herein are methods for the production of isoprenoids by recombinant host cells in culture, wherein the host cells comprise one or more heterologous nucleic acids encoding one or more mevalonate (MVA) pathway polypeptides and one or more polyprenyl pyrophosphate synthase polypeptides, the method comprising: (a) inactivating endogenous enzyme activity in a whole or fractionated grain; (b) treating the whole or fractionated grain with a starch solubilizing alpha amylase and a glucoamylase, wherein the treatment is at a temperature below the gelatinization temperature of the starch in the grain, wherein the concentration of the alpha amylase is high, and wherein the treatment produces a fermentable sugar feedstock; (c) culturing the recombinant host cells in culture media comprising the fermentable sugar feedstock; and (d) producing isoprenoids. In some aspects, the method further comprises recovering the isoprenoids. In some aspects, the isoprenoid is selected from group consisting of monoterpenes, diterpenes, triterpenes, tetraterpenes, sequiterpene, polyterpene. abietadiene, amorphadiene, carene, α-famesene, β-farnesene, farnesol, geraniol, geranylgeraniol, linalool, limonene, myrcene, nerolidol, ocimene, patchoulol, β-pinene, sabinene, γ-terpinene, terpindene and valencene. In some aspects, the treatment is at a temperature of about 0 to about 30° C. below the initial gelatinization temperature of the starch in the grain. In some aspects, the concentration of alpha amylase is about 6 AAU/g ds to about 10 AAU/g ds. In some aspects, the recombinant cells further comprise one or more heterologous nucleic acids encoding a 1-Deoxyxylulose-5-phosphate synthase (DXS) polypeptide. In some aspects, said one or more heterologous nucleic acids is placed under the control of an inducible promoter or a constitutive promoter. In some aspects, said one or more heterologous nucleic acids is cloned into a multicopy plasmid. In some aspects, said one or more heterologous nucleic acids is integrated into a chromosome of the cells. In some aspects of any of the aspects above, the host cells are bacterial, algal, fungal or yeast cells. In some aspects, the bacterial cells are gram-positive bacterial cells or gram-negative bacterial cells. In some aspects, the bacterial cells are selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells. In some aspects, the algal cells are selected from the group consisting of green algae, red algae, glaucophytes, chlorarachniophytes, euglenids, chromista, or dinoflagellates. In some aspects, the host cells are fungal cells. In some aspects, the fungal cells are filamentous fungi. In some aspects, the host cells are yeast cells. In some aspects, the yeast cells are is selected from the group consisting of *Saccharomyces* sp., *Schizosaccharomyces* sp., *Pichia* sp., or *Candida* sp. In some aspects, the yeast cells are *Saccharomyces cerevisiae*. In some aspects, the whole or fractionated grain is whole crown corn or corn endosperm. In some aspects, endogenous enzyme activity is inactivated by exposing the whole or fractionated grain to low pH. In some aspects, the fermentable sugar feedstock comprises a reduced concentration of DP-2 saccharides in comparison to fermentable sugar feedstocks that are not made by the inactivation of step (a) and the treatment of step (b). In some aspects, the reduced concentration of DP-2 saccharides comprises reduced concentration of kojibiose and/or nigerose. In some aspects, greater than about 90% of the starch from the whole or fractionated grain is solubilized. In some aspects, the solubilized starch comprises greater than about 90% fermentable sugars. In some aspects, the alpha amylase is selected from the group consisting of SPEZYME® XTRA, SPEZYME® Alpha, SPEZYME® RSL, Liquozyme SC, and Fuelzyme. In some aspects of any of the aspects above, the method further comprises treating the whole or fractionated grain with one or more enzymes selected from the group consisting of: cellulases, hemicellulases, pullulanases, pectinases, phytases, and proteases. In some aspects of any of the aspects above, the method further comprises treating the aqueous slurry with an acid fungal alpha amylase. In some aspects of any of the aspects above, the method further comprises treating the aqueous slurry with AmyE or an AmyE variant. In some aspects of any of the aspects above, the treatment is at a temperature of about 55 to about 65° C. In some aspects of any of the aspects above, the method further comprises glucoamylase is at a concentration of about 0.025 GAU/g ds to about 0.075 GAU/g ds. In some aspects of any of the aspects above, glucoamylase is at a concentration of about 0.075 GAU/g ds to about 0.2 GAU/g ds.

In one aspect, provided herein are methods for the production of mevalonate by recombinant host cells in culture, wherein the host cells comprise one or more heterologous nucleic acids encoding one or more mevalonate (MVA) pathway polypeptides, the method comprising: (a) inactivating endogenous enzyme activity in a whole or fractionated grain; (b) treating the whole or fractionated grain with a starch solubilizing alpha amylase and a glucoamylase, wherein the treatment is at a temperature below the gelatinization temperature of the starch in the grain, wherein the concentration of the alpha amylase is high, and wherein the treatment produces a fermentable sugar feedstock; (c) culturing the recombinant host cells in culture media comprising the fermentable sugar feedstock; and (d) producing mevalonate. In some aspects, the method further comprises recovering the mevalonate. In some aspects, the treatment is at a temperature of about 0 to about 30° C. below the initial gelatinization temperature of the starch in the grain. In some aspects, the concentration of alpha amylase is about 6 AAU/g ds to about 10 AAU/g ds. In some aspects, the isoprene synthase polypeptide is a plant isoprene synthase polypeptide. In some aspects, the plant isoprene synthase polypeptide is a kudzu isoprene synthase polypeptide. In some aspects, the recombinant cells further comprise one or more heterologous nucleic acids encoding a 1-Deoxyxylulose-5-phosphate synthase (DXS) polypeptide. In some aspects, said one or more heterologous nucleic acids is placed under the control of an inducible promoter or a constitutive promoter. In some aspects, one or more heterologous nucleic acids is cloned into a multicopy plasmid. In some aspects, said one or more heterologous nucleic acids is integrated into a chromosome of the cells. In some aspects of any of the aspects above, the host cells are bacterial, algal, fungal or yeast cells. In some aspects, the bacterial cells are gram-positive bacterial cells or gram-negative bacterial cells. In some aspects, the bacterial cells are selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B.*

*lautus, B. thuringiensis, S. albus, S. lividans, S. coelicolor, S. griseus, Pseudomonas* sp., and *P. alcaligenes* cells. In some aspects, the algal cells are selected from the group consisting of green algae, red algae, glaucophytes, chlorarachniophytes, euglenids, chromista, or dinoflagellates. In some aspects, the host cells are fungal cells. In some aspects, the fungal cells are filamentous fungi. In some aspects, the host cells are yeast cells. In some aspects, the yeast cells are is selected from the group consisting of *Saccharomyces* sp., *Schizosaccharomyces* sp., *Pichia* sp., or *Candida* sp. In some aspects, the yeast cells are *Saccharomyces cerevisiae*. In some aspects, the whole or fractionated grain is whole crown corn or corn endosperm. In some aspects, endogenous enzyme activity is inactivated by exposing the whole or fractionated grain to low pH. In some aspects, the fermentable sugar feedstock comprises a reduced concentration of DP-2 saccharides in comparison to fermentable sugar feedstocks that are not made by the inactivation of step (a) and the treatment of step (b). In some aspects, the reduced concentration of DP-2 saccharides comprises reduced concentration of kojibiose and/or nigerose. In some aspects, greater than about 90% of the starch from the whole or fractionated grain is solubilized. In some aspects, the solubilized starch comprises greater than about 90% fermentable sugars. In some aspects, the alpha amylase is selected from the group consisting of SPEZYME® XTRA, SPEZYME® Alpha, SPEZYME® RSL, Liquozyme SC, and Fuelzyme. In some aspects of any of the aspects above, the method further comprises treating the whole or fractionated grain with one or more enzymes selected from the group consisting of: cellulases, hemicellulases, pullulanases, pectinases, phytases, and proteases. In some aspects of any of the aspects above, the method further comprises, treating the aqueous slurry with an acid fungal alpha amylase. In some aspects of any of the aspects above, the method further comprises treating the aqueous slurry with AmyE or an AmyE variant. In some aspects of any of the aspects above, the treatment is at a temperature of about 55 to about 65° C. In some aspects of any of the aspects above, glucoamylase is at a concentration of about 0.025 GAU/g ds to about 0.075 GAU/g ds. In some aspects of any of the aspects above, glucoamylase is at a concentration of about 0.075 GAU/g ds to about 0.2 GAU/g ds.

DETAILED DESCRIPTION

Figure 1:
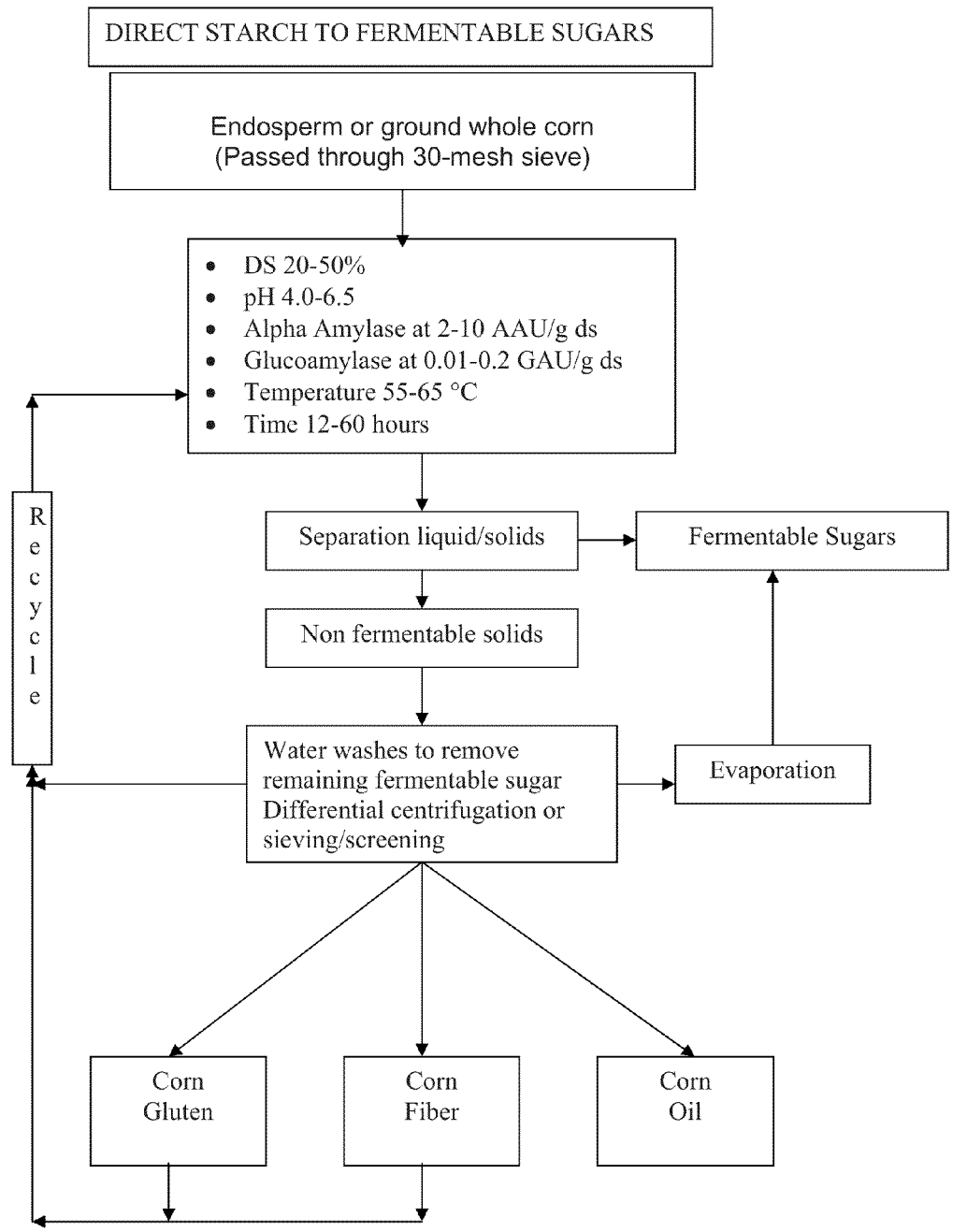
FIG. 1 depicts the process for obtaining a fermentable sugar feedstock from starch at temperatures below the gelatinization temperature of starch in a grain.

The invention provides, inter alia, compositions and methods for the low-temperature production of sugar feedstocks that are useful as fermentable carbon sources for the industrial production of one or more products, such as isoprene, isoprenoid precursor molecules, and/or isoprenoids, by a fermenting microorganism.

Dry grind and wet mill grain processes traditionally cook grains and other starch feedstocks with thermostable enzymes to begin the process of converting insoluble starch to fermentable sugars. In an exemplary dry grind process, the entire corn kernel or other starchy grain can be first ground and then processed without separating the various cellular components of the grain. In general, two enzymatic steps can be involved in the hydrolysis of starch to glucose: liquefaction followed by saccharification. During liquefaction, insoluble starch granules can be slurried in water, gelatinized with heat, and hydrolyzed by a thermostable alpha amylase (EC.3.2.1.1, alpha (1-4)-glucan glucanohydrolase), for example, an alpha amylase from a *Bacillus* species, in the presence of added calcium. Bacterially derived thermostable alpha amylases are used to first liquefy the starch at high temperatures (these can be greater than 95° C.) at an acidic pH (e.g., pH 5.4-6.5) to a low DE (dextrose equivalent) soluble starch hydrolysate. Saccharification further hydrolyzes the soluble low DE dextrins to glucose via an enzyme having glucoamylase (EC 3.2.1.3, alpha (1,4)-glucan glucohydrolase) activity. Commercial glucoamylases are primarily derived from fungal sources, for example *Aspergillus, Trichoderma, Rhizopus, Talaromyces* and *Tramates* species. The resulting glucose syrup may then be used as a feedstock to be converted into other commercially important end-products.

The present invention provides for a low-temperature process for the efficient production of fermentable sugar feedstocks that avoids the extensive milling, long fermentation times, and risk of microbial infection associated with currently available low temperature processes. The inventors have discovered, inter alia, that the starch present in unrefined grains can be hydrolyzed to yield feedstocks containing up to about 98% (such as up to about 90%, 91%, 92%, 93%, 94%, 95%, 96%, or 97%) fermentable sugars at temperatures at or below the initial gelatinization temperature of the starch in the grain. Without being bound to theory, and in one aspect, one or more endogenous enzyme(s) present in certain grains can effectively hydrolyze a starch source into a fermentable feedstock with a distinct DP2 saccharide profile when used in combination with high doses of exogenous alpha amylase and glucoamylase. The methods of the present application, therefore, represent an improvement over what has previously been practiced in the art, in that starch hydrolysis can be performed relatively rapidly on course ground or fractionated grains and at temperatures significantly below those required for most dry mill or wet mill processes that require high temperatures for starch hydrolysis. Consequently, the methods of the present invention require significantly less energy for the hydrolysis of starch into fermentable sugar feedstocks which can then be used as a carbon source for the production of one or more products, such as isoprene, isoprenoid precursor molecules, and/or isoprenoids, by a fermenting organism. These methods additionally do not require the extensive grain processing and/or long fermentation times which can increase the risk of microbial feedstock contamination observed in other less energy-intensive hydrolysis methods.

I. GENERAL TECHNIQUES

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, "*Molecular Cloning: A Laboratory Manual*", second edition (Sambrook et al., 1989); "*Oligonucleotide Synthesis*" (M. J. Gait, ed., 1984); "*Animal Cell Culture*" (R. I. Freshney, ed., 1987); "*Methods in Enzymology*" (Academic Press, Inc.); "*Current Protocols in Molecular Biology*" (F. M. Ausubel et al., eds., 1987, and periodic updates); "*PCR: The Polymerase Chain Reaction*", (Mullis et al., eds., 1994). Singleton et al., "*Dictionary of Microbiology and Molecular Biology*" 2nd ed., J. Wiley & Sons (New York, N.Y. 1994), and Baltz et al., "*Manual of Industrial Microbiology and Biotechnology*" $3^{rd}$ ed., (Washington, D.C.: ASM Press, 2010), provide one skilled in the art with a general guide to many of the terms used in the present application.

II. DEFINITIONS

As used herein the term "starch" refers to any material comprised of the complex polysaccharide carbohydrates of plants, comprised of amylose and/or amylopectin with the formula $(C_6H_{10}O_5)_x$, wherein X can be any number. In particular, the term refers to any plant-based material including but not limited to grains, grasses, tubers and roots and more specifically wheat, barley, corn, rye, rice, sorghum (milo), molasses, legumes, cassava, millet, potato, sweet potato, sugar cane, and tapioca.

The term "granular starch" refers to uncooked (raw) starch, which has not been subjected to gelatinization.

The term "starch gelatinization" means solubilization of a starch molecule to form a viscous suspension.

"Initial gelatinization temperature" refers to the lowest temperature at which gelatinization of a starch substrate begins. The exact temperature can be readily determined by the skilled artisan and depends upon the specific starch substrate. Initial gelatinization temperature may further depend on the particular variety of plant species from which the starch is obtained and the growth conditions. According to the present teachings, the initial gelatinization temperature of a given starch is the temperature at which birefringence is lost in 5% of the starch granules using the method described by Gorinstein & Lii, *Starch/Stark,* 1992, 44(12):461-466. The initial starch gelatinization temperature ranges for a number of granular starches which may be used in accordance with the processes herein include barley (52-59° C.), wheat (58-64° C.), rye (57-70° C.), corn (62-72° C.), high amylose corn (67-80° C.), rice (68-77° C.), sorghum (68-77° C.), potato (58-68° C.), tapioca (59-69° C.) and sweet potato (58-72° C.) (Swinkels, pg. 32-38 in *Starch Conversion Technology*, Van Beynum et al., eds. (1985; Marcel Dekker Inc., New York) and *The Alcohol Textbook* $3^{rd}$ Ed. A Reference for the Beverage, Fuel and Industrial Alcohol Industries, Jacques et al., eds. (1999; Nottingham University Press, UK)). Gelatinization involves melting of crystalline areas, hydration of molecules and irreversible swelling of granules. The gelatinization temperature occurs in a range for a given grain because crystalline regions vary in size and/or degree of molecular order or crystalline perfection. *Starch Hydrolysis Products Worldwide Technology, Production, and Applications* (Shenck and Hebeda, eds. (1992; VCH Publishers, Inc., New York) at p. 26.

The term "DE" or "dextrose equivalent" is an industry standard for measuring the concentration of total reducing sugars, calculated as D-glucose on a dry weight basis. Unhydrolyzed granular starch has a DE that is essentially 0 and D-glucose has a DE of 100.

The term "endosperm" refers to the grain after separating the germ and crude fiber fractions.

The term "fermentation broth" refers to fermentation medium containing the end products after fermentation.

The term "direct starch to fermentable sugars" ("DSTFS") refers to a process whereby granular starch hydrolysates are formed using direct conversion of granular starch to fermentable sugars according to of the processes disclosed in the present teachings.

The term "DP" refers to degree of polymerization to the number (n) of anhydroglucopyranose units in a given saccharide. Non-limiting examples of DP1 saccharides are the monosaccharides, such as glucose and fructose. Non-limiting examples of DP2 saccharides are disaccharides such as maltose, isomaltose and sucrose. $DP4^+$ (>DP3) denotes polymers with a degree of polymerization of greater than 3.

The term "fermentable sugar" refers to the sugar composition containing DP1 and DP2.

The term "fermenting organism" or "fermenting microorganism" refers to any organism, such as, but not limited to bacterial and fungal organisms, (e.g. yeast and filamentous fungi), suitable for producing a desired fermentation product. Fermenting organisms possess the ability to ferment, (such as to change or convert) sugars, such as glucose, xylose, maltose, fructose, xylose, arabinose and/or mannose, directly or indirectly into a desired fermentation product. Examples of fermenting organisms include fungal organisms, such as yeast, and bacterial organisms such as, but not limited to, *E. coli, Bacillus* spp., *Zymomonas* spp., and *Clostridium* spp. In some aspects, the fermenting organism can be a mircrobe.

The term "ds or DS" refers to dissolved solids and/or dry substance in a solution.

The term "starch-liquefying enzyme" refers to an enzyme that affects the hydrolysis or breakdown of granular starch. Exemplary starch liquefying enzymes include alpha amylases (E.C. 3.2.1.1).

The term "amylases" refer to enzymes that catalyze the hydrolysis of starches.

The term "alpha-amylase (E.C. class 3.2.1.1)" refers to enzymes that catalyze the hydrolysis of alpha-1,4-glucosidic linkages. These enzymes have also been described as those effecting the exo or endohydrolysis of 1,4-α-D-glucosidic linkages in polysaccharides containing 1,4-α-linked D-glucose units. Another term used to describe these enzymes is glycogenase. Exemplary enzymes include alpha-1,4-glucan 4-glucanohydrase glucanohydrolase.

The term "glucoamylase" refers to the amyloglucosidase class of enzymes (EC.3.2.1.3, glucoamylase, alpha-1,4-D-glucan glucohydrolase). These are exo-acting enzymes, which release glucosyl residues from the non-reducing ends of amylose and amylopectin molecules. The enzymes also hydrolyze alpha-1,6 and alpha-1,3 linkages although at much slower rates than alpha 1,4 linkages. Glucoamylases (E.C. 3.2.1.3) are enzymes that remove successive glucose units from the non-reducing ends of starch. The enzyme can hydrolyze both linear and branched glucosidic linkages of starch, amylose and amylopectin.

The term "hydrolysis of starch" refers to the cleavage of glucosidic bonds with the addition of water molecules.

The term "contacting" refers to the placing of the respective enzymes in sufficiently close proximity to the respective substrate to enable the enzymes to convert the substrate to the end product. Those skilled in the art will recognize that mixing solutions of the enzyme with the respective substrates can effect contacting.

The term "fermentable sugar index" refers to the number calculated by using the following formula: ((% DP1+% DP2)/% DP3+% Hr. Sugars)*100.

As used herein, the terms "minimal medium" or "minimal media" refer to growth medium containing the minimum nutrients possible for cell growth, generally without the presence of amino acids. Minimal medium can contain: (1) a carbon source for microbial growth; (2) various salts, which can vary among microbial species and growing conditions; and (3) water. The carbon source can vary significantly, from simple sugars like glucose to more complex hydrolysates of other biomass, such as yeast extract. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

As used herein, the term "polypeptides" includes polypeptides, proteins, peptides, fragments of polypeptides, and fusion polypeptides.

By "heterologous polypeptide" is meant a polypeptide encoded by a nucleic acid sequence derived from a different organism, species, or strain than the host cell. In some aspects, a heterologous polypeptide is not identical to a wild-type polypeptide that is found in the same host cell in nature.

As used herein, a "nucleic acid" refers to two or more deoxyribonucleotides and/or ribonucleotides covalently joined together in either single or double-stranded form.

By "recombinant nucleic acid" is meant a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences.

By "heterologous nucleic acid" is meant a nucleic acid sequence derived from a different organism, species or strain than the host cell. In some aspects, the heterologous nucleic acid is not identical to a wild-type nucleic acid that is found in the same host cell in nature.

As used herein, an "expression control sequence" means a nucleic acid sequence that directs transcription of a nucleic acid of interest. An expression control sequence can be a promoter, such as a constitutive or an inducible promoter, or an enhancer. An expression control sequence can be "native" or heterologous. A native expression control sequence is derived from the same organism, species, or strain as the gene being expressed. A heterologous expression control sequence is derived from a different organism, species, or strain as the gene being expressed. An "inducible promoter" is a promoter that is active under environmental or developmental regulation.

By "operably linked" is meant a functional linkage between a nucleic acid expression control sequence (such as a promoter) and a second nucleic acid sequence, wherein the expression control sequence directs transcription of the nucleic acid corresponding to the second sequence.

The term "isoprene" refers to 2-methyl-1,3-butadiene (CAS#78-79-5). It can be the direct and final volatile C5 hydrocarbon product from the elimination of pyrophosphate from DMAPP. It may not involve the linking or polymerization of IPP molecules to DMAPP molecules. The term "isoprene" is not generally intended to be limited to its method of production unless indicated otherwise herein.

As used herein, the term "isoprenoid" refers to a large and diverse class of naturally-occurring class of organic compounds composed of two or more units of hydrocarbons, with each unit consisting of five carbon atoms arranged in a specific pattern. Isoprenoids can include, but are not limited to, terpenoids (for example, hemiterpenoids, monoterpenoids, sesquiterpenoids, diterpenoids, sesterterpenoids, triterpenoids, tetraterpenoids, and/or polyterpenoids). As used herein, "isoprene" is expressly excluded from the definition of "isoprenoid."

As used herein, the term "mass yield" refers to the mass of the product produced by the recombinant (e.g., bacterial) cells divided by the mass of the glucose consumed by the recombinant cells multiplied by 100.

By "specific productivity," it is meant the mass of the product produced by the bacterial cell divided by the product of the time for production, the cell density, and the volume of the culture.

By "titer," it is meant the mass of the product produced by the recombinant (e.g., bacterial) cells divided by the volume of the culture.

As used herein, the term "cell productivity index (CPI)" refers to the mass of the product produced by the recombinant (e.g., bacterial) cells divided by the mass of the recombinant cells produced in the culture.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

III. STARCH-CONTAINING MATERIAL

Starch-containing materials useful for practicing the methods of the present invention include any starch-containing material. Preferred or exemplary starch-containing material may be obtained from wheat, corn, rye, sorghum (milo), rice, millet, barley, triticale, cassava (tapioca), potato, sweet potato, sugar beets, sugarcane, and legumes such as soybean and peas or any combination thereof. Plant material may include hybrid varieties and genetically modified varieties (e.g. transgenic corn, barley or soybeans comprising one or more heterologous genes). Any part of the plant may be used as a starch-containing material, including but not limited to, plant parts such as leaves, stems, hulls, husks, tubers, cobs, grains and the like.

In some aspects, only the grain product of one or more cereals may be used as a starch-containing material. Cereal grains have three components: the endosperm, germ, and bran. In their natural form (for example, "whole" grain), they are a rich source of vitamins, minerals, carbohydrates, fats, oils, and protein. Grains which are ground whole (i.e., whole ground grains) contain ground endosperm, grain and bran. However, grains may also be fractionated by the separation of the bran and germ from the endosperm, which is mostly carbohydrate and lacks the majority of the other nutrients. Non-limiting examples of whole grains which can be used in the methods disclosed herein include corn, wheat, rye, barley, milo and combinations thereof.

In other aspects, starch-containing material may be obtained from coarsely ground or fractionated cereal grains including fiber, endosperm and/or germ components. Methods for fractionating plant material, such as corn and wheat, are known in the art (Alexander, 1987, "Corn Dry Milling: Process, Products, and Applications," in *Corn Chemistry and Technology*, (Watson & Ramstead eds., American Association of Cereal Chemists, Inc., pgs. 351-376; U.S. Pat. No. 6,899,910, the disclosures of which are incorporated herein by reference). Coarsely ground or fractionated starch-containing material obtained from different sources may be mixed together to obtain material used in the processes of the invention (e.g. corn and milo or corn and barley).

In another aspect, a refined grain may be used in the methods described herein when used in combination with an endogenous enzyme fraction derived from specific grains, such as the endogenous enzyme fractions described below. Refined grains, in contrast to whole grains, refer to grain products such as grain flours that have been modified from their natural composition and are essentially pure starch. Such modification can include, but is not limited to, the mechanical removal of bran and germ, either through grinding or selective sifting. Examples of refined grain include, but are not limited to, corn starch, wheat starch, and rice starch.

A. Milling Starch-Containing Material

In some aspects, starch-containing material may be prepared by means such as milling. Two general milling processes include wet milling or dry milling. In dry milling for example, the whole grain is milled and used in the process. In wet milling the grain is separated (e.g. the germ from the meal). In particular, means of milling whole cereal grains are well known and include the use of hammer mills and roller mills. Methods of milling are well known in the art and reference is made to *The Alcohol Textbook: A Reference for the Beverage, Fuel and Industrial Alcohol Industries*, 3rd edition, (Jacques et al., Eds, 1999; Nottingham University Press, chapters 2 and 4, the contents of which are hereby incorporated by reference), the contents of which are incorporated herein by reference. In some aspects, the milled grain used in the process has a particle size such that more than about 50% (for example, more than about 55%, 60%, 65%, 70%, 75%, 80%, 85%, 90% or 95%) of the material will pass through a sieve with a 500 micron opening (see, for example, International Patent Application Publication No.: WO2004/081193, the contents of which are incorporated by reference).

B. Slurries of Starch-Containing Material

In some aspects of the methods provided herein, an aqueous slurry of coarsely ground or fractionated grain (such as any of the milled grains described herein) may be formed prior to liquefaction and saccharification of the starch contained within. The milled starch-containing material is normally screened to a specified sieve size (such as, but not limited to, a 350 µm, 360 µm, 370 µm, 380 µm, 390 µm, 400 µm, 410 µm, 420 µm, 430 µm, 440 µm, 450 µm, 460 µm, 470 µm, 480 µm, 490 µm, 500 µm, 510 µm, 520 µm, 530 µm, 540 µm, or 500 µm sieve) and is combined with water resulting in aqueous slurry.

In some aspects, the dissolved solids (DS) present in the slurry is between about 20-50%, inclusive, including any percentage in between these values. In other aspects, the DS of the slurry between about 25-50%, about 30-50%, about 35-50%, about 40-50%, or about 45-50%, inclusive. In yet other aspects, the DS of the slurry is between about 20-45%, about 20-40%, about 20-35%, about 20-30%, or about 20-25%, inclusive. In a further aspect, the DS of the slurry is between about 25-45% or about 30-40%, inclusive. The pH of the slurry may range from neutral to acidic. In some aspects, the pH of the slurry is between about 4.0-6.5, inclusive, including any number in between these values. In other aspects, the pH of the slurry is between about 4.2-6.2, about 4.5-6.0, about 4.5-5.5, about 5.5-6.0, or about 5.0-6.0, inclusive. In other aspects, the slurry can be between about 15 to 55% ds w/w (e.g., between about 20 to 50%, 25 to 50%, 25 to 45%, 25 to 40%, or 20 to 35% ds), inclusive.

IV. ENZYMES

The methods described herein can employ one or more enzymes to assist in the liquefaction and saccharification of starch at temperatures below that of the gelatinization temperature of starch in grain.

A. Alpha Amylases

In some aspects, the methods provided herein use at least one alpha amylase for the production of a fermentable feedstock. Specifically, alpha amylases are employed in the methods disclosed herein for the liquefaction of raw or granular starch into viscous short chain dextrins. Alpha amylase is an enzyme having an E.C. number of E.C. 3.2.1.1-3 (including, for example, E.C. 3.2.1.1) that hydrolyses the alpha-bonds of large alpha-linked polysaccharides, such as starch and glycogen, to yield glucose and maltose. It is the major form of amylase found in humans and other mammals. It is also present in seeds containing starch as a food reserve, and is secreted by many microorganisms.

One alpha amylase unit (AAU) of bacterial alpha-amylase activity is the amount of enzyme required to hydrolyze 10 mg of starch per minute from 5% dry substance soluble Lintner starch solution containing 31.2 mM calcium chloride, at 60° C. and 6.0 pH buffered with 30 mM sodium acetate. As understood by those in the art, the quantity of alpha amylase used in the methods of the present invention will depend in part on the enzymatic activity of the particular alpha amylase employed. In some aspects of the methods provided herein, a high concentration of alpha amylase is used to liquefy starch present in a ground or fractionated grain, such as any of the ground or fractionated grains described above. In this context, given the variability in the enzymatic activities of alpha amylases derived from many species of plants, fungus, bacteria, and yeasts, a "high concentration" of alpha amylase means the alpha amylase used for the liquefaction reaction is present at a concentration of between about 1-50 AAU/gds (gram dissolved solids), although in some aspects the alpha amylase is added in an amount between about 2 to 20 AAU/gds. For example, generally an amount of between about 2 to 10 AAU/gds of SPEZYME® XTRA or SPEZYME® Alpha or SPEZYME® RSL. (Genencor-Danisco) is added per gram of ds.

In some aspects, the high concentration of alpha amylase used for the liquefaction reaction in any of the methods described herein can be any of about 1 AAU/gds, 2 AAU/gds, 3 AAU/gds, 4 AAU/gds, 5 AAU/gds, 6 AAU/gds, 7 AAU/gds, 8 AAU/gds, 9 AAU/gds, or 10 AAU/gds, inclusive, including any values in between these concentrations. In some aspects, the high concentration of alpha amylase used for the liquefaction reaction is greater than about 10 AAU/gds, including concentrations greater than about 12 AAU/gds, about 14 AAU/gds, about 16 AAU/gds, about 18 AAU/gds, or about 20 AAU/gds, inclusive, including any concentrations in between these values. In other aspects, the high concentration of alpha amylase used for the liquefaction reaction is between about 3-9 AAU/gds, 4-8 AAU/gds, or 5-7 AAU/gds, inclusive. In still other aspects, the high concentration of alpha amylase used for the liquefaction reaction is between about 3-10 AAU/gds, 4-10 AAU/gds, 5-10 AAU/gds, 6-10 AAU/gds, 7-10 AAU/gds, 8-10 AAU/gds, or 9-10 AAU/gds, inclusive. In a further aspect, the high concentration of alpha amylase used for the liquefaction reaction is between about 3-9 AAU/gds, 3-8 AAU/gds, 3-7 AAU/gds, 3-6 AAU/gds, 3-5 AAU/gds, or 3-4 AAU/gds, inclusive.

Suitable alpha amylases may be naturally occurring as well as recombinant and mutant alpha amylases. In some aspects of the methods described herein, the alpha amylase is a thermostable bacterial alpha amylase or an acid fungal alpha amylase. Exemplary alpha amylases suitable for use in the methods describe herein include, but are not limited to, an alpha amylase derived from a *Bacillus* species (such as, for example, alpha amylases derived from *B. subtilis, B. stearothermophilus, B. lentus, B. licheniformis, B. coagulans*, or *B. amyloliquefaciens*; see U.S. Pat. Nos. 5,763,385; 5,824,532; 5,958,739; 6,008,026 and 6,361,809, the contents of which are incorporated by reference herein in their entireties). Additional exemplary alpha amylases include those expressed by the American Type Culture Collection (ATCC) strains ATCC 39709; ATCC 11945; ATCC 6598; ATCC 6634; ATCC 8480; ATCC 9945A and NCIB 8059. Commercially available alpha amylases contemplated for use in the methods of the invention include, but are not limited to, SPEZYME® AA; SPEZYME® FRED; SPEZYME® Alpha, SPEZYME® XTRA GZYME™ G997 SPEZYME® RSL (Genencor-Danisco), TERMAMYL™ 120-L, LC, Fuelzyme, Liquozyme SC and Liquozyme SUPRA (from Novozymes).

In some aspects, the alpha amylase employed in any of the methods disclosed herein is "Amy E", the production and purification of which are described in U.S. Patent Publication Nos.: US2009/0305935-A1 and US2009/0305360-A1, the disclosures of which are hereby incorporated by reference in their entireties with respect to teachings related to Amy E.

B. Glucoamylases

In some aspects, the methods provided herein use at least one glucoamylase for the saccharification of soluble low DE dextrins. Glucoamylases (EC.3.2.1.3; also known as amyloglucosidase, glucoamylase, or alpha-1,4-D-glucan glucohydrolase) are exo-acting enzymes which release glucosyl residues from the non-reducing ends of amylose and amylopectin molecules. These enzymes also hydrolyze alpha-1,6 and alpha-1,3 linkages although at much slower rates than alpha 1,4 linkages. Glucoamylase can also hydrolyze both linear and branched glucosidic linkages of starch, amylose and amylopectin.

One Glucoamylase Unit (GAU) is the amount of enzyme that liberates one gram of reducing sugars calculated as glucose from a 2.5% dry substance soluble Lintner starch substrate per hour at 60° C. and 4.3 pH buffered with 20 mM sodium acetate. As understood by those in the art, the quantity of glucoamylase used in the methods of the present invention will depend in part on the enzymatic activity of the particular alpha amylase employed. In some aspects, the concentration of glucoamylase used for the saccharification reaction in any of the methods described herein can be any of about 0.01-0.2 GAU/gds, inclusive. In other aspects, the concentration of glucoamylase is between about 0.05-0.15 GAU/gds, inclusive, or between about 0.75-0.1 GAU/gds, inclusive. In still other aspects, the concentration of glucoamylase is between about 0.01-0.2 GAU/gds, 0.03-0.2 GAU/gds, 0.05-0.2 GAU/gds, 0.07-0.2 GAU/gds, 0.09-0.2 GAU/gds, 0.11-0.2 GAU/gds, 0.13-0.2 GAU/gds, 0.15-0.2 GAU/gds, 0.17-0.2 GAU/gds, or 0.19-0.2 GAU/gds, inclusive. In a further aspect, the concentration of glucoamylase is between about 0.01-1.8 GAU/gds, 0.01-1.6 GAU/gds, 0.01-1.4 GAU/gds, 0.01-1.2 GAU/gds, 0.01-1.0 GAU/gds, 0.01-0.8 GAU/gds, 0.01-0.6 GAU/gds, 0.01-0.4 GAU/gds, or 0.01-0.2 GAU/gds, inclusive. In another aspect, the concentration of glucoamylase is any of about 0.025 GAU/gds, about 0.05 GAU/gds, about 0.075 GAU/gds, about 0.1 GAU/gds, or about 0.2 GAU/gds, inclusive, including any concentrations in between these values.

Suitable glucoamylases may be naturally occurring (for example, a glucoamylase derived from bacteria, plants, or fungi) as well as recombinant and mutant glucoamylases. Exemplary glucoamylases suitable for use in the methods described herein include, but are not limited to, glucoamylases secreted from fungi of the genera *Aspergillus niger, Aspergillus awamori, Rhizopus niveus, Rhizopus oryzae, Mucor miehe, Humicola grisea, Aspergillus shirousami* and *Humicola* (*Thermomyces*) *laniginosa* (see, Boel et al., 1984, *EMBO J.*, 3:1097-1102; International Patent Application Publication Nos. WO 92/00381 and WO 00/04136; Chen et al., 1996, *Prot. Eng.* 9:499-505; Taylor et al., 1978, *Carbohydrate Res.*, 61:301-308 and Jensen et al., 1988, *Can. J. Microbiol.* 34:218-223, the disclosures of which are incorporated herein by reference). Other exemplary fungal glucoamylases include those from *Trichoderma reesei, Humicola* (see U.S. Pat. No. 4,618,579, the disclosure of which is incorporated herein by reference), *Humiocla* glucoamylase expressed in *Trichoderma* (see U.S. Pat. No. 7,303,899, the disclosure of which is incorporated herein by reference), *Talaromyces* species such as *Talaromyces emersonii* (see International Patent Application No.: WO99/28448, the disclosure of which is incorporated herein by reference), *Talaromyces leycettanus* (see U.S. Pat. No. RE32153, the disclosure of which is incorporated herein by reference), *Talaromyces dupanti* and thermophilus (see U.S. Pat. No. 4,587,215, the disclosure of which is incorporated herein by reference), *Cladosporium resinae* (formerly known as *Harmoconis resinae*, see U.S. Pat. No. 4,318,927, the disclosure of which is incorporated herein by reference) and the thermophilus fungus *Thermomyces lanuginosus* (formerly known as *Humicola lanuginose* (see Rao et al., 1981, *Biochem. J*, 193:379-387, the disclosure of which is incorporated herein by reference).

Commercial glucoamylases from a variety of fungal sources suitable for use in the methods of the present invention include, for example, Distillase® L-400, FERMENZYME® L-400, G Zyme™ 480 Ethanol, GC 147, DISTILLASE®SSF from Genencor-Danisco and Spirizyme™ Fuel, Spirizyme™ Plus, Spirizyme™ Plus Tech and Spirizyme™ Ultra from Novozymes.

In some aspects, the glucoamylase employed in any of the methods disclosed herein is "*Humicola*-Glucoamylase (H-GA)", the recombinant expression of which in a *Trichoderma* host is described in U.S. Pat. No. 7,303,899, the disclosure of which is hereby incorporated by reference herein. In other aspects, a *Trichoderma* host expresses a heterologous polynucleotide which encodes a glucoamylase derived from a *Humicola grisea* strain, particularly a strain of *Humicola grisea* var. *thermoidea*.

C. Other Carbohydrate and Grain-Degrading Enzymes

In one aspect of any of the methods provided herein, further enzymes may be used to degrade starch and/or other components (such as lipids and proteins) of any of the ground or fractionated grains described above. Exemplary enzymes suitable for such use include, but are not limited to, other amylases (such as beta amylases, AmyE alpha amylase or a variant thereof or isoamylases), beta-galactosidases, catalases, laccases, cellulases, endoglycosidases, endo-beta-1,4-laccases, other glucosidases, glucose isomerases, glycosyltransferases, lipases, phospholipases, lipooxygenases, beta-laccases, endo-beta-1, 3(4)-laccases, cutinases, peroxidases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, cellobiohydrolases and/or transglutaminases.

V. GRAIN-DERIVED ENDOGENOUS ENZYMES

In some aspects of the methods disclosed herein, endogenous enzymes present in one or more whole ground or fractionated grains, such as any of the grains described herein, can be used to produce a fermentable sugar feedstock. Without being bound to theory, certain unrefined grains (for example, ground corn or milo) or fractionated components thereof (such as an endosperm fraction) can contain one or more endogenous enzyme(s) capable of degrading starch into less complex saccharides possessing a distinct DP2 profile (such as a DP2 profile enriched in kojibiose and nigerose). When used in combination with a high concentration of an alpha amylase and a glucoamylase (such as any alpha amylase or glucoamylase described above), the starch-degrading activity of the endogenous enzyme fraction can be used to solubilize greater than about 90% (such as greater than about 91%, 92%, 93%, 94%, 95%, 96%, 97%, or 98%) of the starch in the grains to fermentable sugars.

Accordingly, in some aspects of the methods described herein, the endogenous enzyme activity can be present in a whole ground or a fractionated grain and, when used in combination with a high concentration of an alpha amylase and a glucoamylase at temperatures at or below the initial gelatinization temperature of the starch in the grain, can degrade the starch in the whole ground or fractionated grain into a fermentable sugar feedstock containing the disaccharides kojibiose and nigerose. In some aspects of the methods described herein, the endogenous enzyme-containing whole ground or fractionated grain can be ground corn, corn endosperm, whole ground milo, or whole ground rice.

In other aspects of the methods described herein, the whole ground or fractionated grain lacks the endogenous enzyme activity described above or the starch source used for production of a fermentable sugar feedstock is a refined starch, such as corn starch, wheat starch, or rice starch, which also lacks the endogenous enzyme activity described above. In this case, a fraction containing the endogenous enzymes can be isolated from a whole ground or fractionated grain which does contain the endogenous enzyme activity for use in the production of a fermentable sugar feedstock that is enriched in the disaccharides kojibiose and nigerose. In some aspects, an isolated fraction containing the endogenous enzyme activity can be obtained by centrifuging an aqueous slurry of a grain that contains the endogenous enzymes (such as an aqueous slurry of ground corn, corn endosperm, whole ground milo, whole ground rice, or whole ground wheat) and isolating the supernatant. For example, an aqueous slurry can be prepared by mixing any of the endogenous enzyme-containing grains described above with DI water in order to produce a slurry with any of about 10%, about 15%, about 20%, about 25%, about 30%, about 35%, about 40%, about 45%, or about 50% dry solids, inclusive, including any percentages in between these values. The slurry can then be incubated at room temperature for any of about 30 min, about 60 min, about 90 min, about 120, about 150 min, about 180 min, about 210 min, about 240 min, about 270 min, or about 300 min, inclusive, including any times in between these values. Following incubation, the slurry can centrifuged to remove heavy solids and the resulting supernatant (extract) will contain the endogenous enzyme fraction. Other methods for extraction of endogenous proteins such as enzymes from plant material such as grains may also be used. These methods are numerous and well known in the art (see, for example, U.S. Pat. No. 6,740,740, the contents of which are incorporated by reference herein in its entirety).

In other aspects of the methods provided herein, it may be advantageous to deactivate the endogenous enzyme activity present in certain grains (such as the grains described above), so that the fermentable sugar feedstock produced from these grains is not enriched in DP2 sugars, such as kojibiose and nigerose. In one aspect, the endogenous enzyme activity described above can be deactivated by temporarily lowering the pH of an aqueous slurry of the grain containing the endogenous enzyme activity. In some aspects, the pH is lowered to any of about pH 1, 1.5, 2, 2.5, 3, 3.5, or 4 to inactivate the endogenous enzyme activity. In other aspects, the slurry is exposed to lowered pH for any of about 30 min, about 60 min, about 90 min, about 120, about 150 min, or about 180 min, inclusive, including any times in between these numbers. In yet other aspects, the slurry is exposed to lowered pH at a temperature of about 37° C., 40° C., 45° C., 50° C., 55° C., 60° C., 65° C., 70° C., 75° C., or 80° C., inclusive, including any temperatures in between these values.

VI. METHODS OF THE INVENTION

Provided herein are methods for making a fermentable sugar feedstock by treating an aqueous slurry of ground or fractionated grain (such as any of the ground or fractionated grains described above) with a high concentration of a starch solubilizing alpha amylase and a glucoamylase. The treatment is conducted at a temperature below the gelatinization temperature of the starch in the grain. Additionally, the fermentable sugar feedstocks produced by the methods disclosed herein can possess a higher concentration of DP-2 saccharides in comparison to sugar feedstocks that are made by other methods.

Also provided herein are methods for the production of a fermentable sugar feedstock by treating a refined granular starch or a whole or fractionated grain that lacks an endogenous enzyme activity with a high concentration of a starch solubilizing alpha amylase, a glucoamylase, and an enzyme-containing extract isolated from a grain. Additionally, the fermentable sugar feedstocks produced by the methods disclosed herein can possess a higher concentration of DP-2 saccharides in comparison to sugar feedstocks made by other methods In some aspects, the enzyme-containing extract is derived from whole ground corn, corn endosperm, whole ground milo, whole ground rice, or any combinations thereof using any of the derivation methods disclosed herein. In another aspect, the refined granular starch is corn starch, rice starch, or wheat starch.

In some aspects of the methods provided herein, treatment of the slurry with a high concentration of alpha amylase (as further detailed below) and a glucoamylase is conducted at a temperature at or below the initial gelatinization temperature of the starch in the grain. The initial gelatinization temperature of starch depends upon many variable such as the grain type and the conditions in which it was grown (e.g. water availability), the amount of water present in the aqueous slurry, the pH, and the types and amount of other molecules present in the grains (such as lipids and protein). Some types of unmodified native starches start swelling at 55° C., other types at 85° C. (Belitz et al., Food Chemistry, 3$^{rd}$ ed., (2004, Springer), pg. 318-23). The initial gelatinization temperature can also depend on the degree of cross-linking of amylopectin (one of the two components of starch, the other being amylose) which is determined in large part by the action of one or more endogenous starch synthase genes (see, e.g., U.S. Patent Application Publication No.: 2008/0201807). Consequently, in some aspects, the treatment is conducted at a temperature between about 0° C. to about 40° C. (such as between about 0° C. to about 30° C.) below the initial gelatinization temperature of the starch present in a particular grain used in any of the methods disclosed herein. In other aspects, the treatment is conducted at a temperature between about 0 to 5° C., between about 2 to 7° C., between about 4 to 9° C., between about 6 to 11° C., between about 8 to 13° C., between about 10 to 15° C., between about 12 to 17° C., between about 13 to 19° C., between about 15 to 21° C., between about 17 to 23° C., between about 19 to 25° C., between about 21 to 27° C., between about 23 to 29° C., between about 25 to 31° C., between about 27 to 33° C., between about 29 to 35° C., between about 31 to 37° C., between about 33 to 39° C. or between about 35 to 40° C., inclusive, below the initial gelatinization temperature of the starch present in a particular grain used in any of the methods disclosed herein. In some aspects, the treatment is conducted at a temperature between about 55-65° C., inclusive. In other aspects, the treatment is conducted at a temperature between about 57-65° C., 59-65° C., 61-65° C., or 63-65 C ° C., inclusive. In yet other aspects, the treatment is conducted at a temperature between about 55-63° C., 55-61° C., 55-59° C., or 55-57° C., inclusive. In other aspects, the treatment is conducted at a temperature at least about 55° C., at least about 57° C., at least about 59° C., at least about 61° C., at least about 63° C., or at least about 65° C. In still further aspects, the treatment is conducted at a temperature no greater than about 65° C., about 63° C., about 61° C., about 59° C., about 57° C., or about 55° C.

In other aspects of the methods provided herein, treatment of the slurry with a high concentration of alpha amylase (as further detailed below) and a glucoamylase can be conducted for between about 12-60 hours. In some aspects, the treatment of the slurry is conducted for between about 12-55 hours, 12-50 hours, 12-45 hours, 12-40 hours, 12-35 hours, 12-30 hours, 12-25 hours, 12-20 hours, or 12-15 hours. In still further aspects, the treatment of the slurry is conducted for between about 15-60 hours, 20-60 hours, 25-60 hours, 30-60 hours, 35-60 hours, 40-60 hours, 45-60 hours, 50-60 hours, or 55-60 hours. In other aspects, the treatment of the slurry is conducted for 15-55, 20-50, 25-45, or 30-40 hours. In another aspect, the treatment of the slurry is conducted for any of about 2 hours, about 4 hours, about 6 hours, about 12 hours, about 24 hours, or about 48 hours, inclusive, including any time in between these numbers.

In other aspects, the glucoamylase can be any of the glucoamylases described above and the concentration of glucoamylase used for the methods described herein can be any of about 0.01-0.2 GAU/gds, inclusive. In other aspects, the concentration of glucoamylase is between about 0.05-0.15 GAU/gds, inclusive, or between about 0.75-0.1 GAU/gds, inclusive. In still other aspects, the concentration of glucoamylase is between about 0.01-0.2 GAU/gds, 0.03-0.2 GAU/gds, 0.05-0.2 GAU/gds, 0.07-0.2 GAU/gds, 0.09-0.2 GAU/gds, 0.11-0.2 GAU/gds, 0.13-0.2 GAU/gds, 0.15-0.2 GAU/gds, 0.17-0.2 GAU/gds, or 0.19-0.2 GAU/gds, inclusive. In a further aspect, the concentration of glucoamylase is between about 0.01-1.8 GAU/gds, 0.01-1.6 GAU/gds, 0.01-1.4 GAU/gds, 0.01-1.2 GAU/gds, 0.01-1.0 GAU/gds, 0.01-0.8 GAU/gds, 0.01-0.6 GAU/gds, 0.01-0.4 GAU/gds, or 0.01-0.2 GAU/gds, inclusive. In another aspect, the concentration of glucoamylase is any of about 0.025 GAU/gds, about 0.05 GAU/gds, about 0.075 GAU/gds, about 0.1 GAU/gds, or about 0.2 GAU/gds, inclusive, including any concentrations in between these values.

In other aspects, the methods described herein may further include the additional step of adding one or more other enzymes used to degrade starch and/or other components (such as lipids and proteins) of any of the ground or fractionated grains described above. In one aspect, the methods described herein further include a step for the addition of one or more other amylases (such as beta amylases, AmyE alpha amylase or a variant thereof or isoamylases), beta-galactosidases, catalases, laccases, cellulases, endoglycosidases, endo-beta-1,4-laccases, other glucosidases, glucose isomerases, glycosyltransferases, lipases, phospholipases, lipooxygenases, beta-laccases, endo-beta-1, 3(4)-laccases, cutinases, peroxidases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, cellobiohydrolases and/or transglutaminases.

In a further aspect of any of the methods provided herein, greater than 80% of the ground or fractionated grain present in the aqueous slurry (such as an aqueous slurry of any of the ground or fractionated grains described above) is solubilized by treatment with a high concentration of a starch solubilizing alpha amylase and a glucoamylase and at a temperature at or below the initial gelatinization temperature of the starch in the grain. In other aspects, at least about 82%, 84%, 86%, 88%, 90%, 91%, 92%, 93%, 94%, 95%, 96%, 97%, 98%, 99%, or 100% of the ground or fractionated grain is solubilized. In another aspect of the methods provided herein, the solubilized starch can be greater than about 80% fermentable sugars (such as greater than about 82%, 84%, 86%, 88%, 90%, 91%, 92%, 93%, 94%, 95%, 96%, 97%, 98%, 99%, or 100% fermentable sugars).

Depending on the treatment conditions used in the methods described herein (such as for example, length of treatment, concentration of alpha amylase and glucoamylase, temperature of the treatment, or any other treatment variable disclosed herein), the fermentable sugar feedstocks will be made up of primarily DP1 and DP2 sugars. In some aspects, the fermentable sugar feedstock can be at least about 60% DP1 sugars (for example, glucose). In another aspect, the fermentable sugar feedstocks can be at least about 60%, 65%, 70%, 75%, 80%, 82%, 84%, 86%, 88%, 90%, 91%, 92%, 93%, 94%, or 95% DP1 sugars, inclusive, including any percentages in between these values. In a further aspect, the fermentable sugar feedstock can be no more than about 30% DP2 sugars (for example, maltose or isomaltose). In another aspect, the fermentable sugar feedstock can be no more than about 27%, 25%, 20%, 15%, 14%, 13%, 12%, 11%, 10, 9%, 8%, 7%, 6%, 5%, 4%, 3%, 2%, or 1%, inclusive, including any percentage in between these values, DP2 sugars.

The fermentable sugar feedstock produced using any of the methods disclosed herein can contain a higher concentration of DP2 saccharides in comparison to fermentable sugar feedstocks produced by methods wherein ground or fractionated grain present in the aqueous slurry are not solubilized by treatment with a high concentration of a starch solubilizing alpha amylase and a glucoamylase and at a temperature at or below the initial gelatinization temperature of the starch in the grain. In one aspect, the feedstocks produced using the methods described herein can be rich in DP2 saccharides, such as kojibiose and nigerose. Kojibiose (2R,3S,4R,5R)-3,4,5,6-tetrahydroxy-2-[(2R,3R,4S,5S,6R)-3,4,5-trihydroxy-6-(hydroxymethyl)oxan-2-yl]oxyhexanal) is a disaccharide and is commonly observed as a byproduct of the caramelization of glucose. Nigerose ((2R,3S,4S,5R,6R)-2-(Hydroxymethyl)-6-[(3R,4S,5R,6R)-2,3,5-trihydroxy-6-(hydroxymethyl) oxan-4-yl]oxyoxane-3,4,5-triol), also a byproduct of the caramelization of glucose, is a disaccharide made of two glucose residues, connected with an alpha 1-3 link. In some aspects, the DP2 saccharide concentration within feedstocks produced by the methods disclosed herein can be any of about 0.1% DP2 g/100 gds, 0.5% DP2 g/100 gds, 1% DP2 g/100 gds, 2% DP2 g/100 gds, 3% DP2 g/100 gds, 4% DP2 g/100 gds, 5% DP2 g/100 gds, 6% DP2 g/100 gds, or 7% DP2 g/100 gds, inclusive, including any percentages in between these values, kojibiose. In other aspects, the DP2 saccharide concentration within feedstocks produced by the methods disclosed herein can be any of about 0.1% DP2 g/100 gds, 0.5% DP2 g/100 gds, 1% DP2 g/100 gds, 2% DP2 g/100 gds, 3% DP2 g/100 gds, 4% DP2 g/100 gds, or 5% DP2 g/100 gds, inclusive, including any percentages in between these values, nigerose.

In some aspects, it may be desirable to produce a fermentable sugar feedstock that is not enriched in the DP2 saccharides kojibios and nigerose. In these aspects, the following steps can be used: (a) inactivating endogenous enzyme activity in a whole or fractionated grain and (b) treating the whole or fractionated grain with a high concentration of alpha amylase and a glucoamylase. The treatment is at a temperature below the gelatinization temperature of the starch in the grain. In one aspect, the fermentable sugar feedstock can have a decreased concentration of DP-2 saccharides in comparison to fermentable sugar feedstocks that are not made by inactivating endogenous enzyme activity in a whole or fractionated grain. In some aspects, the whole or fractionated grain is whole crown corn or corn endosperm. In some aspects, fermentable sugar feedstocks made using methods wherein endogenous enzyme activity is inactivated contain 0% DP2 g/100 gds or near 0% DP2 g/100 gds concentrations of kojibiose and/or nigerose.

Endogenous enzyme activity in the a whole or fractionated grain can be inactivated by using any of the methods disclosed herein, including, but not limited to, exposure of an aqueous slurry containing the whole or fractionated grain to low pH. In some aspects, the pH is lowered to any of about pH 1, 1.5, 2, 2.5, 3, 3.5, or 4 to inactivate the endogenous enzyme activity. In other aspects, the slurry is exposed to lowered pH for any of about 30 min, about 60 min, about 90 min, about 120, about 150 min, or about 180 min, inclusive, including any times in between these numbers. In yet other aspects, the slurry is exposed to lowered pH at a temperature of about 37° C., 40° C., 45° C., 50° C., 55° C., 60° C., 65° C., 70° C., 75° C., or 80° C., inclusive, including any temperatures in between these values.

VII. USE OF FERMENTABLE SUGAR FEEDSTOCKS FOR THE PRODUCTION OF ISOPRENE, ISOPRENOID PRECURSOR MOLECULES, AND/OR ISOPRENOIDS

Isoprene (2-methyl-1,3-butadiene) is the monomer of natural rubber and also the critical starting material for a variety of synthetic polymers, most notably synthetic rubbers.

Isoprenoids are compounds derived from the isoprenoid precursor molecules IPP and DMAPP. Over 29,000 isoprenoid compounds have been identified and new isoprenoids are being discovered each year. Isoprenoids can be isolated from natural products, such as microorganisms and species of plants that use isoprenoid precursor molecules as a basic building block to form the relatively complex structures of isoprenoids. Isoprenoids are vital to most living organisms and cells, providing a means to maintain cellular membrane fluidity and electron transport.

The fermentable sugar feedstocks produced by any of the methods disclosed herein may be used as a fermentation feedstock in a fermentation process for producing isoprene, isoprenoid precursor molecules, and/or or isoprenoids.

A. Recombinant Cells for the Production of Isoprene, Isoprenoid Precursor Molecules, and/or Isoprenoids In some aspects, any of the cells used in a fermentation process for the production of isoprene, isoprenoid precursor molecules, and/or or isoprenoids can express one or more heterologous nucleic acids encoding one or more polypeptides which increase the cellular production of isoprene, isoprenoid precursor molecules, and/or isoprenoids produced from carbon provided by the fermentable sugar feedstocks described herein. In other aspects, the cells can also harbor specific genomic mutations which either enhance the production of isoprene, isoprenoid precursor molecules, and/or isoprenoids or which increase carbon availability through the metabolic pathways responsible for the production of isoprene, isoprenoid precursor molecules, and/or isoprenoids (such as the MVA pathway).

1. Isoprene Synthase Nucleic Acids and Polypeptides

In some aspects of the invention, the recombinant cells described in any of the compositions or methods described herein express one or more nucleic acids encoding an isoprene synthase polypeptide or a polypeptide having isoprene synthase activity. In some aspects, the isoprene synthase polypeptide is an endogenous polypeptide. In some aspects, the endogenous nucleic acid encoding an isoprene synthase polypeptide is operably linked to a constitutive promoter. In some aspects, the endogenous nucleic acid encoding an isoprene synthase polypeptide is operably linked to an inducible promoter. In some aspects, the endogenous nucleic acid encoding an isoprene synthase polypeptide is operably linked to a strong promoter. In some aspects, more than one endogenous nucleic acid encoding an isoprene synthase polypeptide is used (e.g, 2, 3, 4, or more copies of an endogenous nucleic acid encoding an isoprene synthase polypeptide). In a particular aspect, the cells are engineered to overexpress the endogenous isoprene synthase pathway polypeptide relative to wild-type cells. In some aspects, the endogenous nucleic acid encoding an isoprene synthase polypeptide is operably linked to a weak promoter. In some aspects, the isoprene synthase polypeptide is a polypeptide from *Pueraria* or *Populus* or a hybrid such as *Populus alba×Populus tremula*.

In some aspects, the isoprene synthase polypeptide is a heterologous polypeptide. In some aspects, the cells comprise more than one copy of a heterologous nucleic acid encoding an isoprene synthase polypeptide. In some aspects, the heterologous nucleic acid encoding an isoprene synthase polypeptide is operably linked to a constitutive promoter. In some aspects, the heterologous nucleic acid encoding an isoprene synthase polypeptide is operably linked to an inducible promoter. In some aspects, the heterologous nucleic acid encoding an isoprene synthase polypeptide is operably linked to a strong promoter. In some aspects, the heterologous nucleic acid encoding an isoprene synthase polypeptide is operably linked to a weak promoter.

The nucleic acids encoding an isoprene synthase polypeptide(s) can be integrated into a genome of the host cells or can be stably expressed in the cells. The nucleic acids encoding an isoprene synthase polypeptide(s) can additionally be on a vector.

Exemplary isoprene synthase nucleic acids include nucleic acids that encode a polypeptide, fragment of a polypeptide, peptide, or fusion polypeptide that has at least one activity of an isoprene synthase polypeptide. Isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Exemplary isoprene synthase polypeptides and nucleic acids include naturally-occurring polypeptides and nucleic acids from any of the source organisms described herein. In addition, variants of isoprene synthase can possess improved activity such as improved enzymatic activity. In some aspects, an isoprene synthase variant has other improved properties, such as improved stability (e.g., thermo-stability), and/or improved solubility.

Standard methods can be used to determine whether a polypeptide has isoprene synthase polypeptide activity by measuring the ability of the polypeptide to convert DMAPP into isoprene in vitro, in a cell extract, or in vivo. Isoprene synthase polypeptide activity in the cell extract can be measured, for example, as described in Silver et al., *J. Biol. Chem.* 270:13010-13016, 1995. In one exemplary assay, DMAPP (Sigma) can be evaporated to dryness under a stream of nitrogen and rehydrated to a concentration of 100 mM in 100 mM potassium phosphate buffer pH 8.2 and stored at −20° C. To perform the assay, a solution of 5 µL of 1 M $MgCl_2$, 1 mM (250 µg/ml) DMAPP, 65 µL of Plant Extract Buffer (PEB) (50 mM Tris-HCl, pH 8.0, 20 mM $MgCl_2$, 5% glycerol, and 2 mM DTT) can be added to 25 µL of cell extract in a 20 ml Headspace vial with a metal screw cap and teflon coated silicon septum (Agilent Technologies) and cultured at 37° C. for 15 minutes with shaking. The reaction can be quenched by adding 200 µL of 250 mM EDTA and quantified by GC/MS.

In some aspects, the isoprene synthase polypeptide is a plant isoprene synthase polypeptide or a variant thereof. In some aspects, the isoprene synthase polypeptide is an isoprene synthase from *Pueraria* or a variant thereof. In some aspects, the isoprene synthase polypeptide is an isoprene synthase from *Populus* or a variant thereof. In some aspects, the isoprene synthase polypeptide is a poplar isoprene synthase polypeptide or a variant thereof. In some aspects, the isoprene synthase polypeptide is a kudzu isoprene synthase polypeptide or a variant thereof. In some aspects, the isoprene synthase polypeptide is a polypeptide from *Pueraria* or *Populus* or a hybrid, *Populus alba×Populus tremula*, or a variant thereof.

In some aspects, the isoprene synthase polypeptide or nucleic acid is from the family Fabaceae, such as the Faboideae subfamily. In some aspects, the isoprene synthase polypeptide or nucleic acid is a polypeptide or nucleic acid from *Pueraria montana* (kudzu) (Sharkey et al., *Plant Physiology* 137: 700-712, 2005), *Pueraria lobata*, poplar (such as *Populus alba, Populus nigra, Populus trichocarpa*, or *Populus alba×tremula* (CAC35696) (Miller et al., *Planta* 213: 483-487, 2001), aspen (such as *Populus tremuloides*) (Silver et al., JBC 270(22): 13010-1316, 1995), English Oak (*Quercus robur*) (Zimmer et al., WO 98/02550), or a variant thereof. In some aspects, the isoprene synthase polypeptide is an isoprene synthase from *Pueraria montana, Pueraria lobata, Populus tremuloides, Populus alba, Populus nigra*, or *Populus trichocarpa* or a variant thereof. In some aspects, the isoprene synthase polypeptide is an isoprene synthase from *Populus alba* or a variant thereof. In some aspects, the nucleic acid encoding the isoprene synthase (e.g., isoprene synthase from *Populus alba* or a variant thereof) is codon optimized.

In some aspects, the isoprene synthase nucleic acid or polypeptide is a naturally-occurring polypeptide or nucleic acid (e.g., naturally-occurring polypeptide or nucleic acid from *Populus*). In some aspects, the isoprene synthase nucleic acid or polypeptide is not a wild-type or naturally-occurring polypeptide or nucleic acid. In some aspects, the isoprene synthase nucleic acid or polypeptide is a variant of a wild-type or naturally-occurring polypeptide or nucleic acid (e.g., a variant of a wild-type or naturally-occurring polypeptide or nucleic acid from *Populus*).

In some aspects, the isoprene synthase polypeptide is a variant. In some aspects, the isoprene synthase polypeptide is a variant of a wild-type or naturally occurring isoprene synthase. In some aspects, the variant has improved activity such as improved catalytic activity compared to the wild-type or naturally occurring isoprene synthase. The increase in activity (e.g., catalytic activity) can be at least about any of 10%, 20%, 30%, 40%, 50%, 60%, 70%, 80%, 90%, or 95%. In some aspects, the increase in activity such as catalytic activity is at least about any of 1 fold, 2 folds, 5 folds, 10 folds, 20 folds, 30 folds, 40 folds, 50 folds, 75 folds, or 100 folds. In some aspects, the increase in activity such as catalytic activity is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the variant has improved solubility compared to the wild-type or naturally occurring isoprene synthase. The increase in solubility can be at least about any of 10%, 20%, 30%, 40%, 50%, 60%, 70%, 80%, 90%, or 95%. The increase in solubility can be at least about any of 1 fold, 2 folds, 5 folds, 10 folds, 20 folds, 30 folds, 40 folds, 50 folds, 75 folds, or 100 folds. In some aspects, the increase in solubility is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the isoprene synthase polypeptide is a variant of naturally occurring isoprene synthase and has improved stability (such as thermo-stability) compared to the naturally occurring isoprene synthase.

In some aspects, the variant has at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200% of the activity of a wild-type or naturally occurring isoprene synthase. The variant can share sequence similarity with a wild-type or naturally occurring isoprene synthase. In some aspects, a variant of a wild-type or naturally occurring isoprene synthase can have at least about any of 40%, 50%, 60%, 70%, 75%, 80%, 90%, 91%, 92%, 93%, 94%, 95%, 96%, 97%, 98%, 99%, 99.5%, or 99.9% amino acid sequence identity as that of the wild-type or naturally occurring isoprene synthase. In some aspects, a variant of a wild-type or naturally occurring isoprene synthase has any of about 70% to about 99.9%, about 75% to about 99%, about 80% to about 98%, about 85% to about 97%, or about 90% to about 95% amino acid sequence identity as that of the wild-type or naturally occurring isoprene synthase.

In some aspects, the variant comprises a mutation in the wild-type or naturally occurring isoprene synthase. In some aspects, the variant has at least one amino acid substitution, at least one amino acid insertion, and/or at least one amino acid deletion. In some aspects, the variant has at least one amino acid substitution. In some aspects, the number of differing amino acid residues between the variant and wild-type or naturally occurring isoprene synthase can be one or more, e.g. 1, 2, 3, 4, 5, 10, 15, 20, 30, 40, 50, or more amino acid residues. Naturally occurring isoprene synthases can include any isoprene synthases from plants, for example, kudzu isoprene synthases, poplar isoprene synthases, English oak isoprene synthases, and willow isoprene synthases. In some aspects, the variant is a variant of isoprene synthase from *Populus alba*. In some aspects, the variant of isoprene synthase from *Populus alba* has at least one amino acid substitution, at least one amino acid insertion, and/or at least one amino acid deletion. In some aspects, the variant is a truncated *Populus alba* isoprene synthase. In some aspects, the nucleic acid encoding variant (e.g., variant of isoprene synthase from *Populus alba*) is codon optimized (for example, codon optimized based on host cells where the heterologous isoprene synthase is expressed).

The isoprene synthase polypeptide provided herein can be any of the isoprene synthases or isoprene synthase variants described in WO 2009/132220, WO 2010/124146, and U.S. Patent Application Publication No.: 2010/0086978, the contents of which are expressly incorporated herein by reference in their entirety with respect to the isoprene synthases and isoprene synthase variants.

Any one of the promoters described herein (e.g., promoters described herein and identified in the Examples of the present disclosure including inducible promoters and constitutive promoters) can be used to drive expression of any of the isoprene synthases described herein.

Suitable isoprene synthases include, but are not limited to, those identified by Genbank Accession Nos. AY341431, AY316691, AY279379, AJ457070, and AY182241. Types of isoprene synthases which can be used in any one of the compositions or methods including methods of making microorganisms encoding isoprene synthase described herein are also described in International Patent Application Publication Nos. WO2009/076676, WO2010/003007, WO2009/132220, WO2010/031062, WO2010/031068, WO2010/031076, WO2010/013077, WO2010/031079, WO2010/148150, WO2010/124146, WO2010/078457, and WO2010/148256.

2. MVA Pathway Nucleic Acids and Polypeptides

The complete MVA pathway can be subdivided into two groups: an upper and lower pathway. In the upper portion of the MVA pathway, acetyl Co-A produced during cellular metabolism is converted to mevalonate via the actions of polypeptides having either: (a) (i) thiolase activity or (ii) acetoacetyl-CoA synthase activity, (b) HMG-CoA reductase, and (c) HMG-CoA synthase enzymatic activity. First, acetyl Co-A is converted to acetoacetyl CoA via the action of a thiolase or an acetoacetyl-CoA synthase (which utilizes acetyl-CoA and malonyl-CoA). Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is the rate-limiting step of the mevalonate pathway of isoprenoid production. In the lower MVA pathway, mevalonate is then converted into mevalonate-5-phosphate via the action of mevalonate kinase which is subsequently transformed into 5-diphosphomevalonate by the enzymatic activity of phosphomevalonate kinase. Finally, IPP is formed from 5-diphosphomevalonate by the activity of the enzyme mevalonate-5-pyrophosphate decarboxylase. The mevalonate-dependent biosynthetic pathway is particularly important for the production of the isoprenoid precursor molecules dimethylallyl diphosphate (DMAPP) and isopentenyl pyrophosphate (IPP).

Exemplary MVA pathway polypeptides include, but are not limited to: 3-hydroxy-3-methylglutaryl-CoA synthase (HMG-CoA synthase) polypeptides (e.g., an enzyme encoded by mvaS), 3-hydroxy-3-methylglutaryl-CoA reductase (HMG-CoA reductase) polypeptides (e.g., enzyme encoded by mvaR or enzyme encoded by mvaE that has been modified to be thiolase-deficient but still retains its reductase activity), mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IPP isomerase polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein. In addition, variants of MVA pathway polypeptide that confer the result of better isoprene production can also be used as well.

Non-limiting examples of MVA pathway polypeptides which can be used are described in International Patent Application Publication No. WO2009/076676; WO2010/003007 and WO2010/148150.

a. Nucleic Acids Encoding Polypeptides of the Upper MVA Pathway

The upper portion of the MVA pathway uses acetyl Co-A produced during cellular metabolism as the initial substrate for conversion to mevalonate via the actions of polypeptides having either: (a) (i) thiolase activity or (ii) acetyl-CoA synthase activity, (b) HMG-CoA reductase, and (c) HMG-CoA synthase enzymatic activity. First, acetyl Co-A is converted to acetoacetyl CoA via the action of a thiolase or an acetoacetyl-CoA synthase (which utilizes acetyl-CoA and malonyl-CoA). Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is the rate-limiting step of the mevalonate pathway of isoprenoid production.

Non-limiting examples of upper MVA pathway polypeptides include: acetyl-CoA acetyltransferase (AA-CoA thiolase) polypeptides, acetoacetyl-CoA synthase polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides. Upper MVA pathway polypeptides can include polypeptides, fragments of polypeptides, peptides, and fusions polypeptides that have at least one activity of an upper MVA pathway polypeptide. Exemplary upper MVA pathway nucleic acids include nucleic acids that encode a polypeptide, fragment of a polypeptide, peptide, or fusion polypeptide that has at least one activity of an upper MVA pathway polypeptide. Exemplary MVA pathway polypeptides and nucleic acids include naturally-occurring polypeptides and nucleic acids from any of the source organisms described herein. Thus, it is contemplated herein that any gene encoding an upper MVA pathway polypeptide can be used in the present invention.

In certain embodiments, various options of mvaE and mvaS genes from *L. grayi, E. faecium, E. gallinarum, E. casseliflavus* and/or *E. faecalis* alone or in combination with one or more other mvaE and mvaS genes encoding proteins from the upper MVA pathway are contemplated within the scope of the invention. In other embodiments, an acetoacetyl-CoA synthase gene is contemplated within the scope of the present invention in combination with one or more other genes encoding: (i) 3-hydroxy-3-methylglutaryl-CoA synthase (HMG-CoA synthase) polypeptides and 3-hydroxy-3-methylglutaryl-CoA reductase (HMG-CoA reductase) polypeptides.

Additional non-limiting examples of upper MVA pathway polypeptides which can be used herein are described in International Patent Application Publication No. WO2009/076676; WO2010/003007 and WO2010/148150.

(i) Acetoacetyl-CoA Synthase Nucleic Acids and Polypeptides

The acetoacetyl-CoA synthase gene (aka nphT7) is a gene encoding an enzyme having the activity of synthesizing acetoacetyl-CoA from malonyl-CoA and acetyl-CoA and having minimal activity (e.g., no activity) of synthesizing acetoacetyl-CoA from two acetyl-CoA molecules. See, e.g., Okamura et al., *PNAS* Vol 107, No. 25, pp. 11265-11270 (2010), the contents of which are expressly incorporated herein by teaching about nphT7. An acetoacetyl-CoA synthase gene from an actinomycete of the genus *Streptomyces* CL190 strain was described in JP Patent Publication (Kokai) No. 2008-61506 A and US2010/0285549. Acetoacetyl-CoA synthase can also be referred to as acetyl CoA:malonyl CoA acyltransferase. A representative acetoacetyl-CoA synthase (or acetyl CoA:malonyl CoA acyltransferase) that can be used is Genbank AB540131.1.

In one embodiment, acetoacetyl-CoA synthase of the present invention synthesizes acetoacetyl-CoA from malonyl-CoA and acetyl-CoA via an irreversible reaction. The use of acetoacetyl-CoA synthase to generate acetyl-CoA provides an additional advantage in that this reaction is irreversible while acetoacetyl-CoA thiolase enzyme's action of synthesizing acetoacetyl-CoA from two acetyl-CoA molecules is reversible. Consequently, the use of acetoacetyl-CoA synthase to synthesize acetoacetyl-CoA from malonyl-CoA and acetyl-CoA can result in significant improvement in productivity for isoprene compared with using thiolase to generate the end same product.

Furthermore, the use of acetoacetyl-CoA synthase to produce isoprene provides another advantage in that acetoacetyl-CoA synthase can convert malonyl CoA to acetyl CoA via decarboxylation of the malonyl CoA. Thus, stores of starting substrate are not limited by the starting amounts of acetyl CoA. The synthesis of acetoacetyl-CoA by acetoacetyl-CoA synthase can still occur when the starting substrate is only malonyl-CoA. In one embodiment, the pool of starting malonyl-CoA is increased by using host strains that have more malonyl-CoA. Such increased pools can be naturally occurring or be engineered by molecular manipulation. See, for example Fowler, et al., *Applied and Environmental Microbiology*, Vol. 75, No. 18, pp. 5831-5839 (2009).

In any of the aspects or embodiments described herein, an enzyme that has the ability to synthesize acetoacetyl-CoA from malonyl-CoA and acetyl-CoA can be used. Non-limiting examples of such an enzyme are described herein. In certain embodiments described herein, an acetoacetyl-CoA synthase gene derived from an actinomycete of the genus *Streptomyces* having the activity of synthesizing acetoacetyl-CoA from malonyl-CoA and acetyl-CoA can be used.

An example of such an acetoacetyl-CoA synthase gene is the gene encoding a protein having the amino acid sequence of SEQ ID NO: 1. Such a protein having the amino acid sequence of SEQ ID NO: 1 corresponds to an acetoacetyl-CoA synthase having activity of synthesizing acetoacetyl-CoA from malonyl-CoA and acetyl-CoA and having no activity of synthesizing acetoacetyl-CoA from two acetyl-CoA molecules.

In one embodiment, the gene encoding a protein having the amino acid sequence of SEQ ID NO: 1 can be obtained by a nucleic acid amplification method (e.g., PCR) with the use of genomic DNA obtained from an actinomycete of the *Streptomyces* sp. CL190 strain as a template and a pair of primers that can be designed with reference to JP Patent Publication (Kokai) No. 2008-61506 A.

As described herein, an acetoacetyl-CoA synthase gene for use in the present invention is not limited to a gene encoding a protein having the amino acid sequence of SEQ ID NO: 1 from an actinomycete of the *Streptomyces* sp. CL190 strain. Any gene encoding a protein having the ability to synthesize acetoacetyl-CoA from malonyl-CoA and acetyl-CoA and which does not synthesize acetoacetyl-CoA from two acetyl-CoA molecules can be used in the presently described methods. In certain embodiments, the acetoacetyl-CoA synthase gene can be a gene encoding a protein having an amino acid sequence with high similarity or substantially identical to the amino acid sequence of SEQ ID NO: 1 and having the function of synthesizing acetoacetyl-CoA from malonyl-CoA and acetyl-CoA. The expression "highly similar" or "substantially identical" refers to, for example, at least about 80% identity, at least about 85%, at least about 90%, at least about 91%, at least about 92%, at least about 93%, at least about 94%, at least about 95%, at least about 96%, at least about 97%, at least about 98%, and at least about 99% identity. As used above, the identity value corresponds to the percentage of identity between amino acid residues in a different amino acid sequence and the amino acid sequence of SEQ ID NO: 1, which is calculated by performing alignment of the amino acid sequence of SEQ ID NO: 1 and the different amino acid sequence with the use of a program for searching for a sequence similarity.

In other embodiments, the acetoacetyl-CoA synthase gene may be a gene encoding a protein having an amino acid sequence derived from the amino acid sequence of SEQ ID NO: 1 by substitution, deletion, addition, or insertion of 1 or more amino acid(s) and having the function of synthesizing acetoacetyl-CoA from malonyl-CoA and acetyl-CoA. Herein, the expression "more amino acids" refers to, for example, 2 to 30 amino acids, preferably 2 to 20 amino acids, more preferably 2 to 10 amino acids, and most preferably 2 to 5 amino acids.

In still other embodiments, the acetoacetyl-CoA synthase gene may consist of a polynucleotide capable of hybridizing to a portion or the entirety of a polynucleotide having a nucleotide sequence complementary to the nucleotide sequence encoding the amino acid sequence of SEQ ID NO: 1 under stringent conditions and capable of encoding a protein having the function of synthesizing acetoacetyl-CoA from malonyl-CoA and acetyl-CoA. Herein, hybridization under stringent conditions corresponds to maintenance of binding under conditions of washing at 60° C. 2×SSC. Hybridization can be carried out by conventionally known methods such as the method described in J. Sambrook et al. Molecular Cloning, A Laboratory Manual, 3rd Ed., Cold Spring Harbor Laboratory (2001).

As described herein, a gene encoding an acetoacetyl-CoA synthase having an amino acid sequence that differs from the amino acid sequence of SEQ ID NO: 1 can be isolated from potentially any organism, for example, an actinomycete that is not obtained from the *Streptomyces* sp. CL190 strain. In addition, acetoacetyl-CoA synthase genes for use herein can be obtained by modifying a polynucleotide encoding the amino acid sequence of SEQ ID NO: 1 by a method known in the art. Mutagenesis of a nucleotide sequence can be carried out by a known method such as the Kunkel method or the gapped duplex method or by a method similar to either thereof. For instance, mutagenesis may be carried out with the use of a mutagenesis kit (e.g., product names; Mutant-K and Mutant-G (TAKARA Bio)) for site-specific mutagenesis, product name; an LA PCR in vitro Mutagenesis series kit (TAKARA Bio), and the like.

The activity of an acetoacetyl-CoA synthase having an amino acid sequence that differs from the amino acid sequence of SEQ ID NO: 1 can be evaluated as described below. Specifically, a gene encoding a protein to be evaluated is first introduced into a host cell such that the gene can be expressed therein, followed by purification of the protein by a technique such as chromatography. Malonyl-CoA and acetyl-CoA are added as substrates to a buffer containing the obtained protein to be evaluated, followed by, for example, incubation at a desired temperature (e.g., 10° C. to 60° C.). After the completion of reaction, the amount of substrate lost and/or the amount of product (acetoacetyl-CoA) produced are determined. Thus, it is possible to evaluate whether or not the protein being tested has the function of synthesizing acetoacetyl-CoA from malonyl-CoA and acetyl-CoA and to evaluate the degree of synthesis. In such case, it is possible to examine whether or not the protein has the activity of synthesizing acetoacetyl-CoA from two acetyl-CoA molecules by adding acetyl-CoA alone as a substrate to a buffer containing the obtained protein to be evaluated and determining the amount of substrate lost and/or the amount of product produced in a similar manner.

(ii) Genes Encoding mvaE and mvaS Polypeptides

In certain embodiments, various options of mvaE and mvaS genes alone or in combination with one or more other mvaE and mvaS genes encoding proteins from the upper MVA pathway are contemplated within the scope of the invention. In some embodiments, the mvaE gene encodes a polypeptide that possesses both thiolase and HMG-CoA reductase activities (Hedl, et al., *J. Bacteriol.* 2002 April; 184(8): 2116-2122). The mvaS gene, on the other hand, can encode a polypeptide having an HMG-CoA synthase activity.

Accordingly, recombinant cells (e.g., *E. coli*) can be engineered to express one or more mvaE and mvaS genes to produce isoprene, isoprenoid precursor molecules, and/or isoprenoids. The one or more mvaE and mvaS genes can be expressed on a multicopy plasmid. The plasmid can be a high copy plasmid, a low copy plasmid, or a medium copy plasmid. Alternatively, the one or more mvaE and mvaS genes can be integrated into the host cell's chromosome. For both heterologous expression of the one or more mvaE and mvaS genes on a plasmid or as an integrated part of the host cell's chromosome, expression of the genes can be driven by either an inducible promoter or a constitutively expressing promoter. The promoter can be a strong driver of expression, it can be a weak driver of expression, or it can be a medium driver of expression of the one or more mvaE and mvaS genes.

The mvaE gene encodes a polypeptide that possesses both thiolase and HMG-CoA reductase activities. The thiolase activity of the polypeptide encoded by the mvaE gene converts acetyl Co-A to acetoacetyl CoA whereas the HMG-CoA reductase enzymatic activity of the polypeptide converts 3-hydroxy-3-methylglutaryl-CoA to mevalonate. Exemplary mvaE polypeptides and nucleic acids include naturally-occurring polypeptides and nucleic acids from any of the source organisms described herein as well as mutant polypeptides and nucleic acids derived from any of the source organisms described herein that have at least one activity of a mvaE polypeptide.

Mutant mvaE polypeptides include those in which one or more amino acid residues have undergone an amino acid substitution while retaining mvaE polypeptide activity (i.e., the ability to convert acetyl Co-A to acetoacetyl CoA as well as the ability to convert 3-hydroxy-3-methylglutaryl-CoA to mevalonate). The amino acid substitutions can be conservative or non-conservative and such substituted amino acid residues can or cannot be one encoded by the genetic code. The standard twenty amino acid "alphabet" has been divided into chemical families based on similarity of their side chains. Those families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A "conservative amino acid substitution" is one in which the amino acid residue is replaced with an amino acid residue having a chemically similar side chain (i.e., replacing an amino acid having a basic side chain with another amino acid having a basic side chain). A "non-conservative amino acid substitution" is one in which the amino acid residue is replaced with an amino acid residue having a chemically different side chain (i.e., replacing an amino acid having a basic side chain with another amino acid having an aromatic side chain).

Amino acid substitutions in the mvaE polypeptide can be introduced to improve the functionality of the molecule. For example, amino acid substitutions that increase the binding affinity of the mvaE polypeptide for its substrate, or that improve its ability to convert acetyl Co-A to acetoacetyl CoA and/or the ability to convert 3-hydroxy-3-methylglutaryl-CoA to mevalonate can be introduced into the mvaE polypeptide. In some aspects, the mutant mvaE polypeptides contain one or more conservative amino acid substitutions.

In one aspect, mvaE proteins that are not degraded or less prone to degradation can be used for the production of isoprene. One of skill in the art can express mvaE protein in *E. coli* BL21 (DE3) and look for absence of fragments by any standard molecular biology techniques. For example, absence of fragments can be identified on Safestain stained SDS-PAGE gels following His-tag mediated purification or when expressed in mevalonate, isoprene, isoprenoid precursor molecule, and/or isoprenoid producing *E. coli* BL21 using the methods of detection described herein.

Standard methods, such as those described in Hedl et al., (*J. Bacteriol.* 2002, April; 184(8): 2116-2122) can be used to determine whether a polypeptide has mvaE activity, by measuring acetoacetyl-CoA thiolase as well as HMG-CoA reductase activity. In an exemplary assay, acetoacetyl-CoA thiolase activity is measured by spectrophotometer to monitor the change in absorbance at 302 nm that accompanies the formation or thiolysis of acetoacetyl-CoA. Standard assay conditions for each reaction to determine synthesis of acetoacetyl-CoA, are 1 mM acetyl-CoA, 10 mM $MgCl_2$, 50 mM Tris, pH 10.5 and the reaction is initiated by addition of enzyme. Assays can employ a final volume of 200 µl. For the assay, 1 enzyme unit (eu) represents the synthesis or thiolysis in 1 min of 1 µmol of acetoacetyl-CoA. In another exemplary assay, of HMG-CoA reductase activity can be monitored by spectrophotometer by the appearance or disappearance of NADP(H) at 340 nm. Standard assay conditions for each reaction measured to show reductive deacylation of HMG-CoA to mevalonate are 0.4 mM NADPH, 1.0 mM (R,S)-HMG-CoA, 100 mM KCl, and 100 mM $K_xPO_4$, pH 6.5. Assays employ a final volume of 200 µl. Reactions are initiated by adding the enzyme. For the assay, 1 eu represents the turnover, in 1 min, of 1 µmol of NADP(H). This corresponds to the turnover of 0.5 µmol of HMG-CoA or mevalonate.

Exemplary mvaE nucleic acids include nucleic acids that encode a polypeptide, fragment of a polypeptide, peptide, or fusion polypeptide that has at least one activity of a mvaE polypeptide. Exemplary mvaE polypeptides and nucleic acids include naturally-occurring polypeptides and nucleic acids from any of the source organisms described herein as well as mutant polypeptides and nucleic acids derived from any of the source organisms described herein. Exemplary mvaE nucleic acids include, for example, mvaE nucleic acids isolated from *Listeria grayi*_DSM 20601, *Enterococcus faecium*, *Enterococcus gallinarum* EG2, *Enterococcus faecalis*, and/or *Enterococcus casseliflavus*. The mvaE nucleic acid can be expressed in a recombinant cell on a multicopy plasmid. The plasmid can be a high copy plasmid, a low copy plasmid, or a medium copy plasmid. Alternatively, the mvaE nucleic acid can be integrated into the host cell's chromosome. For both heterologous expression of an mvaE nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaE nucleic acid.

The mvaS gene encodes a polypeptide that possesses HMG-CoA synthase activity. This polypeptide can convert acetoacetyl CoA to 3-hydroxy-3-methylglutaryl-CoA (HMG-CoA). Exemplary mvaS polypeptides and nucleic acids include naturally-occurring polypeptides and nucleic acids from any of the source organisms described herein as well as mutant polypeptides and nucleic acids derived from any of the source organisms described herein that have at least one activity of a mvaS polypeptide.

Mutant mvaS polypeptides include those in which one or more amino acid residues have undergone an amino acid substitution while retaining mvaS polypeptide activity (i.e., the ability to convert acetoacetyl CoA to 3-hydroxy-3-methylglutaryl-CoA). Amino acid substitutions in the mvaS polypeptide can be introduced to improve the functionality of the molecule. For example, amino acid substitutions that increase the binding affinity of the mvaS polypeptide for its substrate, or that improve its ability to convert acetoacetyl CoA to 3-hydroxy-3-methylglutaryl-CoA can be introduced into the mvaS polypeptide. In some aspects, the mutant mvaS polypeptides contain one or more conservative amino acid substitutions.

Standard methods, such as those described in Quant et al. (*Biochem J.*, 1989, 262:159-164), can be used to determine whether a polypeptide has mvaS activity, by measuring HMG-CoA synthase activity. In an exemplary assay, HMG-CoA synthase activity can be assayed by spectrophotometrically measuring the disappearance of the enol form of acetoacetyl-CoA by monitoring the change of absorbance at 303 nm. A standard 1 ml assay system containing 50 mm-Tris/HCl, pH 8.0, 10 mM-MgCl2 and 0.2 mM-dithiothreitol at 30° C.; 5 mM-acetyl phosphate, 10, M-acetoacetyl-CoA and 5 µl samples of extracts can be added, followed by simultaneous addition of acetyl-CoA (100 µM) and 10 units of PTA. HMG-CoA synthase activity is then measured as the difference in the rate before and after acetyl-CoA addition. The absorption coefficient of acetoacetyl-CoA under the conditions used (pH 8.0, 10 mM-$MgCl_2$), is $12.2 \times 10^3$ $M^{-1}$ $cm^{-1}$. By definition, 1 unit of enzyme activity causes 1 µmol of acetoacetyl-CoA to be transformed per minute.

Exemplary mvaS nucleic acids include nucleic acids that encode a polypeptide, fragment of a polypeptide, peptide, or fusion polypeptide that has at least one activity of a mvaS polypeptide. Exemplary mvaS polypeptides and nucleic acids include naturally-occurring polypeptides and nucleic acids from any of the source organisms described herein as well as mutant polypeptides and nucleic acids derived from any of the source organisms described herein. Exemplary mvaS nucleic acids include, for example, mvaS nucleic acids isolated from *Listeria grayi*_DSM 20601, *Enterococcus faecium*, *Enterococcus gallinarum* EG2, *Enterococcus faecalis*, and/or *Enterococcus casseliflavus*.

The mvaS nucleic acid can be expressed in a recombinant cell on a multicopy plasmid. The plasmid can be a high copy plasmid, a low copy plasmid, or a medium copy plasmid. Alternatively, the mvaS nucleic acid can be integrated into the host cell's chromosome. For both heterologous expression of an mvaS nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaS nucleic acid.

Compositions of recombinant cells as described herein are contemplated within the scope of the invention as well. It is understood that recombinant cells also encompass progeny cells as well.

b. Nucleic Acids Encoding Polypeptides of the Lower MVA Pathway

In some aspects of the invention, the cells described in any of the compositions or methods described herein further comprise one or more nucleic acids encoding a lower mevalonate (MVA) pathway polypeptide(s). In some aspects, the lower MVA pathway polypeptide is an endogenous polypeptide. In some aspects, the endogenous nucleic acid encoding a lower MVA pathway polypeptide is operably linked to a constitutive promoter. In some aspects, the endogenous nucleic acid encoding a lower MVA pathway polypeptide is operably linked to an inducible promoter. In some aspects, the endogenous nucleic acid encoding a lower MVA pathway polypeptide is operably linked to a strong promoter. In a particular aspect, the cells are engineered to over-express the endogenous lower MVA pathway polypeptide relative to wild-type cells. In some aspects, the endogenous nucleic acid encoding a lower MVA pathway polypeptide is operably linked to a weak promoter.

The lower mevalonate biosynthetic pathway comprises mevalonate kinase (MVK), phosphomevalonate kinase (PMK), and diphosphomevalonte decarboxylase (MVD). In some aspects, the lower MVA pathway can further comprise isopentenyl diphosphate isomerase (IDI). Cells provided herein can comprise at least one nucleic acid encoding isoprene synthase, one or more upper MVA pathway polypeptides, and/or one or more lower MVA pathway polypeptides. Polypeptides of the lower MVA pathway can be any enzyme (a) that phosphorylates mevalonate to mevalonate 5-phosphate; (b) that converts mevalonate 5-phosphate to mevalonate 5-pyrophosphate; and (c) that converts mevalonate 5-pyrophosphate to isopentenyl pyrophosphate. More particularly, the enzyme that phosphorylates mevalonate to mevalonate 5-phosphate can be from the group consisting of *M. mazei* mevalonate kinase, *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, and *Streptomyces* CL190 mevalonate kinase polypeptide. In another aspect, the enzyme that phosphorylates mevalonate to mevalonate 5-phosphate is *M. mazei* mevalonate kinase.

In some aspects, the lower MVA pathway polypeptide is a heterologous polypeptide. In some aspects, the cells comprise more than one copy of a heterologous nucleic acid encoding a lower MVA pathway polypeptide. In some aspects, the heterologous nucleic acid encoding a lower MVA pathway polypeptide is operably linked to a constitutive promoter. In some aspects, the heterologous nucleic acid encoding a lower MVA pathway polypeptide is operably linked to an inducible promoter. In some aspects, the heterologous nucleic acid encoding a lower MVA pathway polypeptide is operably linked to a strong promoter. In some aspects, the heterologous nucleic acid encoding a lower MVA pathway polypeptide is operably linked to a weak promoter. In some aspects, the heterologous lower MVA pathway polypeptide is a polypeptide from *Saccharomyces cerevisiae*, *Enterococcus faecalis*, or *Methanosarcina mazei*.

The nucleic acids encoding a lower MVA pathway polypeptide(s) can be integrated into a genome of the cells or can be stably expressed in the cells. The nucleic acids encoding a lower MVA pathway polypeptide(s) can additionally be on a vector.

Exemplary lower MVA pathway polypeptides are also provided below: (i) mevalonate kinase (MVK); (ii) phosphomevalonate kinase (PMK); (iii) diphosphomevalonate decarboxylase (MVD); and (iv) isopentenyl diphosphate isomerase (IDI). In particular, the lower MVK polypeptide can be from the genus *Methanosarcina* and, more specifically, the lower MVK polypeptide can be from *Methanosarcina mazei*. Additional examples of lower MVA pathway polypeptides can be found in U.S. Patent Application Publication 2010/0086978 the contents of which are expressly incorporated herein by reference in their entirety with respect to lower MVK pathway polypeptides and lower MVK pathway polypeptide variants.

Any one of the cells described herein can comprise IDI nucleic acid(s) (e.g., endogenous or heterologous nucleic acid(s) encoding IDI). Isopentenyl diphosphate isomerase polypeptides (isopentenyl-diphosphate delta-isomerase or IDI) catalyzes the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Lower MVA pathway polypeptides include polypeptides, fragments of polypeptides, peptides, and fusions polypeptides that have at least one activity of a lower MVA pathway polypeptide. Exemplary lower MVA pathway nucleic acids include nucleic acids that encode a polypeptide, fragment of a polypeptide, peptide, or fusion polypeptide that has at least one activity of a lower MVA pathway polypeptide. Exemplary lower MVA pathway polypeptides and nucleic acids include naturally-occurring polypeptides and nucleic acids from any of the source organisms described herein. In addition, variants of lower MVA pathway polypeptides that confer the result of better isoprene production can also be used as well.

In some aspects, the lower MVA pathway polypeptide is a polypeptide from *Saccharomyces cerevisiae, Enterococcus faecalis*, or *Methanosarcina mazei*. In some aspects, the MVK polypeptide is selected from the group consisting of *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, *Streptomyces* CL190 mevalonate kinase polypeptide, and *Methanosarcina mazei* mevalonate kinase polypeptide. Any one of the promoters described herein (e.g., promoters described herein and identified in the Examples of the present disclosure including inducible promoters and constitutive promoters) can be used to drive expression of any of the MVA polypeptides described herein.

3. DXP Pathway Nucleic Acids and Polypeptides

In some aspects of the invention, the recombinant cells described in any of the compositions or methods described herein further comprise one or more heterologous nucleic acids encoding a DXS polypeptide and/or other DXP pathway polypeptides. In some aspects, the cells further comprise a chromosomal copy of an endogenous nucleic acid encoding a DXS polypeptide and/or other DXP pathway polypeptides. In some aspects, the *E. coli* cells further comprise one or more nucleic acids encoding an IDI polypeptide and a DXS polypeptide and/or other DXP pathway polypeptides. In some aspects, one nucleic acid encodes the isoprene synthase polypeptide, IDI polypeptide, and DXS polypeptide and/or other DXP pathway polypeptides. In some aspects, one plasmid encodes the isoprene synthase polypeptide, IDI polypeptide, and DXS polypeptide and/or other DXP pathway polypeptides. In some aspects, multiple plasmids encode the isoprene synthase polypeptide, IDI polypeptide, and DXS polypeptide or other DXP pathway polypeptides.

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary DXP pathways polypeptides include, but are not limited to any of the following polypeptides: DXS polypeptides, DXR polypeptides, MCT polypeptides, CMK polypeptides, MCS polypeptides, HDS polypeptides, HDR polypeptides, and polypeptides (e.g., fusion polypeptides) having an activity of one, two, or more of the DXP pathway polypeptides. In particular, DXP pathway polypeptides include polypeptides, fragments of polypeptides, peptides, and fusions polypeptides that have at least one activity of a DXP pathway polypeptide. Exemplary DXP pathway nucleic acids include nucleic acids that encode a polypeptide, fragment of a polypeptide, peptide, or fusion polypeptide that has at least one activity of a DXP pathway polypeptide. Exemplary DXP pathway polypeptides and nucleic acids include naturally-occurring polypeptides and nucleic acids from any of the source organisms described herein as well as mutant polypeptides and nucleic acids derived from any of the source organisms described herein. Exemplary DXP pathway polypeptides and nucleic acids and methods of measuring DXP pathway polypeptide activity are described in more detail in International Publication No.: WO 2010/148150

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

In particular, DXS polypeptides convert pyruvate and D-glyceraldehyde 3-phosphate into 1-deoxy-d-xylulose 5-phosphate (DXP). Standard methods can be used to determine whether a polypeptide has DXS polypeptide activity by measuring the ability of the polypeptide to convert pyruvate and D-glyceraldehyde 3-phosphate in vitro, in a cell extract, or in vivo.

DXR polypeptides convert 1-deoxy-d-xylulose 5-phosphate (DXP) into 2-C-methyl-D-erythritol 4-phosphate (MEP). Standard methods can be used to determine whether a polypeptide has DXR polypeptides activity by measuring the ability of the polypeptide to convert DXP in vitro, in a cell extract, or in vivo.

MCT polypeptides convert 2-C-methyl-D-erythritol 4-phosphate (MEP) into 4-(cytidine 5'-diphospho)-2-methyl-D-erythritol (CDP-ME). Standard methods can be used to determine whether a polypeptide has MCT polypeptides activity by measuring the ability of the polypeptide to convert MEP in vitro, in a cell extract, or in vivo.

CMK polypeptides convert 4-(cytidine 5'-diphospho)-2-C-methyl-D-erythritol (CDP-ME) into 2-phospho-4-(cytidine 5'-diphospho)-2-C-methyl-D-erythritol (CDP-MEP). Standard methods can be used to determine whether a polypeptide has CMK polypeptides activity by measuring the ability of the polypeptide to convert CDP-ME in vitro, in a cell extract, or in vivo.

MCS polypeptides convert 2-phospho-4-(cytidine 5'-diphospho)-2-C-methyl-D-erythritol (CDP-MEP) into 2-C-methyl-D-erythritol 2,4-cyclodiphosphate (ME-CPP or cMEPP). Standard methods can be used to determine whether a polypeptide has MCS polypeptides activity by measuring the ability of the polypeptide to convert CDP-MEP in vitro, in a cell extract, or in vivo.

HDS polypeptides convert 2-C-methyl-D-erythritol 2,4-cyclodiphosphate into (E)-4-hydroxy-3-methylbut-2-en-1-yl diphosphate (HMBPP or HDMAPP). Standard methods can be used to determine whether a polypeptide has HDS polypeptides activity by measuring the ability of the polypeptide to convert ME-CPP in vitro, in a cell extract, or in vivo.

HDR polypeptides convert (E)-4-hydroxy-3-methylbut-2-en-1-yl diphosphate into isopentenyl diphosphate (IPP) and dimethylallyl diphosphate (DMAPP). In one embodiment, the ispH gene can be used to encode for HDR polypeptides. IspH is also known as 1-hydroxy-2-methyl-2-(E)-butenyl 4-diphosphate reductase, 4Fe-4S protein, ECK0030, JW0027, lytB, yaaE, and b0029. Standard methods can be used to determine whether a polypeptide has HDR polypeptides activity by measuring the ability of the polypeptide to convert HMBPP in vitro, in a cell extract, or in vivo.

4. Source Organisms for MVA Pathway, Isoprene Synthase, IDI, and DXP Pathway Polypeptides Isoprene synthase, IDI, DXP pathway, and/or MVA pathway nucleic acids can be obtained from any organism that naturally contains isoprene synthase, IDI, DXP pathway, and/or MVA pathway nucleic acids. Isoprene is formed naturally by a variety of organisms, such as bacteria, yeast, plants, and animals. Some organisms contain the MVA pathway for producing isoprene. Isoprene synthase nucleic acids can be obtained, e.g., from any organism that contains an isoprene synthase. MVA pathway nucleic acids can be obtained, e.g., from any organism that contains the MVA pathway. IDI and DXP pathway nucleic acids can be obtained, e.g., from any organism that contains the IDI and DXP pathway.

The nucleic acid sequence of the isoprene synthase, DXP pathway, IDI, and/or MVA pathway nucleic acids can be isolated from a bacterium, fungus, plant, algae, or cyanobacterium. Exemplary source organisms include, for example, yeasts, such as species of *Saccharomyces* (e.g., *S. cerevisiae*), bacteria, such as species of *Escherichia* (e.g., *E. coli*), or species of *Methanosarcina* (e.g., *Methanosarcina mazei*), plants, such as kudzu or poplar (e.g., *Populus alba* or *Populus alba×tremula* CAC35696) or aspen (e.g., *Populus tremuloides*). Exemplary sources for isoprene synthases, IDI, and/or MVA pathway polypeptides which can be used are also described in International Patent Application Publication Nos. WO2009/076676, WO2010/003007, WO2009/132220, WO2010/031062, WO2010/031068, WO2010/031076, WO2010/013077, WO2010/031079, WO2010/148150, WO2010/078457, and WO2010/148256.

In some aspects, the source organism is a yeast, such as *Saccharomyces* sp., *Schizosaccharomyces* sp., *Pichia* sp., or *Candida* sp.

In some aspects, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, strains of *Escherichia* such as *E. coli*, strains of *Enterobacter*, strains of *Streptococcus*, or strains of *Archaea* such as *Methanosarcina mazei*.

As used herein, "the genus *Bacillus*" includes all species within the genus "*Bacillus*," as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus*, *Amphibacillus*, *Aneurinibacillus*, *Anoxybacillus*, *Brevibacillus*, *Filobacillus*, *Gracilibacillus*, *Halobacillus*, *Paenibacillus*, *Salibacillus*, *Thermobacillus*, *Ureibacillus*, and *Virgibacillus*.

In some aspects, the source organism is a gram-positive bacterium. Non-limiting examples include strains of *Streptomyces* (e.g., *S. lividans*, *S. coelicolor*, or *S. griseus*) and *Bacillus*. In some aspects, the source organism is a gram-negative bacterium, such as *E. coli* or *Pseudomonas* sp. In some aspects, the source organism is *L. acidophilus*.

In some aspects, the source organism is a plant, such as a plant from the family Fabaceae, such as the Faboideae subfamily. In some aspects, the source organism is kudzu, poplar (such as *Populus alba×tremula* CAC35696), aspen (such as *Populus tremuloides*), or *Quercus robur*.

In some aspects, the source organism is an algae, such as a green algae, red algae, glaucophytes, chlorarachniophytes, euglenids, chromista, or dinoflagellates.

In some aspects, the source organism is a cyanobacteria, such as cyanobacteria classified into any of the following groups based on morphology: *Chroococcales*, *Pleurocapsales*, *Oscillatoriales*, *Nostocales*, or *Stigonematales*.

5. Phosphoketolase Nucleic Acids and Polypeptides

In some aspects of the invention, the recombinant cells described in any of the compositions or methods described herein further comprise one or more nucleic acids encoding a phosphoketolase polypeptide or a polypeptide having phosphoketolase activity. In some aspects, the phosphoketolase polypeptide is an endogenous polypeptide. In some aspects, the endogenous nucleic acid encoding a phosphoketolase polypeptide is operably linked to a constitutive promoter. In some aspects, the endogenous nucleic acid encoding a phosphoketolase polypeptide is operably linked to an inducible promoter. In some aspects, the endogenous nucleic acid encoding a phosphoketolase polypeptide is operably linked to a strong promoter. In some aspects, more than one endogenous nucleic acid encoding a phosphoketolase polypeptide is used (e.g, 2, 3, 4, or more copies of an endogenous nucleic acid encoding a phosphoketolase polypeptide). In a particular aspect, the cells are engineered to overexpress the endogenous phosphoketolase polypeptide relative to wild-type cells. In some aspects, the endogenous nucleic acid encoding a phosphoketolase polypeptide is operably linked to a weak promoter.

Phosphoketolase enzymes catalyze the conversion of xylulose 5-phosphate to glyceraldehyde 3-phosphate and acetyl phosphate and/or the conversion of fructose 6-phosphate to erythrose 4-phosphate and acetyl phosphate. In certain embodiments, the phosphoketolase enzyme is capable of catalyzing the conversion of xylulose 5-phosphate to glyceraldehyde 3-phosphate and acetyl phosphate. In other embodiments, the phosphoketolase enzyme is capable of catalyzing the conversion of fructose 6-phosphate to erythrose 4-phosphate and acetyl phosphate. Thus, without being bound by theory, the expression of phosphoketolase as set forth herein can result in an increase in the amount of acetyl phosphate produced from a carbohydrate source. This acetyl phosphate can be converted into acetyl-CoA which can then be utilized by the enzymatic activities of the MVA pathway to produces mevalonate, isoprenoid precursor molecules, isoprene and/or isoprenoids. Thus the amount of these compounds produced from a carbohydrate substrate may be increased. Alternatively, production of Acetyl-P and AcCoA can be increased without the increase being reflected in higher intracellular concentration. In certain embodiments, intracellular acetyl-P or acetyl-CoA concentrations will remain unchanged or even decrease, even though the phosphoketolase reaction is taking place.

Exemplary phosphoketolase nucleic acids include nucleic acids that encode a polypeptide, fragment of a polypeptide, peptide, or fusion polypeptide that has at least one activity of a phosphoketolase polypeptide. Exemplary phosphoketolase polypeptides and nucleic acids include naturally-occurring polypeptides and nucleic acids from any of the source organisms described herein as well as mutant polypeptides and nucleic acids derived from any of the source organisms described herein.

Standard methods can be used to determine whether a polypeptide has phosphoketolase peptide activity by measuring the ability of the peptide to convert D-fructose 6-phosphate or D-xylulose 5-phosphate into acetyl-P. Acetyl-P can then be converted into ferryl acetyl hydroxamate, which can be detected spectrophotometrically (Meile et al., J. Bact. 183: 2929-2936, 2001). Any polypeptide identified as having phosphoketolase peptide activity as described herein is suitable for use in the present invention.

In other aspects, exemplary phosphoketolase nucleic acids include, for example, a phosphoketolase isolated from *Lactobacillus reuteri*, *Bifidobacterium longum*, *Ferrimonas balearica*, *Pedobactor saltans*, *Streptomyces griseus*, and/or *Nocardiopsis dassonvillei*. Additional examples of phosphoketolase enzymes which can be used herein are described in U.S. Pat. No. 7,785,858, which is incorporated by reference herein.

a. Pathways Involving the Entner-Doudoroff Pathway

The Entner-Doudoroff (ED) pathway is an alternative to the Emden-Meyerhoff-Parnass (EMP-glycolysis) pathway. Some organisms, like *E. coli*, harbor both the ED and EMP pathways, while others have only one or the other. *Bacillus subtilis* has only the EMP pathway, while *Zymomonas mobilis* has only the ED pathway (Peekhaus and Conway. 1998. J. Bact. 180:3495-3502; Stulke and Hillen. 2000. Annu. Rev. Microbiol. 54, 849-880; Dawes et al. 1966. Biochem. J. 98:795-803).

Phosphogluconate dehydratase (edd) removes one molecule of $H_2O$ from 6-phospho-D-gluconate to form 2-dehydro-3-deoxy-D-gluconate 6-phosphate, while 2-keto-3-deoxygluconate 6-phosphate aldolase (eda) catalyzes an aldol cleavage (Egan et al. 1992. J. Bact. 174:4638-4646). The two genes are in an operon.

Metabolites that can be directed into the phosphoketolase pathway can also be diverted into the ED pathway. To avoid metabolite loss to the ED-pathway, phosphogluconate dehydratase gene (e.g., the endogenous phosphogluconate dehydratase gene) and/or an 2-keto-3-deoxygluconate 6-phosphate aldolase gene (e.g., the endogenous 2-keto-3-deoxygluconate 6-phosphate aldolase gene) activity is attenuated. One way of achieving attenuation is by deleting phosphogluconate dehydratase (edd) and/or 2-keto-3-deoxygluconate 6-phosphate aldolase (eda). This can be accomplished by replacing one or both genes with a chloramphenicol or kanamycin cassette followed by looping out of the cassette. Without these enzymatic activities, more carbon can flux through the phosphoketolase enzyme, thus increasing the yield of mevalonate, isoprene, isoprenoid precursor molecules, and/or isoprenoids.

The activity of phosphogluconate dehydratase (edd) and/or 2-keto-3-deoxygluconate 6-phosphate aldolase (eda) can also be decreased by other molecular manipulations of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

In some cases, attenuating the activity of the endogenous phosphogluconate dehydratase gene and/or the endogenous 2-keto-3-deoxygluconate 6-phosphate aldolase gene results in more carbon flux into the mevalonate dependent biosynthetic pathway in comparison to cells that do not have attenuated endogenous phosphogluconate dehydratase gene and/or endogenous acetate kinase2-keto-3-deoxygluconate 6-phosphate aldolase gene expression.

b. Pathways Involving the Oxidative Branch of the Pentose Phosphate Pathway

E. coli uses the pentose phosphate pathway to break down hexoses and pentoses and to provide cells with intermediates for various anabolic pathways. It is also a major producer of NADPH. The pentose phosphate pathway is composed from an oxidative branch (with enzymes like glucose 6-phosphate 1-dehydrogenase (zwf), 6-phosphogluconolactonase (pgl) or 6-phosphogluconate dehydrogenase (gnd)) and a non-oxidative branch (with enzymes such as transketolase (tktA), transaldolase (talA or talB), ribulose-5-phosphate-epimerase and (or) ribose-5-phosphate epimerase) (Sprenger. 1995. Arch. Microbiol. 164:324-330).

In order to direct carbon towards the phosphoketolase enzyme, the non-oxidative branch of the pentose phosphate pathway (transketolase, transaldolase, ribulose-5-phosphate-epimerase and (or) ribose-5-phosphate epimerase) expression can be modulated (e.g., increase enzyme activity) to allow more carbon to flux towards fructose 6-phosphate and xylulose 5-phosphate, thereby increasing the eventual production of mevalonate, isoprene, isoprenoid precursor molecules, and/or isoprenoids. Increase of transketolase, transaldolase, ribulose-5-phosphate-epimerase and (or) ribose-5-phosphate epimerase activity can be any amount of increase of specific activity or total activity as compared to when no manipulation has been effectuated. In some instances, the enzyme activity is increased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%, or 100%. In some aspects, the activity of transketolase, transaldolase, ribulose-5-phosphate-epimerase and (or) ribose-5-phosphate epimerase is modulated by increasing the activity of an endogenous transketolase, transaldolase, ribulose-5-phosphate-epimerase and (or) ribose-5-phosphate epimerase. This can be accomplished by replacing the endogenous transketolase, transaldolase, ribulose-5-phosphate-epimerase and (or) ribose-5-phosphate epimerase gene promoter with a synthetic constitutively high expressing promoter. The genes encoding transketolase, transaldolase, ribulose-5-phosphate-epimerase and (or) ribose-5-phosphate epimerase can also be cloned on a plasmid behind an appropriate promoter. The increase of the activity of transketolase, transaldolase, ribulose-5-phosphate-epimerase and (or) ribose-5-phosphate epimerase can result in more carbon flux into the mevalonate dependent biosynthetic pathway in comparison to cells that do not have increased expression of transketolase, transaldolase, ribulose-5-phosphate-epimerase and (or) ribose-5-phosphate epimerase.

c. Pathways Involving Phosphofructokinase

Phosphofructokinase is a crucial enzyme of glycolysis which catalyzes the phosphorylation of fructose 6-phosphate. E. coli has two isozymes encoded by pfkA and pfkB. Most of the phosphofructokinase activity in the cell is due to pfkA (Kotlarz et al. 1975 Biochim. Biophys. Acta 381:257-268).

In order to direct carbon towards the phosphoketolase enzyme, phosphofructokinase expression can be modulated (e.g., decrease enzyme activity) to allow more carbon to flux towards fructose 6-phosphate and xylulose 5-phosphate, thereby increasing the eventual production of mevalonate, isoprene, isoprenoid precursor molecules, and/or isoprenoids. Decrease of phosphofructokinase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%. Or 100%. In some aspects, the activity of phosphofructokinase is modulated by decreasing the activity of an endogenous phosphofructokinase. This can be accomplished by replacing the endogenous phosphofructokinase gene promoter with a synthetic constitutively low expressing promoter. The gene encoding phosphofructokinase can also be deleted. The decrease of the activity of phosphofructokinase can result in more carbon flux into the mevalonate dependent biosynthetic pathway in comparison to cells that do not have decreased expression of phosphofructokinase.

6. Additional Host Cell Mutations

The invention also contemplates additional host cell mutations that increase carbon flux through the MVA pathway. By increasing the carbon flow, more isoprene can be produced. The recombinant cells comprising acetoacetyl-CoA synthase as described herein can also be engineered for increased carbon flux towards mevalonate production wherein the activity of one or more enzymes from the group consisting of: (a) citrate synthase, (b) phosphotransacetylase; (c) acetate kinase; (d) lactate dehydrogenase; (e) NADP-dependent malic enzyme, and; (f) pyruvate dehydrogenase is modulated.

a. Citrate Synthase Pathway

Figure 5:
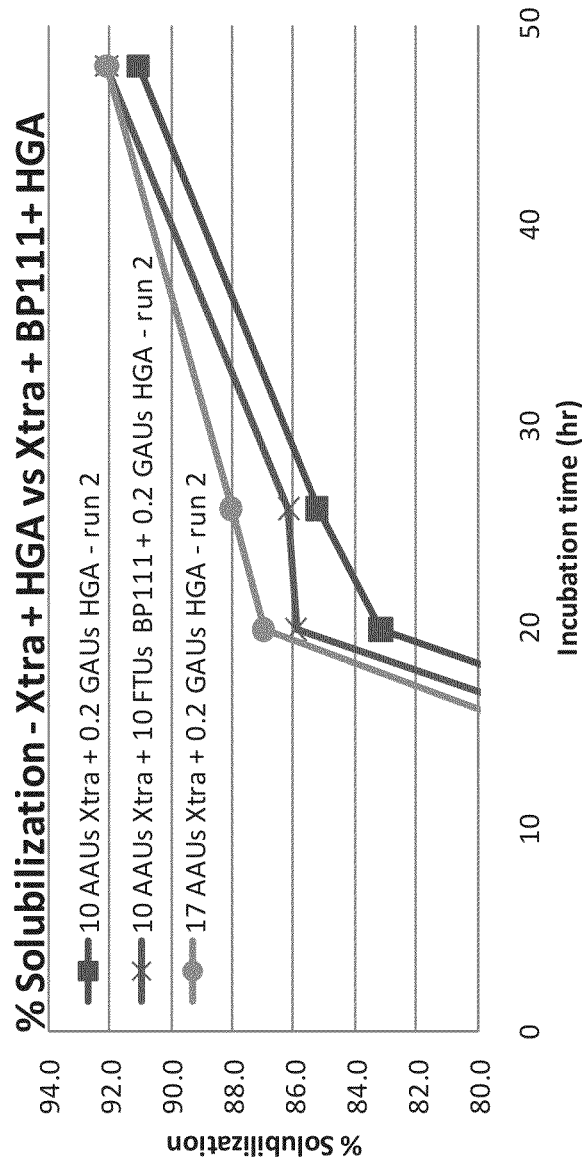
FIG. 5 depicts a zoomed-in view of FIG. 4.

Citrate synthase catalyzes the condensation of oxaloacetate and acetyl-CoA to form citrate, a metabolite of the Tricarboxylic acid (TCA) cycle (Ner, S. et al. 1983. Biochemistry 22: 5243-5249; Bhayana, V. and Duckworth, H.1984. Biochemistry 23: 2900-2905) (FIG. 5). In E. coli, this enzyme, encoded by gltA, behaves like a trimer of dimeric subunits. The hexameric form allows the enzyme to be allosterically regulated by NADH. This enzyme has been widely studied (Wiegand, G., and Remington, S. 1986. Annual Rev. Biophysics Biophys. Chem. 15: 97-117; Duckworth et al. 1987. Biochem Soc Symp. 54:83-92; Stockell, D. et al. 2003. J. Biol. Chem. 278: 35435-43; Maurus, R. et al. 2003. Biochemistry. 42:5555-5565). To avoid allosteric inhibition by NADH, replacement by or supplementation with the *Bacillus subtilis* NADH-insensitive citrate synthase has been considered (Underwood et al. 2002. Appl. Environ. Microbiol. 68:1071-1081; Sanchez et al. 2005. Met. Eng. 7:229-239).

The reaction catalyzed by citrate synthase is directly competing with the thiolase catalyzing the first step of the mevalonate pathway, as they both have acetyl-CoA as a substrate (Hedl et al. 2002. J. Bact. 184:2116-2122). Therefore, one of skill in the art can modulate citrate synthase expression (e.g., decrease enzyme activity) to allow more carbon to flux into the mevalonate pathway, thereby increasing the eventual production of mevalonate and isoprene. Decrease of citrate synthase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In some aspects, the activity of citrate synthase is modulated by decreasing the activity of an endogenous citrate synthase gene. This can be accomplished by chromosomal replacement of an endogenous citrate synthase gene with a transgene encoding an NADH-insensitive citrate synthase or by using a transgene encoding an NADH-insensitive citrate synthase that is derived from *Bacillus subtilis*. The activity of citrate synthase can also be modulated (e.g., decreased) by replacing the endogenous citrate synthase gene promoter with a synthetic constitutively low expressing promoter. The decrease of the activity of citrate synthase can result in more carbon flux into the mevalonate dependent biosynthetic pathway in comparison to microorganisms that do not have decreased expression of citrate synthase.

b. Pathways Involving Phosphotransacetylase and/or Acetate Kinase

Phosphotransacetylase (pta) (Shimizu et al. 1969. Biochim. Biophys. Acta 191: 550-558) catalyzes the reversible conversion between acetyl-CoA and acetylphosphate (acetyl-P), while acetate kinase (ackA) (Kakuda, H. et al. 1994. J. Biochem. 11:916-922) uses acetyl-P to form acetate. These genes can be transcribed as an operon in *E. coli*. Together, they catalyze the dissimilation of acetate, with the release of ATP. Thus, one of skill in the art can increase the amount of available acetyl Co-A by attenuating the activity of phosphotransacetylase gene (e.g., the endogenous phosphotransacetylase gene) and/or an acetate kinase gene (e.g., the endogenous acetate kinase gene). One way of achieving attenuation is by deleting phosphotransacetylase (pta) and/or acetate kinase (ackA). This can be accomplished by replacing one or both genes with a chloramphenicol cassette followed by looping out of the cassette. Acetate is produced by *E. coli* for a variety of reasons (Wolfe, A. 2005. Microb. Mol. Biol. Rev. 69:12-50). Without being bound by theory, since ackA-pta use acetyl-CoA, deleting those genes might allow carbon not to be diverted into acetate and to increase the yield of mevalonate and/or isoprene.

In some aspects, the recombinant microorganism produces decreased amounts of acetate in comparison to microorganisms that do not have attenuated endogenous phosphotransacetylase gene and/or endogenous acetate kinase gene expression. Decrease in the amount of acetate produced can be measured by routine assays known to one of skill in the art. The amount of acetate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of phosphotransacetylase (pta) and/or acetate kinase (ackA) can also be decreased by other molecular manipulation of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

In some cases, attenuating the activity of the endogenous phosphotransacetylase gene and/or the endogenous acetate kinase gene results in more carbon flux into the mevalonate dependent biosynthetic pathway in comparison to microorganisms that do not have attenuated endogenous phosphotransacetylase gene and/or endogenous acetate kinase gene expression.

c. Pathways Involving Lactate Dehydrogenase

In *E. coli*, D-Lactate is produced from pyruvate through the enzyme lactate dehydrogenase (ldhA—FIG. 5) (Bunch, P. et al. 1997. Microbiol. 143:187-195). Production of lactate is accompanied with oxidation of NADH, hence lactate is produced when oxygen is limited and cannot accommodate all the reducing equivalents. Thus, production of lactate could be a source for carbon consumption. As such, to improve carbon flow through to mevalonate production (and isoprene production, if desired), one of skill in the art can modulate the activity of lactate dehydrogenase, such as by decreasing the activity of the enzyme.

Accordingly, in one aspect, the activity of lactate dehydrogenase can be modulated by attenuating the activity of an endogenous lactate dehydrogenase gene. Such attenuation can be achieved by deletion of the endogenous lactate dehydrogenase gene. Other ways of attenuating the activity of lactate dehydrogenase gene known to one of skill in the art may also be used. By manipulating the pathway that involves lactate dehydrogenase, the recombinant microorganism produces decreased amounts of lactate in comparison to microorganisms that do not have attenuated endogenous lactate dehydrogenase gene expression. Decrease in the amount of lactate produced can be measured by routine assays known to one of skill in the art. The amount of lactate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of lactate dehydrogenase can also be decreased by other molecular manipulations of the enzyme. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

Accordingly, in some cases, attenuation of the activity of the endogenous lactate dehydrogenase gene results in more carbon flux into the mevalonate dependent biosynthetic pathway in comparison to microorganisms that do not have attenuated endogenous lactate dehydrogenase gene expression.

d. Pathways Involving Malic Enzyme

Malic enzyme (in *E. coli* sfcA and maeB) is an anaplerotic enzyme that catalyzes the conversion of malate into pyruvate (using NAD+ or NADP+) by the equation below:

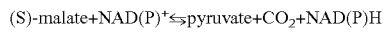
(S)-malate+NAD(P)⁺ ⇌ pyruvate+CO₂+NAD(P)H

Thus, the two substrates of this enzyme are (S)-malate and NAD(P)⁺, whereas its 3 products are pyruvate, CO₂, and NADPH.

Expression of the NADP-dependent malic enzyme (maeB—FIG. 5) (Iwikura, M. et al. 1979. *J. Biochem.* 85: 1355-1365) can help increase mevalonate and/or isoprene yield by 1) bringing carbon from the TCA cycle back to pyruvate, direct precursor of acetyl-CoA, itself direct precursor of the mevalonate pathway and 2) producing extra NADPH which could be used in the HMG-CoA reductase reaction (Oh, M K et al. (2002) *J. Biol. Chem.* 277: 13175-13183; Bologna, F. et al. (2007) *J. Bact.* 189:5937-5946).

As such, more starting substrate (pyruvate or acetyl-CoA) for the downstream production of mevalonate and/or isoprene can be achieved by modulating, such as increasing, the activity and/or expression of malic enzyme. The NADP-dependent malic enzyme gene can be an endogenous gene. One non-limiting way to accomplish this is by replacing the endogenous NADP-dependent malic enzyme gene promoter with a synthetic constitutively expressing promoter. Another non-limiting way to increase enzyme activity is by using one or more heterologous nucleic acids encoding an NADP-dependent malic enzyme polypeptide. One of skill in the art can monitor the expression of maeB RNA during fermentation or culturing using readily available molecular biology techniques.

Accordingly, in some embodiments, the recombinant microorganism produces increased amounts of pyruvate in comparison to microorganisms that do not have increased expression of an NADP-dependent malic enzyme gene. In some aspects, increasing the activity of an NADP-dependent malic enzyme gene results in more carbon flux into the mevalonate dependent biosynthetic pathway in comparison to microorganisms that do not have increased NADP-dependent malic enzyme gene expression.

Increase in the amount of pyruvate produced can be measured by routine assays known to one of skill in the art. The amount of pyruvate increase can be at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of malic enzyme can also be increased by other molecular manipulations of the enzyme. The increase of enzyme activity can be any amount of increase of specific activity or total activity as compared to when no manipulation has been effectuated. In some instances, the increase of enzyme activity is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

e. Pathways Involving Pyruvate Dehydrogenase Complex

The pyruvate dehydrogenase complex, which catalyzes the decarboxylation of pyruvate into acetyl-CoA, is composed of the proteins encoded by the genes aceE, aceF and lpdA. Transcription of those genes is regulated by several regulators. Thus, one of skill in the art can increase acetyl-CoA by modulating the activity of the pyruvate dehydrogenase complex. Modulation can be to increase the activity and/or expression (e.g., constant expression) of the pyruvate dehydrogenase complex. This can be accomplished by different ways, for example, by placing a strong constitutive promoter, like PL.6 (aattcatataaaaaacatacagataac-catctgcggtgataaattatctctggcg-gtgttgacataaataccactggcggtgatactgagcacatca gcaggacgcact-gaccaccatgaaggtg—lambda promoter, GenBank NC_001416 (SEQ ID NO:2)), in front of the operon or using one or more synthetic constitutively expressing promoters.

Accordingly, in one aspect, the activity of pyruvate dehydrogenase is modulated by increasing the activity of one or more genes of the pyruvate dehydrogenase complex consisting of (a) pyruvate dehydrogenase (E1), (b) dihydrolipoyl transacetylase, and (c) dihydrolipoyl dehydrogenase. It is understood that any one, two or three of these genes can be manipulated for increasing activity of pyruvate dehydrogenase. In another aspect, the activity of the pyruvate dehydrogenase complex can be modulated by attenuating the activity of an endogenous pyruvate dehydrogenase complex repressor gene, further detailed below. The activity of an endogenous pyruvate dehydrogenase complex repressor can be attenuated by deletion of the endogenous pyruvate dehydrogenase complex repressor gene.

In some cases, one or more genes of the pyruvate dehydrogenase complex are endogenous genes. Another way to increase the activity of the pyruvate dehydrogenase complex is by introducing into the microorganism one or more heterologous nucleic acids encoding one or more polypeptides from the group consisting of (a) pyruvate dehydrogenase (E1), (b) dihydrolipoyl transacetylase, and (c) dihydrolipoyl dehydrogenase.

By using any of these methods, the recombinant microorganism can produce increased amounts of acetyl Co-A in comparison to microorganisms wherein the activity of pyruvate dehydrogenase is not modulated. Modulating the activity of pyruvate dehydrogenase can result in more carbon flux into the mevalonate dependent biosynthetic pathway in comparison to microorganisms that do not have modulated pyruvate dehydrogenase expression.

f. Combinations of Mutations

It is understood that for any of the enzymes and/or enzyme pathways described herein, molecular manipulations that modulate any combination (two, three, four, five or six) of the enzymes and/or enzyme pathways described herein is expressly contemplated. For ease of the recitation of the combinations, citrate synthase (gltA) is designated as A, phosphotransacetylase (ptaB) is designated as B, acetate kinase (ackA) is designated as C, lactate dehydrogenase (ldhA) is designated as D, malic enzyme (sfcA or maeB) is designated as E, and pyruvate decarboxylase (aceE, aceF, and/or lpdA) is designated as F. As discussed above, aceE, aceF, and/or lpdA enzymes of the pyruvate decarboxylase complex can be used singly, or two of three enzymes, or three of three enzymes for increasing pyruvate decarboxylase activity.

Accordingly, for combinations of any two of the enzymes A-F, non-limiting combinations that can be used are: AB, AC, AD, AE, AF, BC, BD, BE, BF, CD, CE, CF, DE, DF and EF. For combinations of any three of the enzymes A-F, non-limiting combinations that can be used are: ABC, ABD, ABE, ABF, BCD, BCE, BCF, CDE, CDF, DEF, ACD, ACE, ACF, ADE, ADF, AEF, BDE, BDF, BEF, and CEF. For combinations of any four of the enzymes A-F, non-limiting combinations that can be used are: ABCD, ABCE, ABCF, ABDE, ABDF, ABEF, BCDE, BCDF, CDEF, ACDE, ACDF, ACEF, BCEF, BDEF, and ADEF. For combinations of any five of the enzymes A-F, non-limiting combinations that can be used are: ABCDE, ABCDF, ABDEF, BCDEF, ACDEF, and ABCEF. In another aspect, all six enzyme combinations are used: ABCDEF.

Accordingly, the recombinant microorganism as described herein can achieve increased mevalonate production that is increased compared to microorganisms that are not grown under conditions of tri-carboxylic acid (TCA) cycle activity, wherein metabolic carbon flux in the recombinant microorganism is directed towards mevalonate production by modulating the activity of one or more enzymes from the group consisting of (a) citrate synthase, (b) phosphotransacetylase and/or acetate kinase, (c) lactate dehydrogenase, (d) malic enzyme, and (e) pyruvate decarboxylase complex.

7. Other Regulators and Factors for Increased Isoprene Production

Other molecular manipulations can be used to increase the flow of carbon towards isoprene production. One method is to reduce, decrease or eliminate the effects of negative regulators for pathways that feed into the mevalonate pathway. For example, in some cases, the genes aceEF-lpdA are in an operon, with a fourth gene upstream pdhR. pdhR is a negative regulator of the transcription of its operon. In the absence of pyruvate, it binds its target promoter and represses transcription. It also regulates ndh and cyoABCD in the same way (Ogasawara, H. et al. 2007. J. Bact. 189:5534-5541). In one aspect, deletion of pdhR regulator can improve the supply of pyruvate, and hence the production mevalonate and/or isoprene.

In other aspects, the introduction of 6-phosphogluconolactonase (PGL) into microorganisms (such as various *E. coli* strains) which lack PGL can be used to improve production of mevalonate and/or isoprene. PGL may be introduced using chromosomal integration or extra-chromosomal vehicles, such as plasmids. In other aspects, PGL may be deleted from the genome of microorganisms (such as various *E. coli* strains) which express an endogenous PGL to improve production of mevalonate and/or isoprene. In some aspects, deletion of PGL results in any of about 10%, 20%, 30%, 40%, 50%, 60%, 70%, 80%, 90%, or 100%, inclusive, including any values in between these percentages, higher percent yield of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher instantaneous percent yield of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher cell productivity index for isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher volumetric productivity of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher peak specific productivity of isoprene in comparison to microorganisms that express PGL. In some aspects the deletion of PGL results in peak specific productivity being maintained for a longer period of time in comparison to microorganisms that express PGL.

8. Polyprenyl Pyrophosphate Synthase Nucleic Acids and Polypeptides

In some aspects of the invention, the cells described in any of the compositions or methods herein further comprise one or more nucleic acids encoding a polyprenyl pyrophosphate synthase polypeptides(s). The polyprenyl pyrophosphate synthase polypeptide can be an endogenous polypeptide. The endogenous nucleic acid encoding a polyprenyl pyrophosphate synthase polypeptide can be operably linked to a constitutive promoter or can similarly be operably linked to an inducible promoter. The endogenous nucleic acid encoding a polyprenyl pyrophosphate synthase polypeptide can additionally be operably linked to a strong promoter. Alternatively, the endogenous nucleic acid encoding a polyprenyl pyrophosphate synthase polypeptide can be operably linked to a weak promoter. In particular, the cells can be engineered to over-express the endogenous polyprenyl pyrophosphate synthase polypeptide relative to wild-type cells.

In some aspects, the polyprenyl pyrophosphate synthase polypeptide is a heterologous polypeptide. The cells of the present invention can comprise more than one copy of a heterologous nucleic acid encoding a polyprenyl pyrophosphate synthase polypeptide. In some aspects, the heterologous nucleic acid encoding a polyprenyl pyrophosphate synthase polypeptide is operably linked to a constitutive promoter. In some aspects, the heterologous nucleic acid encoding a polyprenyl pyrophosphate synthase polypeptide is operably linked to an inducible promoter. In some aspects, the heterologous nucleic acid encoding a polyprenyl pyrophosphate synthase polypeptide is operably linked to a strong promoter. In some aspects, the heterologous nucleic acid encoding a polyprenyl pyrophosphate synthase polypeptide is operably linked to a weak promoter.

The nucleic acids encoding a polyprenyl pyrophosphate synthase polypeptide(s) can be integrated into a genome of the host cells or can be stably expressed in the cells. The nucleic acids encoding a polyprenyl pyrophosphate synthase polypeptide(s) can additionally be on a vector.

Exemplary polyprenyl pyrophosphate synthase nucleic acids include nucleic acids that encode a polypeptide, fragment of a polypeptide, peptide, or fusion polypeptide that has at least one activity of a polyprenyl pyrophosphate synthase. Polyprenyl pyrophosphate synthase polypeptides convert isoprenoid precursor molecules into more complex isoprenoid compounds. Exemplary polyprenyl pyrophosphate synthase polypeptides include polypeptides, fragments of polypeptides, peptides, and fusions polypeptides that have at least one activity of an isoprene synthase polypeptide. Exemplary polyprenyl pyrophosphate synthase polypeptides and nucleic acids include naturally-occurring polypeptides and nucleic acids from any of the source organisms described herein. In addition, variants of polyprenyl pyrophosphate synthase can possess improved activity such as improved enzymatic activity. In some aspects, a polyprenyl pyrophosphate synthase variant has other improved properties, such as improved stability (e.g., thermo-stability), and/or improved solubility. Exemplary polyprenyl pyrophosphate synthase nucleic acids can include nucleic acids which encode polyprenyl pyrophosphate synthase polypeptides such as, without limitation, geranyl diphosposphate (GPP) synthase, farnesyl pyrophosphate (FPP) synthase, and geranylgeranyl pyrophosphate (GGPP) synthase, or any other known polyprenyl pyrophosphate synthase polypeptide.

In some aspects of the invention, the cells described in any of the compositions or methods herein further comprise one or more nucleic acids encoding a farnesyl pyrophosphate (FPP) synthase. The FPP synthase polypeptide can be an endogenous polypeptide encoded by an endogenous gene. In some aspects, the FPP synthase polypeptide is encoded by an endogenous ispA gene in *E. coli*. The endogenous nucleic acid encoding an FPP synthase polypeptide can be operably linked to a constitutive promoter or can similarly be operably linked to an inducible promoter. The endogenous nucleic acid encoding an FPP synthase polypeptide can additionally be operably linked to a strong promoter. In particular, the cells can be engineered to over-express the endogenous FPP synthase polypeptide relative to wild-type cells. In some aspects, the FPP synthase polypeptide is a heterologous polypeptide. The cells of the present invention can comprise more than one copy of a heterologous nucleic acid encoding a FPP synthase polypeptide. In some aspects, the heterologous nucleic acid encoding a FPP synthase polypeptide is operably linked to a constitutive promoter. In some aspects, the heterologous nucleic acid encoding a FPP synthase polypeptide is operably linked to an inducible promoter. In some aspects, the heterologous nucleic acid encoding a polyprenyl pyrophosphate synthase polypeptide is operably linked to a strong promoter.

The nucleic acids encoding an FPP synthase polypeptide can be integrated into a genome of the host cells or can be stably expressed in the cells. The nucleic acids encoding an FPP synthase can additionally be on a vector.

Standard methods can be used to determine whether a polypeptide has polyprenyl pyrophosphate synthase polypeptide activity by measuring the ability of the polypeptide to convert IPP into higher order isoprenoids in vitro, in a cell extract, or in vivo. These methods are well known in the art and are described, for example, in U.S. Pat. No. 7,915,026; Hsieh et al., *Plant Physiol.* 2011 March; 155(3): 1079-90; Danner et al., *Phytochemistry.* 2011 Apr. 12 [Epub ahead of print]; Jones et al., *J. Biol. Chem.* 2011 Mar. 24 [Epub ahead of print]; Keeling et al., *BMC Plant Biol.* 2011 Mar. 7; 11:43; Martin et al., *BMC Plant Biol.* 2010 Oct. 21; 10:226; Kumeta & Ito, *Plant Physiol.* 2010 December; 154(4):1998-2007; and Köllner & Boland, *J Org. Chem.* 2010 Aug. 20; 75(16):5590-600.

9. Vectors

Suitable vectors can be used for any of the compositions and methods described herein. For example, suitable vectors can be used to optimize the expression of one or more copies of a gene encoding an isoprene synthase, an acetoacetyl co-A synthase, an MVA pathway enzyme, a DXP pathway enzyme, a phosphoketolase, and/or a polyprenyl pyrophosphate synthase, in a cell. In some aspects, the vector contains a selective marker. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. In some aspects, one or more copies of an isoprene synthase, an acetoacetyl co-A synthase, an MVA pathway enzyme, a DXP pathway enzyme, a phosphoketolase, and/or a polyprenyl pyrophosphate synthases nucleic acid(s) integrate into the genome of host cells without a selective marker.

Any one of the vectors characterized or used in the Examples of the present disclosure can be used.

10. Exemplary Host Cells

One of skill in the art will recognize that expression vectors are designed to contain certain components which optimize gene expression for certain host strains. Such optimization components include, but are not limited to origin of replication, promoters, and enhancers. The vectors and components referenced herein are described for exemplary purposes and are not meant to narrow the scope of the invention.

Any microorganism or progeny thereof that can be used to heterologously express genes can be used to express one or more copies of a nucleic acid encoding an isoprene synthase, acetoacetyl co-A synthase, MVA pathway enzyme, DXP pathway enzyme, phosphoketolase, and/or a polyprenyl pyrophosphate synthase polypeptides in a cell. Bacteria cells, including gram positive or gram negative bacteria can be used to express any of the nucleic acids or polypeptides described above. In particular, one or more copies of a nucleic acid encoding an isoprene synthase, acetoacetyl co-A synthase, MVA pathway enzyme, DXP pathway enzyme, phosphoketolase, and/or a polyprenyl pyrophosphate synthase polypeptides can be expressed in any one of *P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells.

There are numerous types of anaerobic cells that can be used as host cells in the compositions and methods of the present invention. In one aspect of the invention, the cells described in any of the compositions or methods described herein are obligate anaerobic cells and progeny thereof. Obligate anaerobes typically do not grow well, if at all, in conditions where oxygen is present. It is to be understood that a small amount of oxygen may be present, that is, there is some tolerance level that obligate anaerobes have for a low level of oxygen. In one aspect, obligate anaerobes engineered to produce mevalonate, isoprene, isoprenoid precursors, and isoprenoids can serve as host cells for any of the methods and/or compositions described herein and are grown under substantially oxygen-free conditions, wherein the amount of oxygen present is not harmful to the growth, maintenance, and/or fermentation of the anaerobes.

In another aspect of the invention, the host cells described and/or used in any of the compositions or methods described herein are facultative anaerobic cells and progeny thereof. Facultative anaerobes can generate cellular ATP by aerobic respiration (e.g., utilization of the TCA cycle) if oxygen is present. However, facultative anaerobes can also grow in the absence of oxygen. This is in contrast to obligate anaerobes which die or grow poorly in the presence of greater amounts of oxygen. In one aspect, therefore, facultative anaerobes can serve as host cells for any of the compositions and/or methods provided herein and can be engineered to produce mevalonate, isoprene, isoprenoid precursors, and isoprenoids. Facultative anaerobic host cells can be grown under substantially oxygen-free conditions, wherein the amount of oxygen present is not harmful to the growth, maintenance, and/or fermentation of the anaerobes, or can be alternatively grown in the presence of greater amounts of oxygen.

The host cell can additionally be a filamentous fungal cell and progeny thereof. (See, e.g., Berka & Barnett, *Biotechnology Advances,* (1989), 7(2):127-154). In some aspects, the filamentous fungal cell can be any of *Trichoderma longibrachiatum, T. viride, T. koningii, T. harzianum, Penicillium* sp., *Humicola insolens, H. lanuginose, H. grisea, Chrysosporium* sp., *C. lucknowense, Gliocladium* sp., *Aspergillus* sp., such as *A. oryzae, A. niger, A sojae, A. japonicus, A. nidulans,* or *A. awamori, Fusarium* sp., such as *F. roseum, F. graminum F. cerealis, F. oxysporuim,* or *F. venenatum, Neurospora* sp., such as *N. crassa, Hypocrea* sp., *Mucor* sp., such as *M. miehei, Rhizopus* sp. or *Emericella* sp. In some aspects, the fungus is *A. nidulans, A. awamori, A. oryzae, A. aculeatus, A. niger, A. japonicus, T. reesei, T. viride, F. oxysporum,* or *F. solani.* In certain embodiments, plasmids or plasmid components for use herein include those described in U.S. patent pub. No. US 2011/0045563.

The host cell can also be a yeast, such as *Saccharomyces* sp., *Schizosaccharomyces* sp., *Pichia* sp., or *Candida* sp. In some aspects, the *Saccharomyces* sp. is *Saccharomyces cerevisiae* (See, e.g., Romanos et al., *Yeast,* (1992), 8(6):423-488). In certain embodiments, plasmids or plasmid components for use herein include those described in U.S. Pat. No. 7,659,097 and U.S. patent pub. No. US 2011/0045563.

The host cell can additionally be a species of algae, such as a green algae, red algae, glaucophytes, chlorarachniophytes, euglenids, chromista, or dinoflagellates. (See, e.g., Saunders & Warmbrodt, "*Gene Expression in Algae and Fungi, Including Yeast,*" (1993), National Agricultural Library, Beltsville, Md.). In certain embodiments, plasmids or plasmid components for use herein include those described in U.S. Patent Pub. No. US 2011/0045563. In some aspects, the host cell is a cyanobacterium, such as cyanobacterium classified into any of the following groups based on morphology: *Chlorococcales, Pleurocapsales, Oscillatoriales, Nostocales*, or *Stigonematales* (See, e.g., Lindberg et al., Metab. Eng., (2010) 12(1):70-79). In certain embodiments, plasmids or plasmid components for use herein include those described in U.S. Patent Pub. No.: US 2010/0297749; US 2009/0282545 and Intl. Pat. Appl. No. WO 2011/034863.

*E. coli* host cells can be used to express one or more isoprene synthase, acetoacetyl co-A synthase, MVA pathway enzyme, DXP pathway enzyme, phosphoketolase, and/or a polyprenyl pyrophosphate synthase polypeptides in the compositions and methods described herein. In one aspect, the host cell is a recombinant cell of an *Escherichia coli* (*E. coli*) strain, or progeny thereof, capable of producing isoprene, isoprenoid precursor molecules, and/or isoprenoids that expresses one or more nucleic acids encoding isoprene synthase, acetoacetyl co-A synthase, MVA pathway enzyme, DXP pathway enzyme, phosphoketolase, and/or a polyprenyl pyrophosphate synthase polypeptides. The *E. coli* host cells can produce isoprene, isoprenoid precursor molecules, and/or isoprenoids in amounts, peak titers, and cell productivities greater than that of the same cells lacking one or more heterologously expressed nucleic acids encoding isoprene synthase, acetoacetyl co-A synthase, MVA pathway enzyme, DXP pathway enzyme, phosphoketolase, and/or a polyprenyl pyrophosphate synthase polypeptides. In addition, the one or more heterologously expressed nucleic acids encoding isoprene synthase, acetoacetyl co-A synthase, MVA pathway enzyme, DXP pathway enzyme, phosphoketolase, and/or a polyprenyl pyrophosphate synthase polypeptides in *E. coli* can be chromosomal copies (e.g., integrated into the *E. coli* chromosome). In other aspects, the *E. coli* cells are in culture.

In other aspects, the host cell can be a species of yeast other than *S. cerevisiae* such as, but not limited to, a *Pichia* spp., a *Candida* spp., a *Hansenula* spp., a *Kluyveromyces* spp., a *Kluyveromyces* spp., or a *Schizosaccharomyces* spp. In still other aspects, the host cell can be a species of bacterium including, but not limited to, an *Arthrobacter* spp., a *Zymomonas* spp., a *Brevibacterium* spp., a *Clostridium* spp., an *Aerococcus* spp., a *Bacillus* spp., an *Actinobacillus* spp. (such as, but not limited to, *A. succinogens*), a *Carbobacterium* spp., a *Corynebacterium* spp., an *Enterococcus* spp., an *Erysipelothrix* spp., a *Gemella* spp., a *Geobacillus* spp., a *Globicatella* spp., a *Lactobacillus* spp. (such as, but not limited to, *L. lactis* and *L. rhammosus*), a *Lactococcus* spp., a *Leuconostoc* spp., a *Pediococcus* spp., a *Streptococcus* spp., a *Tetragenococcus* spp., an *Actinobacillus* spp., or a *Vagococcus* spp., In other aspects, the fermenting organism can be a fungus such as, but not limited to, a *Rhizopus* spp.

In other aspects, the host cell can be a lactic acid bacteria, such as those of the genera *Aerococcus, Bacillus, Carbobacterium, Enterococcus, Erysipelothrix, Gemella, Globicatella, Lactobacillus, Lactococcus, Leuconostoc, Pediococcus, Streptococcus, Tetragenococcus* and *Vagococcus*. For example, other bacteria of the genus *Lactobacillus* which may be substituted include, but are not limited to, *L. heiveticus, L. delbrueckii, L. casei, L, acidophilus, L. amylovorus, L. leichmanii* or *L. bulgaricus. L. amylovorus*, and *L. pentosus*.

B. Methods for the Production of Isoprene, Isoprenoid Precursor Molecules, and/or Isoprenoids Using DSTFS-Derived Feedstocks In one aspect, provided herein are methods for the production of isoprene, isoprenoid precursor molecules, and/or isoprenoids by recombinant host cells (such as any of the recombinant host cells disclosed above) in culture using the fermentable sugar feedstocks produced by any of the methods disclosed above as a source of carbon. The host cells can express one or more heterologous nucleic acids encoding an isoprene synthase polypeptide and one or more mevalonate (MVA) pathway polypeptides. In some aspects of the method, endogenous enzyme activity in a whole or fractionated grain is inactivated prior to treatment of the grain with a high concentration of amylase at temperatures below the gelatinization temperature of starch and with a glucoamylase to decrease the amount of DP2 saccharides present in the feedstock. The host cells are cultured in a culture media containing the feedstock and produce isoprene, isoprenoid precursor molecules, and/or isoprenoids.

Endogenous enzyme activity in the a whole or fractionated grain can be inactivated by using any of the methods disclosed herein, including, but not limited to, exposure of an aqueous slurry containing the whole or fractionated grain to low pH. In some aspects, the pH is lowered to any of about pH 1, 1.5, 2, 2.5, 3, 3.5, or 4 to inactivate the endogenous enzyme activity. In other aspects, the slurry is exposed to lowered pH for any of about 30 min, about 60 min, about 90 min, about 120, about 150 min, or about 180 min, inclusive, including any times in between these numbers. In yet other aspects, the slurry is exposed to lowered pH at a temperature of about 37° C., 40° C., 45° C., 50° C., 55° C., 60° C., 65° C., 70° C., 75° C., or 80° C., inclusive, including any temperatures in between these values.

In some aspects, enzymatic treatment of the grain can conducted at a temperature between about 0° C. to about 40° C. (such as between about 0° C. to about 30° C.) below the gelatinization temperature of the starch present in a particular grain used in any of the methods disclosed herein. In other aspects, the treatment is conducted at a temperature between about 0 to 5° C., between about 2 to 7° C., between about 4 to 9° C., between about 6 to 11° C., between about 8 to 13° C., between about 10 to 15° C., between about 12 to 17° C., between about 13 to 19° C., between about 15 to 21° C., between about 17 to 23° C., between about 19 to 25° C., between about 21 to 27° C., between about 23 to 29° C., between about 25 to 31° C., between about 27 to 33° C., between about 29 to 35° C., between about 31 to 37° C., between about 33 to 39° C. or between about 35 to 40° C., inclusive, below the gelatinization temperature of the starch present in a particular grain used in any of the methods disclosed herein. In some aspects, the treatment is conducted at a temperature between about 55-65° C., inclusive. In other aspects, the treatment is conducted at a temperature between about 57-65° C., 59-65° C., 61-65° C., or 63-65 C ° C., inclusive. In yet other aspects, the treatment is conducted at a temperature between about 55-63° C., 55-61° C., 55-59° C., or 55-57° C., inclusive. In other aspects, the treatment is conducted at a temperature at least about 55° C., at least about 57° C., at least about 59° C., at least about 61° C., at least about 63° C., or at least about 65° C. In still further aspects, the treatment is conducted at a temperature no greater than about 65° C., about 63° C., about 61° C., about 59° C., about 57° C., or about 55° C.

In other aspects of the methods provided herein, treatment of the slurry with a high concentration of alpha amylase (as further detailed below) and a glucoamylase can be conducted for between about 12-60 hours. In some aspects, the treatment of the slurry is conducted for between about 12-55 hours, 12-50 hours, 12-45 hours, 12-40 hours, 12-35 hours, 12-30 hours, 12-25 hours, 12-20 hours, or 12-15 hours. In still further aspects, the treatment of the slurry is conducted for between about 15-60 hours, 20-60 hours, 25-60 hours, 30-60 hours, 35-60 hours, 40-60 hours, 45-60 hours, 50-60 hours, or 55-60 hours. In other aspects, the treatment of the slurry is conducted for 15-55, 20-50, 25-45, or 30-40 hours. In another aspect, the treatment of the slurry is conducted for any of about 2 hours, about 4 hours, about 6 hours, about 12 hours, about 24 hours, or about 48 hours, inclusive, including any time in between these numbers.

In some aspects the starch solubilizing alpha amylase can be any of the alpha amylases disclosed above (including an acid fungal alpha amylase, an AmyE amylase, or an AmyE variant amylase) and the high concentration used in the methods described herein can be any of about 1 AAU/gds, 2 AAU/gds, 3 AAU/gds, 4 AAU/gds, 5 AAU/gds, 6 AAU/gds, 7 AAU/gds, 8 AAU/gds, 9 AAU/gds, 10 AAU/gds, 11 AAU/gds, 12 AAU/gds, 13 AAU/gds, 14 AAU/gds, 15 AAU/gds, 16 AAU/gds, 17 AAU/gds, 18 AAU/gds, 19 AAU/gds, or 20 AAU/gds inclusive, including any values in between these concentrations. In some aspects, the high concentration of alpha amylase is greater than about 10 AAU/gds, including concentrations greater than about 12 AAU/gds, about 14 AAU/gds, about 16 AAU/gds, about 18 AAU/gds, or about 20 AAU/gds, inclusive, including any concentrations in between these values. In other aspects, the high concentration of alpha amylase used for the liquefaction reaction is between about 3-9 AAU/gds, 4-8 AAU/gds, or 5-7 AAU/gds, inclusive. In still other aspects, the high concentration of alpha amylase used for the liquefaction reaction is between about 3-10 AAU/gds, 4-10 AAU/gds, 5-10 AAU/gds, 6-10 AAU/gds, 7-10 AAU/gds, 8-10 AAU/gds, or 9-10 AAU/gds, inclusive. In a further aspect, the high concentration of alpha amylase used for the liquefaction reaction is between about 3-9 AAU/gds, 3-8 AAU/gds, 3-7 AAU/gds, 3-6 AAU/gds, 3-5 AAU/gds, or 3-4 AAU/gds, inclusive. In another aspect, the high concentration of alpha amylase used for the liquefaction reaction is between about 5-10 AAU/gds, 5-15 AAU/gds, 5-20 AAU/gds, or 5-25 AAU/gds.

In other aspects, the glucoamylase can be any of the glucoamylases described above and the concentration of glucoamylase used for the methods described herein can be any of about 0.01-0.2 GAU/gds, inclusive. In other aspects, the concentration of glucoamylase is between about 0.05-0.15 GAU/gds, inclusive, or between about 0.75-0.1 GAU/gds, inclusive. In still other aspects, the concentration of glucoamylase is between about 0.01-0.2 GAU/gds, 0.03-0.2 GAU/gds, 0.05-0.2 GAU/gds, 0.07-0.2 GAU/gds, 0.09-0.2 GAU/gds, 0.11-0.2 GAU/gds, 0.13-0.2 GAU/gds, 0.15-0.2 GAU/gds, 0.17-0.2 GAU/gds, or 0.19-0.2 GAU/gds, inclusive. In a further aspect, the concentration of glucoamylase is between about 0.01-1.8 GAU/gds, 0.01-1.6 GAU/gds, 0.01-1.4 GAU/gds, 0.01-1.2 GAU/gds, 0.01-1.0 GAU/gds, 0.01-0.8 GAU/gds, 0.01-0.6 GAU/gds, 0.01-0.4 GAU/gds, or 0.01-0.2 GAU/gds, inclusive. In another aspect, the concentration of glucoamylase is any of about 0.025 GAU/gds, about 0.05 GAU/gds, about 0.075 GAU/gds, about 0.1 GAU/gds, or about 0.2 GAU/gds, inclusive, including any concentrations in between these values.

Provided herein are methods of producing isoprene by culturing any of the recombinant cells described herein under conditions such as those disclosed herein using the fermentable sugar feedstocks produced by any of the methods described herein as a carbon source. In one aspect, isoprene can be produced by culturing recombinant cells expressing one or more nucleic acids encoding: (a) an isoprene synthase polypeptide, wherein the isoprene synthase polypeptide is encoded by a heterologous nucleic acid; and (b) one or more mevalonate (MVA) pathway polypeptides in culture media containing the fermentable sugar feedstocks produced by any of the methods described herein as a carbon source. In one aspect, one or more heterologous nucleic acids encoding a HMG-CoA reductase, a lower MVA pathway polypeptide, and an isoprene synthase polypeptide can be used. In another aspect, isoprene can be produced by culturing recombinant cells comprising one or more heterologous nucleic acids encoding a HMG-CoA reductase and HMG-CoA synthase, a lower MVA pathway polypeptide, and an isoprene synthase polypeptide. In yet another aspect, one or more heterologous nucleic acids encoding one or more upper MVA pathway polypeptides, one or more lower MVA pathway polypeptides, and/or one or more DXP pathway polypeptides can be used. In some aspects, the recombinant cells described herein exhibit any of about 10%, 15%, 20%, 25%, 30%, 35%, 40%, 45%, 50%, 55%, 60%, 65%, 70%, 75%, 80%, 95%, or 100%, inclusive, including any value in between these percentages, increased isoprene production in comparison to cells which do not comprise one or more heterologous nucleic acids encoding an isoprene synthase polypeptide and one or more MVA pathway polypeptides. The isoprene can be produced from any of the cells described herein and according to any of the methods described herein. Any of the cells can be used for the purpose of producing isoprene using the fermentable sugar feedstocks produced by any of the methods described herein as a carbon source.

The cells can further express one or more nucleic acid molecules encoding the lower MVA pathway polypeptide(s) described above (e.g., MVK, PMK, MVD, and/or IDI), any of the upper MVA pathways polypeptide(s) described above (e.g., a thiolase, an acetoacetyl-CoA synthase, an HMG-CoA reductase, and/or an HMG-CoA synthase) and/or any of the isoprene synthase polypeptide(s) described above (e.g. *P. alba* isoprene synthase). In some aspects, the recombinant (e.g., bacterial) cells can be any of the cells described herein. Any of the isoprene synthases or variants thereof described herein, any of the bacterial strains described herein, any of the promoters described herein, and/or any of the vectors described herein can also be used to produce isoprene using culture media containing the fermentable sugar feedstocks produced by any of the methods described herein as a carbon source. In some aspects, the method of producing isoprene further comprises a step of recovering the isoprene.

In some aspects, the amount of isoprene produced is measured at a productivity time point. In some aspects, the productivity for the cells is about any of the amounts of isoprene disclosed herein. In some aspects, the cumulative, total amount of isoprene produced is measured. In some aspects, the cumulative total productivity for the cells is about any of the amounts of isoprene disclosed herein.

In some aspects, any of the cells described herein (for examples the cells in culture) produce isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some aspects, the amount of isoprene is between about 2 to about 5,000 nmole/$g_{wcm}$/hr, such as between about 2 to about 100 nmole/$g_{wcm}$/hr, about 100 to about 500 nmole/

$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some aspects, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

In some aspects, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some aspects, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some aspects, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h.

In some aspects, the cells in culture produce a cumulative titer (total amount) of isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some aspects, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some aspects, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

In some aspects, the isoprene produced by the cells in culture (such as any of the recombinant cells described herein) comprises at least about 1, 2, 5, 10, 15, 20, or 25% by volume of the fermentation offgas. In some aspects, the isoprene comprises between about 1 to about 25% by volume of the offgas, such as between about 5 to about 15%, about 15 to about 25%, about 10 to about 20%, or about 1 to about 10%.

Also provided herein are methods for producing isoprenoids under conditions such as those disclosed herein using the fermentable sugar feedstocks produced by any of the methods described herein as a carbon source. In one aspect, isoprenoids can be produced by culturing recombinant cells expressing one or more nucleic acids encoding: (a) one or more heterologous nucleic acids encoding an MVA pathway polypeptide; and/or (b) one or more polyprenyl pyrophosphate synthase polypeptides in culture media containing the fermentable sugar feedstocks produced by any of the methods described herein as a carbon source. In another aspect, isoprenoids can be produced by culturing recombinant cells comprising one or more heterologous nucleic acids encoding a HMG-CoA reductase and HMG-CoA synthase, and a lower MVA pathway polypeptide. In yet another aspect, one or more heterologous nucleic acids encoding one or more upper MVA pathway polypeptides, one or more lower MVA pathway polypeptides, one or more polyprenyl pyrophosphate synthase polypeptides, and/or one or more DXP pathway polypeptides can be used. In some aspects, the recombinant cells described herein exhibit any of about 10%, 15%, 20%, 25%, 30%, 35%, 40%, 45%, 50%, 55%, 60%, 65%, 70%, 75%, 80%, 95%, or 100%, inclusive, including any value in between these percentages, increased isoprenoid production in comparison to cells which do not comprise one or more heterologous nucleic acids encoding an one or more MVA pathway polypeptides and one or more polyprenyl pyrophosphate synthase polypeptides. The isoprenoids can be produced from any of the cells described herein and according to any of the methods described herein. Any of the cells can be used for the purpose of producing isoprenoids using the fermentable sugar feedstocks produced by any of the methods described herein as a carbon source.

Thus, provided herein are methods for producing isoprenoids by culturing recombinant cells comprising one or more heterologous nucleic acids encoding (a) one or more heterologous nucleic acids encoding an MVA pathway polypeptide; and/or (b) one or more polyprenyl pyrophosphate synthase polypeptides in a suitable condition for producing isoprenoids and producing isoprenoids using any of the fermentable sugar feedstocks provided herein as a carbon source. The cells can further express one or more nucleic acid molecules encoding the lower MVA pathway polypeptide(s) described above (e.g., MVK, PMK, MVD, and/or IDI) and any of the polyprenyl pyrophosphate synthase polypeptide(s) described above. In some aspects, the recombinant cells can be any of the cells described herein. Any of the polyprenyl pyrophosphate synthase or variants thereof described herein, any of the host cells described herein, any of the promoters described herein, and/or any of the vectors described herein can also be used to produce isoprenoids using any of the fermentable sugar feedstocks provided herein as a carbon source.

The instant methods for the production isoprenoids can produce at least 5% greater amounts isoprenoids when compared to isoprenoid-producing recombinant cells that do not comprise (a) one or more heterologous nucleic acids encoding an MVA pathway polypeptide; and/or (b) one or more polyprenyl pyrophosphate synthase polypeptides. Alternatively, the recombinant cells can produce greater than about 1%, 2%, 3%, 4%, 5%, 6%, 7%, 8%, 9%, 10%, 11%, 12%, 13%, 14%, or 15% of isoprenoids, inclusive. In some aspects, the method of producing isoprenoids further comprises a step of recovering the isoprenoids. The production of isoprenoids can be enhanced by about 5% to about 1,000,000 folds. The production of isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoids by cells without the expression of one or more heterologous nucleic acids encoding one or more heterologous nucleic acids encoding one or more MVA pathway polypeptides and/ or one or more polyprenyl pyrophosphate synthase polypeptides.

The production of isoprenoids can also enhanced by at least about any of 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprenoids by cells without the expression of one or more heterologous nucleic acids encoding one or more MVA pathway polypeptides and/or one or more polyprenyl pyrophosphate synthase polypeptides.

In addition, more specific cell culture conditions can be used to culture the cells in the methods described herein. For example, in some aspects, the method for the production of isoprenoids involves the steps of culturing recombinant cells (including, but not limited to, E. coli cells) that do not endogenously express (a) one or more heterologous nucleic acids encoding an MVA pathway polypeptide; and/or (b) one or more polyprenyl pyrophosphate synthase polypeptides at 34° C., wherein the recombinant cells heterologously express one or more copies of a gene encoding (a) one or more heterologous nucleic acids encoding an MVA pathway polypeptide; and/or (b) one or more polyprenyl pyrophosphate synthase polypeptides on a low to medium copy plasmid and under the control of a strong promoter in culture media containing the fermentable sugar feedstocks produced by any of the methods described herein as a carbon source; and producing isoprenoids. In some aspects, the method further comprises a step of recovering the isoprenoids.

1. Transformation Methods

Nucleic acids encoding one or more copies of a nucleic acid encoding an mvaE and an mvaS polypeptide, an isoprene synthase polypeptide, MVA pathway polypeptides, DXP pathway polypeptides, phosphoketolase polypeptide, and/or polyprenyl pyrophosphate synthase polypeptides can be inserted into a microorganism using suitable techniques. Additionally, these nucleic acids or vectors containing them can be inserted into a host cell (e.g., a plant cell, a fungal cell, a yeast cell, or a bacterial cell described herein) using standard techniques for introduction of a DNA construct or vector into a host cell, such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (See, e.g., *Current Protocols in Molecular Biology* (F. M. Ausubel et al. (eds.) Chapter 9, 1987; Sambrook et al., *Molecular Cloning: A Laboratory Manual*, 2$^{nd}$ ed., Cold Spring Harbor, 1989; and Campbell et al., *Curr. Genet.* 16:53-56, 1989). The introduced nucleic acids can be integrated into chromosomal DNA or maintained as extrachromosomal replicating sequences. Transformants can be selected by any method known in the art. Suitable methods for selecting transformants are described in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

2. Exemplary Cell Culture Media

As used herein, the terms "minimal medium" or "minimal media" refer to growth medium containing the minimum nutrients possible for cell growth, generally, but not always, without the presence of one or more amino acids (e.g., 1, 2, 3, 4, 5, 6, 7, 8, 9, 10, or more amino acids). Minimal medium typically contains: (1) a carbon source for bacterial growth; (2) various salts, which can vary among bacterial species and growing conditions; and (3) water. In some aspects, the carbon source is provided by the fermentable sugar feedstocks produced according to any of the methods disclosed herein. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

Any minimal medium formulation can be used to cultivate the host cells. Exemplary minimal medium formulations include, for example, M9 minimal medium and TM3 minimal medium. Each liter of M9 minimal medium contains (1) 200 ml sterile M9 salts (64 g $Na_2HPO_4$-$7H_2O$, 15 g $KH_2PO_4$, 2.5 g NaCl, and 5.0 g $NH_4Cl$ per liter); (2) 2 ml of 1 M $MgSO_4$ (sterile); (3) 20 ml of 20% (w/v) glucose (or other carbon source); and (4) 100 µl of 1 M $CaCl_2$ (sterile). Each liter of TM3 minimal medium contains (1) 13.6 g $K_2HPO_4$; (2) 13.6 g $KH_2PO_4$; (3) 2 g $MgSO_4$*$7H_2O$; (4) 2 g Citric Acid Monohydrate; (5) 0.3 g Ferric Ammonium Citrate; (6) 3.2 g $(NH_4)_2SO_4$; (7) 0.2 g yeast extract; and (8) 1 ml of 1000× Trace Elements solution; pH is adjusted to ~6.8 and the solution is filter sterilized. Each liter of 1000× Trace Elements contains: (1) 40 g Citric Acid Monohydrate; (2) 30 g $MnSO_4$*$H_2O$; (3) 10 g NaCl; (4) 1 g $FeSO_4$*$7H_2O$; (4) 1 g $CoCl_2$*$6H_2O$; (5) 1 g $ZnSO_4$*$7H_2O$; (6) 100 mg $CuSO_4$*$5H_2O$; (7) 100 mg $H_3BO_3$; and (8) 100 mg $NaMoO_4$*$2H_2O$; pH is adjusted to ~3.0.

An additional exemplary minimal media includes (1) potassium phosphate $K_2HPO_4$, (2) Magnesium Sulfate $MgSO_4$*$7H_2O$, (3) citric acid monohydrate $C_6H_8O_7$*$H_2O$, (4) ferric ammonium citrate $NH_4FeC_6H_5O_7$, (5) yeast extract (from biospringer), (6) 1000× Modified Trace Metal Solution, (7) sulfuric acid 50% w/v, (8) foamblast 882 (Emerald Performance Materials), and (9) Macro Salts Solution 3.36 ml All of the components are added together and dissolved in deionized $H_2O$ and then heat sterilized. Following cooling to room temperature, the pH is adjusted to 7.0 with ammonium hydroxide (28%) and q.s. to volume. Vitamin Solution and spectinomycin are added after sterilization and pH adjustment.

In some aspects, the fermentable sugar feedstocks produced by any of the methods disclosed herein further include yeast extract or one or more components of yeast extract. In some aspects, the concentration of yeast extract is 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the carbon source includes both yeast extract (or one or more components thereof) and another carbon source, such as glucose.

3. Exemplary Cell Culture Conditions

Materials and methods suitable for the maintenance and growth of the recombinant cells of the invention are described infra, e.g., in the Examples section. Other materials and methods suitable for the maintenance and growth of bacterial cultures are well known in the art. Exemplary techniques can be found in International Publication No. WO 2009/076676, U.S. patent application Ser. No. 12/335,071 (U.S. Publ. No. 2009/0203102), WO 2010/003007, US Publ. No. 2010/0048964, WO 2009/132220, US Publ. No. 2010/0003716, *Manual of Methods for General Bacteriology* Gerhardt et al., eds), American Society for Microbiology, Washington, D.C. (1994) or Brock in *Biotechnology: A Textbook of Industrial Microbiology*, Second Edition (1989) Sinauer Associates, Inc., Sunderland, Mass. In some aspects, the cells are cultured in a culture medium under conditions permitting the expression of one or more MVA pathway, isoprene synthase, DXP pathway (e.g., DXS), IDI, MVA pathway, or PGL polypeptides encoded by a nucleic acid inserted into the host cells.

Standard cell culture conditions can be used to culture the cells (see, for example, WO 2004/033646 and references cited therein). In some aspects, cells are grown and maintained at an appropriate temperature, gas mixture, and pH (such as at about 20° C. to about 37° C., at about 6% to about 84% $CO_2$, and at a pH between about 5 to about 9). In some aspects, cells are grown at 35° C. in an appropriate cell medium. In some aspects, the pH ranges for fermentation are between about pH 5.0 to about pH 9.0 (such as about pH 6.0 to about pH 8.0 or about 6.5 to about 7.0). Cells can be grown under aerobic, anoxic, or anaerobic conditions based on the requirements of the host cells. In addition, more specific cell culture conditions can be used to culture the cells. For example, in some embodiments, the bacterial cells (such as *E. coli* cells) express one or more heterologous nucleic acids encoding mvaE and mvaS polypeptides under the control of a strong promoter in a low to medium copy plasmid and are cultured at 34° C.

Standard culture conditions and modes of fermentation, such as batch, fed-batch, or continuous fermentation that can be used are described in International Publication No. WO 2009/076676, U.S. patent application Ser. No. 12/335,071 (U.S. Publ. No. 2009/0203102), WO 2010/003007, US Publ. No. 2010/0048964, WO 2009/132220, US Publ. No. 2010/0003716. Batch and Fed-Batch fermentations are common and well known in the art and examples can be found in Brock, Biotechnology: *A Textbook of Industrial Microbiology*, Second Edition (1989) Sinauer Associates, Inc.

In some aspects, the bacterial cells are grown in batch culture. The bacterial cells can also be grown in fed-batch culture or in continuous culture. Additionally, the bacterial cells can be cultured in minimal medium, including, but not limited to, any of the minimal media described above. The minimal medium can be further supplemented with 1.0% (w/v) glucose, or any other six carbon sugar, or less. Specifically, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose. Additionally, the minimal medium can be supplemented 0.1% (w/v) or less yeast extract. Specifically, the minimal medium can be supplemented with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. Alternatively, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose and with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract.

4. Exemplary Purification Methods

In some aspects, any of the methods described herein further include a step of recovering isoprene, isoprenoid precursor molecules, and/or isoprenoids produced by any of the recombinant cells disclosed herein. In some aspects, the isoprene is recovered by absorption stripping (See, e.g., U.S. Patent Application Publication No. 2011/0178261 A1).

Suitable purification methods are described in more detail in U.S. Patent Application Publication No. US2010/0196977 A1.

Throughout this specification, various patents, patent applications and other types of publications (e.g., journal articles) are referenced. The disclosure of all patents, patent applications, and publications cited herein are hereby incorporated by reference in their entirety for all purposes.

The invention can be further understood by reference to the following examples, which are provided by way of illustration and are not meant to be limiting.

EXAMPLES

Example 1

The Effect of Grain Endogenous Starch Hydrolyzing Activity on the Solubilization of Granular Starch and Production of Fermentable Sugars at Temperatures Below that of the Gelatinization Temperature of the Grain In this Example, alpha amylase is used in combination with an endogenous starch hydrolyzing enzyme fraction derived from unprocessed grain to synergistically produce fermentable sugars having a DP of 1 or 2 at temperatures below the gelatinization temperature of the starch in the grain.

Materials and Methods

Alpha-Amylase Activity (AAU):

One AAU of bacterial alpha-amylase activity is the amount of enzyme required to hydrolyze 10 mg of starch per min from 5% dry substance soluble Lintner starch solution containing 31.2 mM calcium chloride, at 60° C. and 6.0 pH buffered with 30 mM sodium acetate.

Sugar Composition Determined by HPLC:

The composition of the reaction products of oligosaccharides was measured by high pressure liquid chromatographic method (Beckman System Gold 32 Karat Fullerton, Calif., USA) equipped with a HPLC column (Rezex 8 u8% H, Monosaccharides), maintained at 50° C. fitted with a refractive index (RI) detector (ERC-7515A, RI Detector from The Anspec Company, Inc.). Dilute sulfuric acid (0.01 N) was used as the mobile phase at a flow rate of 0.6 ml per minute. Twenty microliter of 4.0% solution was injected onto the column. The column separates based on the molecular weight of the saccharides. For example a designation of DP1 is a monosaccahride, such as glucose; a designation of DP2 is a disaccharide, such as maltose; a designation of DP3 is a trisaccharide, such as maltotriose and the designation "DP4+" is an oligosaccharide having a degree of polymerization (DP) of 4 or greater.

Percent Solubilization of Granular Starch:

Solubility testing is done by sampling from the agitated slurry into 2.5 ml micro-centrifuge tubes. The tubes are spun for ~4 minutes at 13,000 rpm and the refractive index of the supernatant is determined at 30 C ($RI_{sup}$). The total dry substance is determined by taking 1.5-2 ml of the starch slurry into a 2.5 ml spin tube, adding 1 drop of SPEZYME® FRED from a micro disposable-pipette then boiling 10 minutes. The tubes are spun for ~4 minutes at 13,000 rpm and the refractive index of the supernatant is determined at 30° C. ($RI_{tot}$). The dry substance of the supernatant and the whole sample (total) are determined using appropriate DE tables. Table for converting $RI_{sup}$ to DS is the 42 DE, Table I from the Critical Data Tables of the Corn Refiners Association, Inc. To convert $RI_{tot}$ to DS, more than one table can be used and an interpolation between the 32 DE and 42 DE tables employed. First an estimation of the solubilisation is made by dividing the DS from the supernatant by the starting DS*1.05. This estimated solubilization is used for the interpolation between the DS obtained via the 42DE and 32DE table. Solubility is defined as the dry substance of the supernatant divided by the total dry substance times 100. This value is then corrected to compensate for the impact of remaining granular starch.

This experiment was run on three different granular starch substrates: (A) Whole ground corn—150 g passed through 40-mesh sieve and having a moisture content of 14.6%; (B) Corn endosperm (obtained from Valero, Jefferson, Wis.) ground to pass through a 40-mesh sieve and having a moisture content of 14.4%; and (C) Refined corn starch—having a moisture content of 11.8%. Each substrate was weighed and transferred to a screw-capped glass jar to make a final 50 g slurry with water adjusting to 30% DS for whole ground corn and corn endosperm and 20% DS for refined starch.

The pH of the slurry was adjusted to pH 5.5 using 6N hydrochloric acid. SPEZYME® XTRA (from Genencor-Danisco) was added at 8.0 AAU/ds. The temperature was maintained at 60° C. During the incubation, the slurry was gently stirred in a shaking incubator. After time internals of 24 and 48 hours, the Refractive Index method was used to determine % starch solubilized and sugar compositions were determined.

TABLE 1

Solubility, DP, and percentage fermentables and fermentable sugar index obtained from substrates.

| Substrates | Treatments | Incubation Time (Hour) | % Solubility | % DP1 | % DP2 | % DP3 | % DP4+ | % Fermentables (DP1 + DP2) | Fermentable Sugar Index |
|---|---|---|---|---|---|---|---|---|---|
| Corn endosperm | No added enzyme | 0 | 5.4 | 20.25 | 3.28 | 6.40 | 41.65 | 23.5 | 0.49 |
| | | 24 | 8.7 | 72.09 | 4.49 | 5.18 | 18.24 | 76.6 | 3.27 |
| | | 48 | 8.7 | 69.45 | 6.08 | 5.47 | 18.99 | 75.5 | 3.08 |
| | Spezyme Xtra added | 24 | 69.5 | 44.44 | 27.88 | 15.2 | 12.48 | 72.3 | 2.61 |
| | | 48 | 72.7 | 51.79 | 27.67 | 12.57 | 7.98 | 79.5 | 3.87 |
| Whole ground corn | Spezyme Xtra added | 0 | 8.1 | 15.20 | 33.30 | 8.50 | 42.68 | 48.5 | 0.95 |
| | | 24 | 67.8 | 55.06 | 23.23 | 10.46 | 11.25 | 78.3 | 3.61 |
| | | 48 | 78.6 | 64.35 | 21.06 | 7.57 | 7.02 | 85.4 | 5.85 |
| Refined corn starch | Spezyme Xtra added | 24 | 76.1 | 3.95 | 13.42 | 16.27 | 66.36 | 17.4 | 0.21 |
| | | 48 | 84.0 | 4.73 | 15.13 | 18.29 | 61.85 | 19.9 | 0.25 |

Results

The data in Table 1 show that the incubation of refined starch (pure starch) with SPEZYME® XTRA, at 60° C. resulted in greater than 80% solubilization of the granular corn starch. At the same time, however, the soluble sugar syrup contained only about 20% fermentable sugars with a low fermentable sugar index of 0.25. In contrast, incubation of whole ground corn or endosperm (without germ and crude fiber) with SPEZYME® XTRA resulted in not only high solubilization of granular starch, but also a significantly high level of fermentable sugars. Without being bound by theory, it is believed that the high level of fermentable sugars obtained suggests the role of endogenous starch hydrolyzing enzymes which are present in whole ground corn or corn endosperm but that absent from refined corn starch. As can be seen from Table 1, the fermentable sugar index of whole ground corn or fractionated corn was increased to greater than 3 compared to 0.25 which was observed using refined starch as substrate during incubation with SPEZYME® XTRA. The granular starch solubilizing effect of SPEZYME® XTRA coupled to the hypothesized fermentable sugar-producing endogenous enzymes in the grain, produced a soluble high fermentable sugar yield using granular starch feed stock.

Example 2

Solubilization and Fermentable Sugar Composition of De-Hulled Milo Incubated with Alpha Amylase and Glucoamylase This study used alpha amylase in combination with glucoamylase (GA) to produce fermentable sugars at temperatures below the gelatinization temperature of the starch in the grain.

Materials and Methods

Glucoamylase Activity Units (GAUs):

One Glucoamylase Unit is the amount of enzyme that liberates one gram of reducing sugars calculated as glucose from a 2.5% dry substance soluble Lintner starch substrate per hour at 60° C. and 4.3 pH buffered with 20 mM sodium acetate.

Whole ground de-hulled Milo (obtained from ICM, Colwich, Kans.) having a moisture content of 13.03% was screened through 30-mesh sieve. An aqueous slurry containing 30% ds was prepared and the pH of the slurry was adjusted to pH 5.5 using 6N hydrochloric acid. SPEZYME® RSL was added at a concentration of 8.0 AAU/ds. To one of the flasks, H-GA was added at a concentration of 0.1 GAU/gds. The temperature was maintained at 60° C. During the incubation, the slurry was gently stirred for uniform mixing. After 48 hours, the Refractive Index method was used to determine percent starch solubilized and sugar composition of the solubilized sugars was determined using HPLC.

TABLE 2

Solubility, DP, and percentage fermentable sugars obtained from de-hulled milo.

| | Treatments | Incubation Time (Hour) | % Solubility | % DP1 | % DP2 | % DP3 | % DP4+ | % Fermentable sugars (DP1 + DP2) |
|---|---|---|---|---|---|---|---|---|
| Dehulled Milo | No treatment | 0 | 10.8 | 15.48 | 24.31 | 9.55 | 50.66 | 39.79 |
| | No H-GA added | 48 | 77.7 | 72.51 | 15.36 | 5.6 | 6.53 | 87.9 |
| | 0.1 GAU/gds | 48 | 92 | 85.76 | 9.42 | 1.44 | 3.39 | 95.2 |

Results

Incubation of de-hulled milo with SPEZYME® RSL solubilized greater than 75% of the Milo granular starch in 48 hours at 60° C. The solubilized starch was further hydrolyzed to produce a fermentable sugar syrup containing 87.9% DP1 and DP2. Further addition of 0.1 GAU of H-GA per gram ds resulted in greater than 90% solubilization of the Milo granular starch containing 95% fermentable sugar. This studies shows that alpha amylase in combination with glucoamylase can be used in combination to produce high percentage yields of fermentable sugars at temperatures below that of the gelatinization temperature of starch present in de-hulled milo.

Example 3

Effect of pH on the Solubilization and Hydrolysis of Corn Endosperm Granular Starch During Incubation with Alpha Amylase This study examined the effect of pH on the solubilization and hydrolysis of corn endosperm granular starch (30% DS) during incubation with alpha-amylase at a temperature below the gelatinization temperature of starch.

Materials and Methods

Ground corn endosperm having a moisture content of 14.4% was weighed and transferred to different screw-capped glass jars and water was added to a final ds of 30%. The pH was adjusted to pH 4.5, 5.0, 5.5 and 6.0, respectively. The aqueous slurry was stirred well and the pH was adjusted until the pH was stabilized to the target pH. The jar was pre-warmed for one hour in a 60° C. shaking incubator, followed by addition of SPEZYME® RSL at a concentration of 8.0 AAU/gds. The slurry was then gently stirred for 15 hours. The percent solubilization was then determined as described in Example 1.

TABLE 3 pH optimum for percent solubilization of grain using alpha-amylase below the initial gelatinization temperature of the grain.

| | pH | | | |
|---|---|---|---|---|
| | 4.5 | 5.0 | 5.5 | 6.0 |
| Solubilization | 23.8% | 66.5% | 68.3% | 66.3% |

Results

The results are shown in Table 3. The experimental results indicate that maximum solubilization of the granular starch occurred at the pH optimum for SPEZYME® RSL which is pH 5.

Example 4

Effect of Alpha-Amylase Concentration on the Solubilization and Hydrolysis of Corn Endosperm Granular Starch The experiment was conducted to study the effect of variable alpha-amylase concentrations on the solubilization of corn endosperm (30% ds) during incubation at pH 5.5 at a temperature below the gelatinization temperature of the starch in the corn endosperm.

Materials and Methods

SPEZYME® RSL at concentrations of 2 AAU/gds, 4 AAU/gds, 6 AAU/gds, 8 AAU/gds, and 10 AAU/gds was incubated with 30% ds corn endosperm at pH 5.5 and at a temperature of 60° C. During the incubation the slurry was gently stirred with an overhead mixer. After time internals of 2, 4, 6, 12 and 24 hours, the percent solubilized starch and sugar compositions (% W/W) were determined. Percent solubility, DP of sugars produced, and percentage fermentable sugars obtained were measured and calculated as described above.

Results

TABLE 4

Solubility, DP, and percentage fermentable sugars obtained from corn endosperm.

| | AAU/gds | | | | |
|---|---|---|---|---|---|
| | 2 | 4 | 6 | 8 | 10 |
| % Solubility | 60.3 | 68.0 | 70.8 | 73.5 | 75.1 |
| % DP1 | 58.06 | 50.12 | 48.77 | 44.38 | 44.78 |
| % DP2 | 24.89 | 26.84 | 27.29 | 28.31 | 28.10 |
| % DP3 | 9.81 | 12.93 | 13.61 | 15.42 | 15.28 |
| % DP 4+ | 7.24 | 10.11 | 10.33 | 11.89 | 11.84 |
| % DP1 + DP2 (% Fermentable sugars) | 82.93 | 76.96 | 76.06 | 72.69 | 72.88 |

The results are shown in Table 4. Alpha-amylase with a concentration of 2 AAU/gds gave a higher percentage DP1 and DP2 and a lower concentration of DP3 or DP4+ than either the 8 AAU/gds or 10 AAU/gds conditions. Additionally, Alpha-amylase with a concentration of 2 AAU/gds resulted in superior overall percentage of fermentable sugars.

Example 5

The Effect of *Humicola* Glucoamylase Concentration Used in Conjunction with Alpha-Amylase on the Solubilization of Corn Endosperm Granular Starch in Corn Endosperm This study looked at the effect of varied *Humicola*-glucoamylase (GA) concentrations on the solubilization and hydrolysis of corn endosperm granular starch by alpha-amylase during incubation at pH 5.5 and at a temperature below the gelatinization temperature of the starch in the corn endosperm.

Materials and Methods

Endosperm (Valero Renewable Jefferson Plant, N5355 Junction Rd. Jefferson, and WI. 53549) was ground in a mill and then passed through sieve having a 590 micron opening. The moisture content was 14.8%. An aqueous slurry containing 30% DS was made and the pH was adjusted to 5.4. After pre-warming incubation jars for ~30 min in the 60° C. shaking incubator, SPEZYME® RSL was dosed to all of jars at a rate of 8 AAU/g of ds endosperm and increasing dose concentrations of *Humicola* glucoamylase (0.025, 0.05, 0.075, 0.1 and 0.2 GAU/gds) were added the series of jars. Then, the slurry was gently shaken at 160 rpm. After 48 hours the solubility and sugar composition of the soluble fraction were determined as described in Example 1.

Results

TABLE 5

Solubility, DP, and percentage fermentable sugars obtained from corn endosperm.

|  | 8 AAU | 8 AAU + 0.025 GAU | 8 AAU + 0.05 GAU | 8 AAU + 0.075 GAU | 8 AAU + 0.1 GAU | 8 AAU + 0.2 GAU |
|---|---|---|---|---|---|---|
| % Solubility | 80.6 | 89.9 | 90.6 | 92 | 92.7 | 94.9 |
| % DP1 | 61.02 | 80.19 | 86.05 | 88.46 | 89.81 | 91.29 |
| % DP2 | 22.89 | 14.63 | 10.57 | 8.85 | 7.89 | 6.81 |
| % DP3 | 9.23 | 3.11 | 1.8 | 1.26 | 0.98 | 0.71 |
| % DP 4+ | 6.86 | 2.07 | 1.59 | 1.42 | 1.32 | 1.18 |
| % DP1 + DP2 | 83.91 | 94.82 | 96.62 | 97.31 | 97.8 | 98.1 |

The results are shown in Table 5. Both starch solubilization and production of fermentable sugar content were increased with increasing concentration of glucoamylase during incubation of endosperm with 8 AAU/gds of SPEZYME® RSL.

Example 6

Corn Endosperm Solubilization by Varied Glucoamylases

This study examined the effect of different glucoamylases on the solubilization and hydrolysis of corn endosperm granular starch by alpha-amylase during incubation at pH 5.5 and at a temperature below the gelatinization temperature of the starch in the corn endosperm.

Materials and Methods

Milled Corn endosperm with a moisture content of 14.4% and screened through U.S. Standard #40 screen was weighed into different screw-capped glass jars so as to contain 50 g of slurry at 30% ds. The pH was then adjusted to 5.4-5.5.

After pre-warming incubation jars for ~30 min at 60° C. in a shaking incubator, 8 AAU/gds of SPEZYME® RSL was added along with different glucoamylases (A. niger-GA (OP-TIDEX® L-400 from Genencor Danisco), Tr-GA (GC 147 from Genencor-Danisco) and Humicola-GA (H-GA; Genencor-Danisco)) at 0.1 GAU/gds to successive jars. Then, the slurry was gently shaken at 160 rpm. After 48 hours, the percent solubilization and the sugar composition in the soluble fraction were determined as detailed in Example 1.

Results

The results are shown in Table 6. Humicola-GA produced 97.7% fermentable sugar compared to lower percentages of fermentable sugars obtained using other GAs.

Example 7

The Effect of Variable Dry Solid Concentrations on Solubility and Percent Fermentable Sugar This experiment was conducted to compare the effect of different concentrations of dry solids (ds) in corn endosperm slurry on enzymatic breakdown of starch by alpha-amylase and GA at a temperature below the gelatinization temperature of the starch in the corn endosperm.

Materials and Methods

The experiment was run on four different concentrations of dry solids: 30%, 32%, 34% and 36%. Respective slurries having different dry solids level were weighed and transferred to screw-capped glass jars to make a final 50 g slurry. The pH of the slurry was adjusted to pH 5.4 using 6N hydrochloric acid. SPEZYME® Xtra (12.0 AAU/gds) and H-GA (0.05 and 0.1 HAU/gds) were then added. The temperature was maintained at 60° C. During the incubation, the slurry was gently stirred in a shaking incubator. After 47 hours, the Refractive Index method was used to determine the percent of the starch solubilized and sugar compositions of the solubilized starch fraction were determined by HPLC as described in Example 1.

TABLE 6

Solubility, DP, and percentage fermentable sugars obtained from corn endosperm.

| Glucoamylase | % Solubility | % DP1 | % DP2 | % DP3 | % DP4+ | % Fermentables DP1 + DP2 |
|---|---|---|---|---|---|---|
| H-GA | 92.7 | 89.81 | 7.89 | 0.98 | 1.32 | 97.70 |
| Tr-GA | 92.8 | 83.41 | 12.76 | 2.14 | 1.68 | 96.17 |
| An-GA | 92.5 | 80.09 | 14.58 | 3.19 | 2.14 | 94.67 |

Results

TABLE 7

Solubility, DP, and percentage fermentable sugars obtained from corn endosperm having variable concentrations of dry solids.

| DS (%) | Treatments (/gds) | % Solubility | % DP1 | % DP2 | % DP3 | % DP4+ | % Fermentables (DP1 + DP2) |
|---|---|---|---|---|---|---|---|
| 30 | 12AAU + 0.05GAU | 94.3 | 85.53 | 10.89 | 1.94 | 1.65 | 96.4 |
| 30 | 12AAU + 0.1GAU | 95.8 | 89.55 | 8.1 | 1.03 | 1.31 | 97.7 |
| 32 | 12AAU + 0.05GAU | 84.1 | 86.26 | 10.35 | 1.91 | 1.48 | 96.6 |
| 32 | 12AAU + 0.1GAU | 90.2 | 89.29 | 8.24 | 1.04 | 1.43 | 97.5 |
| 34 | 12AAU + 0.05GAU | 79.6 | 86.1 | 10.5 | 1.91 | 1.49 | 96.6 |
| 34 | 12AAU + 0.1GAU | 86.2 | 89.05 | 8.28 | 1.13 | 1.54 | 97.3 |
| 36 | 12AAU + 0.05GAU | 85.3 | 84.54 | 11.59 | 2.11 | 1.76 | 96.1 |
| 36 | 12AAU + 0.1GAU | 85.3 | 88.89 | 8.49 | 1.15 | 1.47 | 97.4 |

The results are shown in Table 7 which indicates that solubilization of the granular starch decreased with increasing ds. However, the addition of more glucoamylase resulted in an increase in the solubilization of up to 34% ds. The highest percentage of fermentable sugars was obtained with using 30% ds and 0.1 GAU *Humicola* glucoamylase.

Example 8

Simultaneous Production of a Fermentation Feedstock and a Co-Product of Corn Gluten Fiber This study examined the simultaneous production of fermentation feedstock and a co-product of corn gluten fiber fraction.

Materials and Methods

Corn endosperm (Valero Renewable Jefferson Plant, N5355 Junction Rd. Jefferson Wis. 53549) was ground in an MPX mill at minimum clearance to have a particle size distribution of 1.6% on a 590 micron opening sieve, 10% on a 420 micron opening sieve and 88.4% through the 420 micron opening sieve. The moisture content was 14.2%. A twelve kg aqueous slurry containing 31.2% DS was made and the pH was adjusted to 5.4 with 6 N HCl. The slurry was then transferred to a 14 liter reactor fitted with a turbine bladed agitator driven from the bottom. The reactor was temperature controlled via heat exchange coils and an external heated circulating water bath.

The slurry was dosed with 8 AAU of SPEZYME® RSL and 0.05 GAU of HGA per gram of dry substance. The reaction was sampled for percent solubilization and saccharide composition at various times before terminating at 48 hours of reaction.

The resulting co-product insoluble fraction was separated by vacuum filtration across 24 cm #4 Whatman paper into a 4 liter side arm vacuum flask at 26-28 inches of vacuum. The resulting cake was washed with a volume of water that was approximately half the original volume of slurry and then dried in a forced draft oven at 35° C. for 40 hours. This material was ground through a falling number mill at setting #2.

Protein Determination:

Protein concentrations in the insoluble corn protein fiber fraction (CPFF) were determined using the Bradford Quick-Start™ Dye Reagent (Bio-Rad, California, USA). For example, a 10 µL sample of the enzyme was combined with 200 10 µL Bradford QuickStart™ Dye Reagent. After thorough mixing. It was then incubated for at least 10 minutes at room temperature. Air bubbles were removed and the optical density was measured at 595 nm. The protein concentration was then calculated using a standard graph with bovine serum albumin.

Results

TABLE 8

Solubility, dissolved solids in sugar syrup, DP, and percentage fermentable sugars obtained from corn endosperm sampled at various reaction times.

| Reaction time | % Soluble | DS of Syrup | DP1 | DP2 | DP3 | DP4 | DP5+ | DP1 + DP2 |
|---|---|---|---|---|---|---|---|---|
| 4 | 58.9 | 19.6 | 52.6 | 27.9 | 9.1 | 3.0 | 7.4 | 80.5 |
| 8 | 70.2 | 23.1 | 63.0 | 24.9 | 6.2 | 2.0 | 3.9 | 87.9 |
| 12 | 77.1 | 24.8 | 68.8 | 21.6 | 5.2 | 1.5 | 3.0 | 90.4 |
| 24 | 87.8 | 27.5 | 78.9 | 15.4 | 3.4 | 0.7 | 1.7 | 94.3 |
| 35 | 91.2 | 28.6 | 83.1 | 12.7 | 2.4 | 0.4 | 1.3 | 95.8 |
| 48 | 94.1 | 29.3 | 85.5 | 11.0 | 1.9 | 0.3 | 1.2 | 96.6 |

Table 8 shows that greater than 94% of the starch is solubilized in 48 hours and that greater than 96% fermentable are produced with the composition of 29.3% DP1+85.5% DP2. The high level of percent fermentable sugars (DP1+DP2) demonstrates the value of the endogenous hydrolyzing enzymes remaining in the corn endosperm.

TABLE 9

Composition co-products from insoluble corn protein fiber fraction (CPFF)

| Parameter | CPFF | Endosperm | CGM | Corn | DDGS | CGF |
|---|---|---|---|---|---|---|
| % Dry Substance | 93.65 | 86.2 | 90 | 84 | 89 | 88.5 |
| % Starch (dsb) | 32.2 | 83.3 | 19 | 71.7 | | |
| % Crude Protein (dsb) | 29.5 | 7.4 | 66.7 | 9.5 | 30.8 | 22.6 |
| % Fat (dsb) | 5.94 | 1.5 | 2.8 | 4.3 | 11.2 | 4.0 |
| % Acid detergent fiber (dsb) | 7.16 | 1.2 | 5.5 | 3.3 | 13.7 | 14.7 |
| % Ash (dsb) | 0.43 | 0.36 | 2 | 1.4 | 5.7 | 8 |
| % Total digestible nutrients (dsb) | 88.8 | 89.7 | 83.3 | | 86.4 | 90 |

The results of the analysis of compositions present in the insoluble corn protein fiber fraction (CPFF) are shown in Table 9. Averages values for proximate analysis of corn and corn gluten meal (CGM), corn gluten feed (CGF) are included along with the analysis of starting endosperm. Data for CGM, CGF and corn are published values by the Corn Refiners Association. Data for DDGS are defined by the American Feed Control Officials Inc., *Official Publication* 2007, as product obtained after the removal of ethyl alcohol by distillation from yeast fermentation of a grain or a grain mixture by condensing and drying at ¾ of solids of the resultant whole stillage using methods employed in the grain distilling industry. University of Minnesota, Department of Animal Sciences, *Comparison Tables for Proximate Analysis of DDGS* (March 2009).

Co-product from this process provides a gluten product containing fiber that has not been subjected to high temperatures during liquefaction as for DDGS or long periods of exposure to sulfur dioxide ($SO_2$) as have the feed products from corn wet milling which is associated with feed off odors. Due to the fact that most of the germ is removed during the de-germination process, the resulting percent fat level is also lower than average DDGS.

Example 9

Use of Different Alpha-Amylases to Degrade Starch in Corn Endosperm

This study provides a comparison of different commercially available thermostable liquefying alpha amylases on the solubilization and production of fermentable sugar during incubation of corn endosperm granular starch at a temperature below the gelatinization temperature of the starch in the corn endosperm.

Materials and Methods

Corn endosperm (Valero Renewable Jefferson Plant, N5355 Junction Rd. Jefferson Wis. 53549) was ground in an MPX mill at minimum clearance to have a particle size distribution of 1.6% on a 590 micron opening sieve, 10% on a 420 micron opening sieve and 88.4% through the 420 micron opening sieve. The moisture content was 14.2%. Aqueous slurry containing 30% ds was made and the pH was adjusted to 5.4 with 6 N HCl. The slurry was dosed with different commercially available thermostable liquefying alpha amylases (shown in Table 9) as per manufacturer's recommended dose. The flasks were then placed in an incubated shaker maintained at 60° C. Samples were withdrawn at different intervals of time during incubation for determination of starch solubilization and HPLC composition for fermentable sugar composition as described in Example 1.

Results

As seen from the results in Table 10, addition of different commercial liquefying alpha amylases resulted in various level of granular starch solubilization. However, all alpha amylases tested produced high levels of fermentable sugar. Without being limited by theory, it is hypothesized that the difference in the fermentable sugar content could be due to the differences in the availability of soluble substrate to endogenous starch hydrolyzing enzymes. For example, lower solubilization generally results in higher percentage of DP1 and DP2.

Example 10

Use of AMY E in the Solubilization of Corn Endosperm

This example examines the effect of AMY E, an endo-acting liquefying and saccharifying alpha amylase, incubated with SPEZYME® RSL on starch solubilization and production of fermentable sugar at a temperature below the gelatinization temperature of the starch in the corn endosperm.

Materials and Methods

Corn endosperm (Valero Renewable Jefferson Plant, N5355 Junction Rd. Jefferson Wis. 53549) was ground in an MPX mill at minimum clearance to have a particle size distribution of 1.6% on a 590 micron opening sieve, 10% on a 420 micron opening sieve, and 88.4% through the 420 micron opening sieve. The moisture content was 14.2%. Aqueous slurry containing 30% ds was made and the pH was adjusted to 5.4 with 6 N HCl. SPEZYME® RSL was added at 6.0 AAU/gds. The slurry was dosed with different amounts of AMY E (01, 0.5 and 1.0 mg of AMY E per gds). The flasks were placed in an incubated shaker maintained at 60° C. Samples were withdrawn at different intervals of time during incubation for determining the starch solubilization and HPLC composition for fermentable sugar composition as described in Example 1.

TABLE 10

Solubility, DP, and percentage fermentable sugars obtained from corn endosperm.

| Commercial product | Supplier | Recommended Dosage for liquefaction | Dosage used in the study | Incubation Time (Hour) | % Solubility | % DP1 | % DP2 | % DP3 | % DP4+ | % Fermentables (DP1 + DP2) |
|---|---|---|---|---|---|---|---|---|---|---|
| SPEZYME ® Xtra | Genencor | 0.2~0.5 KG/MTds corn | 0.26 KG/MTds corn | 48 | 73.6 | 59.31 | 23.61 | 9.53 | 7.55 | 82.9 |
| SPEZYME ® Alpha | Genencor | 0.2~0.5 KG/MTds corn | 0.26 KG/MTds corn | 48 | 64 | 69.07 | 19.83 | 6.14 | 4.97 | 88.9 |
| SPEZYME ® RSL | Genencor | 0.2~0.5 KG/MTds corn | 0.26 KG/MTds corn | 48 | 65.8 | 66.78 | 21.26 | 6.78 | 5.17 | 88.0 |
| Liquozyme ® SC DS | Novozymes | 0.2~0.5 KG/MTds corn | 0.26 KG/MTds corn | 48 | 43.5 | 76.79 | 15.13 | 3.69 | 4.39 | 91.9 |
| Fuelzyme ® LF | Verenium | 0.2~0.5 KG/MTds corn | 0.30 KG/MTds corn | 48 | 24.8 | 71.72 | 11.75 | 3.38 | 13.15 | 83.5 |

Results

TABLE 11

Solubility, DP, and percentage fermentable sugars obtained from corn endosperm.

| Enzymes | % Solubility | % DP1 | % DP2 | % DP3 | % DP4+ | % Fermentables (DP1 + DP2) |
|---|---|---|---|---|---|---|
| No AmyE added | 74.7 | 57.41 | 24.90 | 10.43 | 7.26 | 82.3 |
| 0.1 mg AME Protein/gds | 85.0 | 49.64 | 27.58 | 13.21 | 9.57 | 77.2 |
| 0.5 mg AME Protein/gds | 88.0 | 60.16 | 23.97 | 9.31 | 6.56 | 84.1 |
| 1.0 mg AMY E Protein/gds | 90.5 | 63.99 | 22.53 | 7.88 | 5.6 | 86.5 |

The data in Table 11 shows that the endo-acting liquefying and saccharifying alpha amylase AMY E in combination with SPEZYME® Xtra during the incubation of corn endosperm resulted in high solubilization of the granular corn starch and production of fermentable sugars at levels greater than 85%.

Example 11

Comparison of Commercially Available Corn Endosperms for the Production of Fermentable Sugars This study examined commercially available corn endosperms for their potential to produce fermentable sugars at temperatures below the gelatinization temperature of the starch in the grain.

Materials and Methods

Corn endosperms are currently produced on a commercial scale either for food applications or fuel alcohol production using dry fractionation processes (Alexander, 1987, "Corn Dry Milling: Process, Products, and Applications," in *Corn Chemistry and Technology*, (Watson & Ramstead, eds.; American Association of Cereal Chemists, Inc.), pgs. 351-376), or wet fractionation (U.S. Pat. No. 6,566,125). Both processes produce endosperm containing greater than 80% starch on a dry weight basis. Comparative studies were conducted by making an aqueous slurry containing 30% ds using endosperm (ground and passed through 40-mesh sieve) from two different manufactures: 1) Valero Renewable Jefferson Plant, Jefferson, Wis.; and 2) ICM, Colwich, Kans. After the pH of the slurry was adjusted to 5.4, SPEZYME® XTRA was added at 8 AAU/gds and then incubated at 60° C. for 48 hours. Samples were taken at different intervals time to determine the percent solubilization of the corn granular starch and sugar composition of fermentable sugars as described in Example 1.

Results

TABLE 12

Solubility, DP, and percentage fermentable sugars obtained from different sources of corn endosperm.

| Manufacturer | H-GA | Hour | % Solubility | % DP1 | % DP2 | % DP3 | % DP4+ | % fermentable sugars |
|---|---|---|---|---|---|---|---|---|
| Valero | 0 | 24 | 70.1 | 52.6 | 26.39 | 11.98 | 9.03 | 79.0 |
|  | +H-GA |  | 79.6 | 80.66 | 14.08 | 2.89 | 2.38 | 94.7 |
|  | 0 | 48 | 75.0 | 65.25 | 22.36 | 7.64 | 4.76 | 87.6 |
|  | +H-GA |  | 84.9 | 87.35 | 9.61 | 1.60 | 1.45 | 87.0 |
| ICM | 0 | 24 | 64.0 | 65.77 | 21.05 | 7.37 | 5.82 | 86.8 |
|  | +H-GA |  | 74.8 | 86.08 | 10.29 | 1.59 | 2.04 | 96.4 |
|  | 0 | 48 | 70.4 | 74.9 | 16.82 | 4.72 | 3.57 | 91.7 |
|  | +H-GA |  | 81.1 | 90.06 | 7.48 | 0.86 | 1.6 | 97.5 |

As shown in Table 12, both commercially available samples of corn endosperm produced high levels of fermentable sugars during incubation with SPEZYME® XTRA and *Humicola*-GA.

Example 12

Direct Starch to Fermentable Sugar Using Rice Flour

This example looked at production of DSTFS syrup using an alternative source of starch for starch degradation at temperatures below that of the gelatinization temperature of starch in the grain.

Materials and Methods

An aqueous slurry (30% ds) of rice flour was prepared and the pH was adjusted to pH 5.5. SPEZYME® XTRA and two different glucoamylase preparations were added at different doses and incubated at 60° C. with constant mixing. Samples were taken at different intervals of time during incubation and percent rice starch solubilized and sugar composition of the soluble fractions were determined as described in Example 1.

TABLE 13

DP and percentage of starch solubilized using rice flour as a starch source.

| Treatment | Hrs | % DP1 | % DP2 | % DP3 | % DP4+ | % starch solubilized |
|---|---|---|---|---|---|---|
| Control (SPEZYME ® XTRA 10 AAU/gds) | 19 | 41.125 | 32.552 | 18.121 | 8.202 | 80.01 |
| | 26 | 42.758 | 32.019 | 17.475 | 7.749 | 82.73 |
| | 43 | 48.000 | 29.648 | 15.510 | 6.842 | 89.67 |
| | 48 | 49.463 | 28.984 | 14.941 | 6.611 | 89.96 |
| SPEZYME ® XTRA 10U/gds + DISTILLASE ASP, 0.1GAU/gds | 19 | 69.008 | 22.500 | 6.992 | 1.500 | 83.28 |
| | 26 | 72.679 | 20.431 | 6.889 | 0.000 | 84.37 |
| | 43 | 78.058 | 17.017 | 4.925 | 0.000 | 90.52 |
| | 48 | 79.345 | 16.128 | 4.527 | 0.000 | 91.94 |
| SPEZYME ® 10AAU/gds + DISTILLASE ® ASP, 0.3GAU/gds | 19 | 82.423 | 14.346 | 3.231 | 0.000 | 87.71 |
| | 26 | 84.641 | 12.747 | 2.612 | 0.000 | 92.51 |
| | 43 | 87.276 | 10.684 | 2.039 | 0.000 | 93.66 |
| | 48 | 87.630 | 10.213 | 2.157 | 0.000 | 94.81 |
| SPEZYME ® XTRA 10AAU/gds + DISTILLASE ® ASP, 0.5GAU/gds | 19 | 86.166 | 11.601 | 2.233 | 0.000 | 90.52 |
| | 26 | 87.475 | 10.623 | 1.902 | 0.000 | 97.13 |
| | 43 | 88.813 | 9.541 | 1.646 | 0.000 | 99.77 |
| | 48 | 88.976 | 9.399 | 1.626 | 0.000 | 98.59 |
| SPEZYME ® XTRA 10AAU/gds + H-GA-0.1GAU/gds | 19 | 75.259 | 18.316 | 6.425 | 0.000 | 87.43 |
| | 26 | 78.749 | 16.188 | 5.063 | 0.000 | 90.24 |
| | 43 | 82.668 | 13.568 | 3.764 | 0.000 | 93.08 |
| | 48 | 83.430 | 13.012 | 3.558 | 0.000 | 94.81 |
| SPEZYME ® XTRA 10AAU/gds + H-GA, 0.3GAU/gds | 19 | 87.523 | 10.326 | 2.151 | 0.000 | 88.27 |
| | 26 | 89.018 | 9.308 | 1.674 | 0.000 | 91.94 |
| | 43 | 90.239 | 8.345 | 1.416 | 0.000 | 94.23 |
| | 48 | 90.471 | 8.181 | 1.349 | 0.000 | 96.26 |
| SPEZYME ® XTRA, 10AAU/gds + H-GA, 0.5GAU/gds | 19 | 90.793 | 7.927 | 1.280 | 0.000 | 93.08 |
| | 26 | 91.297 | 7.621 | 1.081 | 0.000 | 95.97 |
| | 43 | 91.425 | 7.514 | 1.061 | 0.000 | 98.89 |
| | 48 | 91.379 | 7.570 | 1.052 | 0.000 | 99.47 |

The results in Table 13 show the complete solubilization of the rice starch at high concentrations of glucoamylase with 10 AAU of SPEZYME® XTRA and the solubilized starch contained greater than 98% DP1 and DP2 sugars.

Example 13

Direct Starch to Fermentable Sugar Using Whole Ground Wheat

This example describes the direct conversion of wheat granular starch to fermentable sugars production using whole ground wheat as a substrate.
Materials and Methods
Whole ground wheat (32% ds) was hydrolyzed using only SPEZYME™ XTRA (*B. stearothermophilus* alpha-amylase (AA)) in one experiment and 2 combinations of SPEZYME™ XTRA and *Humicola*-glucoamylase (GA) in another. Sugar profiles were obtained from the hydrolysis of whole ground wheat by endogenous wheat enzymes, alpha-amylase, and/or combinations of AA/GA. The Alpha-Amylase was dosed at 9 AAU/gr ds and the *Humicola* GA either at 0.05 GAU/gr ds or 0.1 GAU/gr ds. A negative control was also measured to monitor the endogenous enzyme activity of wheat. Conditions were 32% DS, 60° C., pH 5.2, 9 AAU/g ds SPEZYME™ XTRA; 9 AAU/g ds SPEZYME™ XTRA and 0.05 GAU/gr ds *Humicola* GA; 9 AAU/g ds SPEZYME™ XTRA and 0.1 GAU/gr ds *Humicola* GA; or endogenous wheat enzymes (negative control), respectively, for each experimental trial run. Samples were withdrawn at different time intervals during the hydrolysis for HPLC analysis and the measurement of starch solubilization as described in Example 1.
Results

TABLE 14

Solubility, DP, and percentage fermentable sugars obtained.

| Pretreatment | Hour | % Starch Solubility | % DP1 | % DP2 | % DP3 | % DP4+ | % fermentable sugars |
|---|---|---|---|---|---|---|---|
| 9 AAU/g SPEZYME ™ XTRA | 0 | 16.7 | 23.8 | 17.6 | 0.9 | 57.7 | 41.4 |
| | 5 | 89.3 | 3.8 | 58.7 | 10.7 | 26.8 | 62.5 |
| | 21.5 | 96.3 | 5.0 | 61.6 | 15.7 | 17.7 | 66.6 |
| | 27 | 96.1 | 5.3 | 62.0 | 16.6 | 16.2 | 67.3 |

TABLE 14-continued

Solubility, DP, and percentage fermentable sugars obtained.

| Pretreatment | Hour | % Starch Solubility | % DP1 | % DP2 | % DP3 | % DP4+ | % fermentable sugars |
|---|---|---|---|---|---|---|---|
| | 44.5 | 99.8 | 5.6 | 62.7 | 18.4 | 13.3 | 68.3 |
| | 48 | 99.8 | 5.5 | 62.9 | 18.7 | 12.9 | 68.4 |
| 9 AAU/g | 0 | 14.7 | 25.0 | 14.6 | 1.4 | 59.0 | 39.6 |
| SPEZYME ™ | 5 | 90.1 | 23.2 | 50.6 | 3.1 | 23.1 | 73.8 |
| XTRA + | 21.5 | 94.5 | 57.3 | 27.6 | 3.6 | 11.6 | 84.9 |
| 0.05 GAU/g | 27 | 97.0 | 63.5 | 22.9 | 3.7 | 9.9 | 86.4 |
| *Humicola* GA | 44.5 | 94.8 | 77.4 | 11.9 | 3.8 | 6.9 | 89.3 |
| | 48 | 98.6 | 78.9 | 10.6 | 3.8 | 6.7 | 89.5 |
| 9 AAU/g | 0 | 15.6 | 23.5 | 17.1 | 1.8 | 57.5 | 40.6 |
| SPEZYME ™ | 5 | 90.7 | 19.7 | 53.1 | 3.6 | 23.6 | 72.8 |
| XTRA + | 21.5 | 96.9 | 49.3 | 34.2 | 3.6 | 12.9 | 83.5 |
| 0.1 GAU/g | 27 | 97.6 | 55.1 | 29.9 | 3.8 | 11.2 | 85 |
| *Humicola* GA | 44.5 | 95.0 | 68.8 | 18.9 | 4.1 | 8.2 | 87.7 |
| | 48 | 100.0 | 71.0 | 17.2 | 4.1 | 7.8 | 88.2 |
| Endogenous | 0 | 16.6 | 22.9 | 21.0 | 1.5 | 54.6 | 43.9 |
| wheat | 5 | 74.8 | 3.6 | 50.7 | 3.9 | 41.8 | 54.3 |
| enzymes | 21.5 | 79.8 | 4.5 | 50.9 | 7.5 | 37.1 | 55.4 |
| (negative | 27 | 79.6 | 4.8 | 51.2 | 8.2 | 35.8 | 56 |
| control) | 44.5 | 82.9 | 4.5 | 50.9 | 9.8 | 34.9 | 55.4 |
| | 48 | 80.3 | 4.5 | 50.9 | 9.9 | 34.7 | 55.4 |

The data in Table 14 demonstrates that, with the single addition of a high dosage of alpha-amylase, more than 65% of fermentable sugars (DP1+DP2) are produced after 21.5 hrs. Starch solubility is greater than 95% after 21.5 hrs of hydrolysis.

The addition of 0.05 GAU/g ds Gluco-Amylase in combination with the AA results in greater than 80% of fermentable sugars after 21.5 hrs and greater than 89% fermentable sugars after 44.5 hrs. Starch hydrolysis is greater than 95% after 27 hrs of hydrolysis.

Where Gluco-Amylase levels were increased to 0.1 GAU/g ds, greater than 80% fermentable sugars were released after 21.5 hrs and greater than 88% after 48 hrs. Starch hydrolysis is greater than 95% after 21.5 hrs of hydrolysis. The negative control experiment shows that endogenous wheat enzymes are capable of releasing 55% of the fermentable sugars after 21.5 hrs and obtaining a starch hydrolysis of greater than 80% after 44.5 hrs.

Example 14

Direct Conversion of Barely Granular Starch to Fermentable Sugars

This Example describes the direct conversion of barley granular starch to fermentable sugars production using whole barley as a substrate at a temperature below that of the gelatinization temperature of the starch in the barley.

Whole barley is steeped and then milled and an aqueous slurry containing 32% ds is prepared. The pH of the slurry is adjusted to pH 5.25 and incubated with only SPEZYME™ XTRA (*B. stearothermophilus* AA) in one experiment and a combination of SPEZYME™ XTRA and *Humicola*-GA in another. The Alpha-Amylase is dosed at 8 AAU/gds and the *Humicola*-GA at 0.05 GAU/gds. The hydrolysis is performed at 60° C. and at pH 5.25. Samples are withdrawn at different time intervals during the hydrolysis for HPLC analysis and the measurement of starch solubilization performed as described in Example 1.

Example 15

Fermentation of Feedstock Produced by DSTFS

This example examined the fermentation of sugar syrups produced using the method described in Example 7 to produce ethanol as a fermentation product.

Materials and Methods

Sugar syrup produced according to the process described in Example 7 was thawed in a 75° C. water bath and allowed to cool to room temperature. The syrup was then adjusted to a final dry solids content of 22% but had corn steep liquor added at 0.1% solids. Urea (1,200 ppm) and corn steep liquor (0.1% ds) were added as nutrients for the yeast used for the fermentation. Another flask was set up without added corn steep liquor as control. The pH of the medium was adjusted to pH 5.0 and inoculated with active yeast (Ethanol Red, Red Star Yeast). Additional glucoamylase was also added at 0.1 GAU/gds (DISTILLASE® SSF from Genencor, Danisco). Yeast fermentation was carried out by incubating at 32° C., and shaken at 150 rpm. Samples were taken during different intervals of time and analyzed by HPLC.

TABLE 15

Yeast fermentation of feedstock produced by DSTFS into ethanol.

| Flask | Description | hrs | % W/V DP > 3 | % W/V DP-3 | % W/V DP-2 | % W/V DP-1 | % W/V Lactic | % W/V Glycerol | % W/V Acetic | % V/V Ethanol |
|---|---|---|---|---|---|---|---|---|---|---|
| 1, 2 | Fermentable syrup | 0 | 0.254 | 0.158 | 0.565 | 22.057 | 0.000 | 0.000 | 0.000 | 0.000 |
| 1, 2 | Urea | 16 | 0.116 | 0.180 | 0.919 | 21.209 | 0.000 | 0.199 | 0.141 | 0.740 |
| 1, 2 | | 24 | 0.018 | 0.051 | 0.580 | 19.656 | 0.089 | 0.354 | 0.143 | 1.149 |
| 1, 2 | | 40 | 0.019 | 0.054 | 0.582 | 18.611 | 0.000 | 0.421 | 0.157 | 1.592 |

TABLE 15-continued

Yeast fermentation of feedstock produced by DSTFS into ethanol.

| Flask | Description | hrs | % W/V DP > 3 | % W/V DP-3 | % W/V DP-2 | % W/V DP-1 | % W/V Lactic | % W/V Glycerol | % W/V Acetic | % V/V Ethanol |
|---|---|---|---|---|---|---|---|---|---|---|
| 1, 2 | | 48 | 0.012 | 0.049 | 0.547 | 17.096 | 0.000 | 0.419 | 0.141 | 1.582 |
| 3, 4 | Fermentable syrup | 0 | 0.254 | 0.158 | 0.565 | 22.057 | 0.000 | 0.000 | 0.000 | 0.000 |
| 3, 4 | GA | 16 | 0.006 | 0.052 | 0.562 | 20.355 | 0.075 | 0.250 | 0.165 | 0.747 |
| 3, 4 | Urea | 24 | 0.000 | 0.051 | 0.561 | 19.541 | 0.000 | 0.324 | 0.162 | 1.160 |
| 3, 4 | | 40 | 0.007 | 0.055 | 0.550 | 18.518 | 0.067 | 0.483 | 0.158 | 1.586 |
| 3, 4 | | 48 | 0.011 | 0.053 | 0.541 | 17.900 | 0.000 | 0.460 | 0.159 | 1.684 |
| 5, 6 | Syrup + GA + liquor | 0 | 0.355 | 0.169 | 0.579 | 22.636 | 0.326 | 0.000 | 0.000 | 0.000 |
| 5, 6 | Syrup + GA + liquor | 16 | 0.119 | 0.092 | 0.725 | 8.730 | 0.396 | 0.759 | 0.000 | 7.488 |
| 5, 6 | Syrup + GA + liquor | 24 | 0.060 | 0.057 | 0.598 | 0.095 | 0.310 | 1.027 | 0.000 | 12.585 |
| 5, 6 | Syrup + GA + liquor | 40 | 0.044 | 0.038 | 0.468 | 0.011 | 0.067 | 1.026 | 0.079 | 12.767 |
| 5, 6 | Syrup + GA + liquor | 48 | 0.019 | 0.033 | 0.541 | 0.011 | 0.040 | 1.027 | 0.105 | 12.773 |

The results are shown in Table 15. High fermentable sugar syrup was unable to support the growth of yeast during fermentation with only added urea as nutrient. However, the addition of corn steep liquor resulted in complete conversion of fermentable sugars into ethanol in 24 hours of the fermentation. Addition of glucoamylase did not show any additional benefits in terms of ethanol yield.

Example 16

Conversion of DSTFS Feed Stock in Lactic Acid Fermentation

This example used sugar syrup from whole ground corn produced using the direct starch to fermentable sugars (DSTFS) process as a feedstock for fermentation of the syrup into lactic acid.

Materials and Methods

The DSTFS feed stock was prepared by incubating an aqueous slurry of whole ground corn (18% ds) at pH 5.0 with SPEZYME® ALPHA (8.0 AAU/gds) and Humicola-GA (0.1 GAU/gds) at 60° C. for 45 hours. The slurry was then centrifuged to separate the insoluble solids. The soluble solids fraction contained 96.5% fermentable sugars and was used in lactic acid fermentation. The lactic acid fermentation was carried out using Lactobacillus rhamnosus strain obtained from China General Microbiological Culture Collection Center.

Seed Medium:

Casein 10.0 g, Beef extract 10.0 g, Yeast extract 5.0 g, Glucose 5.0 g, Sodium acetate 5.0 g, Diammonium citrate 2.0 g, Tween 80 1.0 g, $K_2HPO_4$ 2.0 g, $MgSO_4$* 7H2O, 0.2 g, $MnSO_4$*$H_2O$ 0.05 g, Agar 15.0 g, Distilled water 1.0 L, pH 6.8. To one thousand grams of fermentation feed stock in a two liter fermenter, the following nutrients were added: 40 g corn steep liquor, 10 g casein, 10 g yeast extract, 10 g beef extract, 1.5 g Tween 80, 0.3 g $MgSO_4$*$7H_2O$, 20 g $CaCO_3$.

The inoculums of Lactobacillus rhamnosus were transferred to 100 mL seed culture and cultivated at 37° C. at 200 rpm. The cultivation was controlled based on OD600 (absorbance) value increasing up 0.5.

50 mL of seed culture was added to a 2 L fermenter. The fermentation was carried out at a constant pH 6.5 using 20% $NH_4OH$ and the temperature was set at 45° C., and the agitation was 200 rpm. Samples were taken for HPLC analysis at 4 hr, 21 hr, 27 hr, and 44 hr. The fermentation was also carried out by adding additional glucoamylase (0.1 GAU/gds). Lactic acid content was calculated according to lactic acid standard concentration as shown in Table 17.

Results

TABLE 16

Production of lactic acid using a DSTFS feedstock. Concentrations are in g/L.

| Sample # | Fermentations | Ferm. Time Hour | DP3+ grams/Liter | DP3 grams/Liter | DP2 grams/Liter | Glucose grams/Liter | Lactic Acid grams/Liter |
|---|---|---|---|---|---|---|---|
| | DSTFS | 0 | 3.4 | 1.8 | 11.5 | 158.5 | 0 |
| 1 | DSTFS | 4 | 3.8 | 1.9 | 9.1 | 141.1 | 10.07 |
| | DSTFS + GA | | 3.1 | 1.8 | 5.6 | 137.1 | 10.07 |
| 2 | DSTFS | 21 | 4.5 | 3.3 | 8.6 | 40.1 | 94.1 |
| | DSTFS + GA | | 3.6 | 1.7 | 7.3 | 88.5 | 53.81 |
| 3 | DSTFS | 27 | 5.7 | 3.6 | 8.3 | 20.6 | 111.13 |
| | DSTFS + GA | | 5.2 | 1.7 | 9 | 50.2 | 88.47 |
| 4 | DSTFS | 44 | 5.7 | 3.6 | 7.2 | 0 | 123.24 |
| | DSTFS + GA | | 5.5 | 1.8 | 8.5 | 0.9 | 128.57 |

Results are shown in Table 16. The fermentable sugar syrup produced by the DSTFS process yielded greater than 123 grams per liter lactic acid. Addition of glucoamylase during fermentation resulted in higher level of lactic acid compared to control without added glucoamylase.

Example 17

Conversion of DSTFS Feedstock into Succinic Acid

This example used sugar syrup from whole ground corn produced using the direct starch to fermentable sugars (DSTFS) process as a feedstock for fermentation of the syrup into succinic acid.

The fermentable sugars feed stock used in this example is prepared as explained in Example 13 by incubating an aqueous slurry of whole ground corn (18% ds) at pH 5.0 with SPEZYME ALPHA 9.8 AAU/gds and *Humicola*-GA (0.1 GAU/gds) at 60° C. for 45 hours. The slurry is then centrifuged to separate the insoluble solids. The soluble fraction contained 96.5% fermentable sugars and is then used in Succinic acid fermentation.

Succinic acid fermentation utilized *Actinobacillus succinogenes* 130Z (ATCC 55618) from China General Microbiological Culture Collection Center. The TSB medium is inoculated with the bacterial strain in cooked meat medium. The culture incubated at 37° C. for 8 hr. Then, the activated strain in TSB medium is inoculated in seed medium, which is incubated at 37° C. for 16 hr under anaerobic conditions. Finally, after adding $MgCO_3$ powder the seeds strain is inoculated in fermentation medium. The fermentation is conducted under anaerobic conditions with $CO_2$ atmosphere for 48 hr. Fermentation broth is analyzed by HPLC, illustrating the successful generation of succinic acid.

Example 18

Effect of Alpha-Amylase Concentration on the Production of Kojibiose and Nigerose The experiments in this example were conducted to demonstrate production of kojibiose and nigerose by exogenous alpha-amylase with whole ground corn.
Materials and Methods Aqueous whole ground corn was mixed with DI water in order to produce a 32% dry solids slurry and adjusted to pH 5.6 with HCl. The slurry (150 g) was then placed in 4 different 250 ml plastic bottles and incubated in a shaker (210 rpm) at 60° C. with 4, 8, 12 or 16 AAU/gds of SPEZYME® XTRA.

Solubilization/Saccharification was carried out up to 48 hours and samples from each jar were periodically drawn. Samples were then centrifuged to obtain supernatant for RI (Refractive Index) for calculating percent solubility and diluted by taking 0.5 ml and combining it with 4.5 ml of RO water. This was then filtered through 0.45 μm Whatman filters and put into vials for HPLC analysis. The HPLC analysis was conducted using a Rezex RCM-Monosaccharide column with a guard column for sugar composition. Further analysis for DP2 composition was carried out by capillary electrophoresis, which was confirmed by NMR (not shown).
Results This experiment shows that higher concentrations of alpha-amylase solubilized more starch in corn, generating high levels of DP1 and DP2. In all cases, significant amount of Kojibiose and Nigerose were successfully produced. The results suggest that endogenous starch hydrolyzing enzyme in corn can produce glucose as well as the disaccharides isomaltose, kojibiose and nigerose from solubilized starch.

Example 19

Effect of Temperature on the Production of Kojibiose and Nigerose

This example shows the temperature effect on the hypothesized endogenous plant starch hydrolyzing enzymes in whole ground corn.
Materials and Methods Aqueous whole ground corn slurry was prepared by mixing with DI water in order to contain 32% dry solids and adjusted to pH 5.6 with HCl. Each 150 g of the slurry was then placed in 4 different 250 ml plastic bottles and placed either in a top-stirring waterbath at 70° C. or 83° C. or a shaker at 50° C. or 60° C. with 10 AAU/gds of SPEZYME® XTRA. After a 2 hour incubation, the slurries were put into a 60° C. shaking incubator to continue the reaction, while the slurries at 50° C. and 60° C. were maintained without temperature shift.

Solubilization/Saccharification was carried out up to 48 hours and samples from each jar were periodically drawn. Samples were then centrifuged to obtain supernatant for RI (Refractive Index) for calculating percent solubility and diluted by taking 0.5 ml and combining it with 4.5 ml of RO water. This was then filtered through 0.45 μm Whatman filters and put into vials for HPLC analysis. The HPLC analysis was conducted using a Rezex RCM-Monosaccharide column with a guard column for sugar composition. Further analysis for DP2 composition was carried out by capillary electrophoresis, which was confirmed by NMR (not shown).

TABLE 17

Concentration of DP2 saccharides following solubilization with alpha-amylase at temperatures below the initial gelatinization temperature of the grain.

| SPEZYME® XTRA (AAU/gds) | % starch solubilized | % dry solids | % sugar composition | | | | DP2 grams/100 gram dry solids | | | |
|---|---|---|---|---|---|---|---|---|---|---|
| | | | DP1 | DP2 | DP3 | DP4+ | Maltose | Isomaltose | Kojibiose | Nigerose |
| 4 | 72.9 | 24.9 | 67.86 | 20.48 | 6.75 | 4.91 | 10.74 | 3.35 | 4.14 | 2.25 |
| 8 | 80.3 | 26.8 | 65.17 | 21.70 | 7.72 | 5.42 | 9.64 | 4.37 | 5 | 2.69 |
| 12 | 84 | 27.8 | 63.83 | 22.37 | 8.55 | 5.58 | 9.97 | 4.2 | 5.36 | 2.84 |
| 16 | 86.4 | 28.3 | 62.59 | 22.95 | 8.70 | 5.76 | 11.36 | 3.71 | 5.05 | 2.83 |

Results

TABLE 18

Concentration of DP2 saccharides following solubilization with alpha-amylase at varied temperatures.

| Temp °C. | SPEZYME® XTRA | % starch solubilized | % dry solids | % sugar composition | | | | DP2 grams/100 gram dry solids | | | |
|---|---|---|---|---|---|---|---|---|---|---|---|
| | | | | DP1 | DP2 | DP3 | DP4+ | Maltose | Isomaltose | Kojibiose | Nigerose |
| 50 | 10AAU/gds | 44.6 | 16.7 | 84.38 | 7.27 | 1.54 | 6.82 | 3.2 | 2.75 | 0.9 | 0.42 |
| 60 | 10AAU/gds | 81 | 27 | 65.17 | 21.85 | 7.80 | 5.19 | 12.78 | 3.19 | 3.81 | 2.07 |
| 70 | 10AAU/gds | 68.9 | 23.8 | 19.32 | 30.65 | 23.63 | 26.40 | 28.21 | 0.34 | 1.22 | 0.88 |
| 83 | 10AAU/gds | 100 | 31.57 | 2.43 | 5.55 | 6.82 | 85.19 | 5.31 | 0.06 | 0.09 | 0.09 |

These data show that significant amounts of kojibiose/nigerose was successfully produced by solubilizing granular starch of corn with SPEZYME® XTRA. These data also show that the hypothesized endogenous enzymes are most active at 60° C. Temperatures at 70° C. and higher appear to inactivate the enzymes, leaving significantly lower level of kojibiose and nigerose. The productivity of these DP2 appeared to be not dependent on the concentration of AAU.

Example 20

DP2 Compositions from Different Grains

This example examined the ability of different small grains to produce Kojibiose/Nigerose.
Materials and Methods Aqueous slurries of 5 different ground grains: (A) whole ground corn, (B) dehulled ground milo, (C) ground wheat, (D) ground barley and (E) rye flour, were prepared by mixing with DI water in order to produce a 32% dry solids slurry and adjusted to pH 5.6 for milo and pH 5.9 for wheat, barley and rye with HCl, respectively. Then, each slurry (150 g) from the respective grain was placed in 8 different 250 ml plastic bottles and incubated in the shaker at 60 C with 10 AAU/gds of SPEZYME® XTRA dose. In the cases of wheat, barley and rye, 0.05 GAU/gds of H-GA was dosed in addition because a high level of maltose was expected to be produced.

Solubilization/Saccharification was carried out up to 48 hours and samples from each jar were periodically drawn. Samples were then centrifuged to obtain supernatant for RI (Refractive Index) for calculating percent solubility and diluted by taking 0.5 ml and combining it with 4.5 ml of RO water. This was then filtered through 0.45 μm Whatman filters and put into vials for HPLC analysis. The HPLC analysis was conducted using a Rezex RCM-Monosaccharide column with a guard column for sugar composition. Further analysis for DP2 composition was carried out by capillary electrophoresis, which was confirmed by NMR (not shown).
Results

TABLE 19

Concentration of DP2 saccharides following solubilization of different grains with alpha-amylase.

| SPEZYME® XTRA AAU/gds | Substrates | % starch solubilized | % dry solids | % sugar composition | | | | DP2 grams/100 gram dry solids | | | |
|---|---|---|---|---|---|---|---|---|---|---|---|
| | | | | DP1 | DP2 | DP3 | DP4+ | Maltose | Isomaltose | Kojibiose | Nigerose |
| 10 | Corn | 81 | 27 | 65.17 | 21.85 | 7.80 | 5.19 | 12.78 | 3.19 | 3.81 | 2.07 |
| 10 | Milo | 83 | 28.1 | 70.24 | 18.42 | 6.39 | 4.94 | 1.55 | 8.08 | 1.99 | 1.02 |
| 10 | Wheat | 88.7 | 27.3 | 6.09 | 70.96 | 12.63 | 10.13 | 70.96 | ND | ND | ND |
| Add H-GA (0.05GAU/gds) | Wheat | 94.8 | 28.7 | 78.21 | 11.42 | 3.77 | 6.60 | 11.42 | ND | ND | ND |
| 10 | Barley | 86.1 | 26.6 | 9.18 | 51.00 | 12.42 | 27.41 | 51 | ND | ND | ND |
| Add H-GA (0.05GAU/gds) | Barley | 95.5 | 28.7 | 73.26 | 9.99 | 4.29 | 12.46 | 9.99 | ND | ND | ND |
| 10 | Rye | 93.2 | 30.67 | 10.40 | 45.68 | 17.28 | 26.64 | 45.68 | ND | ND | ND |
| Add H-GA (0.05GAU/gds) | Rye | 95.8 | 31.29 | 75.50 | 7.93 | 4.96 | 11.60 | 7.93 | ND | ND | ND |

ND = Not detectable

These data indicate that only corn and milo contain the hypothesized endogenous plant starch hydrolyzing enzymes to produce unique DP2s such as Isomaltose, Kojibiose and Nigerose, whereas other grains (wheat, barley and rye) only produced maltose, presumably driven by endogenous beta-amylase.

Example 21

Production of Kojibiose/Nigerose from Granular Starch Using Extracts from Whole Ground Corn Slurry This example was conducted to demonstrate extractability of endogenous enzymes from whole ground corn and their capability to produce Kojibiose and Nigerose from refined corn starch.
Materials and Methods Aqueous whole ground corn slurry was prepared by mixing with DI water in order to form a slurry with 30% dry solids and adjusted to pH 5.6 with HCl. Then each 150 g of the slurry was placed in a plastic bottle and let them undergo at 37° C. in the shaker. After a 3 hour incubation, the slurries were centrifuged to remove heavy solids and the resulting supernatant (extract) was recovered. 10% dry solids refined corn starch slurry was then prepared using the supernatant to incubate at 55° C. in a shaking incubator with and without 10 AAU/gds of SPEZYME® XTRA. The pH of the slurry was adjusted to 5.6 before dosing enzyme. Incubation was carried out up to 47 hours and samples were taken at 24 and 47 hours.

Samples were then centrifuged to obtain supernatant for RI (Refractive Index) for calculating percent solubility and diluted by taking 0.5 ml and combining it with 4.5 ml of RO water. This was then filtered through 0.45 μm Whatman filters and put into vials for HPLC analysis. The HPLC analysis was conducted using a Rezex RCM-Monosaccharide column with a guard column for sugar composition. Further analysis for DP2 composition was carried out by capillary electrophoresis.
Results As observed in Table 20, a significant amount of kojibiose/nigerose was successfully produced by solubilizing granular starch of corn with whole ground corn slurry extract and SPEZYME® XTRA, while there was negligible amount of kojibiose/nigerose when SPEZYME XTRA® added. The results showed that endogenous enzyme is soluble can be extracted with water. Additionally, the results indicate that water-extractable endogenous enzyme is capable of producing kojibiose and nigerose.

Example 22

Effect of pH Treatment of Whole Ground Corn Slurry on Reduction of Kojibiose/Nigerose This example was conducted to demonstrate the effect of pH on endogenous plant starch hydrolyzing enzymes in whole ground corn and to propose a method to inactivate endogenous enzymes.
Materials and Methods Aqueous whole ground corn slurry was prepared by mixing with DI water in order to contain 32% dry solids. The slurry was then split into 2 groups: one is maintained at pH 5.5 and the other adjusted to pH 3.0 with HCl, followed by incubation at 60° C. for 1 hour in the shaking incubator. The slurry without pH adjustment is incubated at 60° C. in a shaking incubator, while the slurry at pH 3.0 was pH-adjusted back to pH 5.6 to continue the incubation.

The reaction was carried out up to 22 hours and samples were then centrifuged to obtain supernatant for RI (Refractive Index) for calculating percent solubility and diluted by taking 0.5 ml and combining it with 4.5 ml of RO water. This was then filtered through 0.45 μm Whatman filters and put into vials for HPLC analysis. The HPLC analysis was conducted using a Rezex RCM-Monosaccharide column with a guard column for sugar composition. Further analysis for DP2 composition was carried out by capillary electrophoresis.

TABLE 20

Concentration of DP2 saccharides following solubilization of refined corn starch slurry.

| Hour | SPEZYME® XTRA | % dry solids | % sugar composition | | | | | DP2 grams/100 gram dry solids | | | |
|---|---|---|---|---|---|---|---|---|---|---|---|
| | | | Fructose | Unknown | DP1 | DP2 | DP3 | DP4+ | Maltose | Isomaltose | Kojibiose | Nigerose |
| 24 | No enzyme | 4.3 | 26.68 | 2.14 | 54.07 | 3.24 | 7.16 | 5.43 | Not measurable | | | |
| 47 | No enzyme | 3.7 | 24.34 | 2.68 | 51.71 | 3.97 | 9.60 | 7.71 | | | | |
| 24 | 10AAU/gds | 13.0 | 3.67 | 0.39 | 49.08 | 23.72 | 9.77 | 13.38 | 71 | 15 | 7 | 8 |
| 47 | 10AAU/gds | 13.1 | 3.45 | 0.69 | 64.62 | 18.63 | 6.64 | 5.85 | 51 | 24 | 11 | 14 |

Results

TABLE 21

Concentration of DP2 saccharides following solubilization with and without pre-pH treatment.

| pH pre-treatment | SPEZYME® XTRA | H-GA | % starch solubilized | % dry solids | % sugar composition | | | | DP2 grams/100 gram dry solids | | | |
|---|---|---|---|---|---|---|---|---|---|---|---|---|
| | | | | | DP1 | DP2 | DP3 | DP4+ | Maltose | Isomaltose | Kojibiose | Nigerose |
| No | 10AAU/gds | 0.1GAU/gds | 79.6 | 26.1 | 87.34 | 9.32 | 1.36 | 1.97 | 27.4 | 26.3 | 31.5 | 14.8 |
| 3.0 | 10AAU/gds | 0.1GAU/gds | 79.3 | 25.1 | 90.55 | 2.94 | 1.55 | 4.96 | 89.0 | 11.0 | 0 | 0 |

The data demonstrate that endogenous enzymes were inactivated during pre-treatment at pH 3.0 in terms of formation of kojibiose and nigerose. Additionally, the results show that the resulting syrup contains higher DP1 and lower DP2, providing more fermentability.

Example 23

Conversion of DSTFS Feedstock into Mevalonic Acid (MVA)

This example uses glucose syrup obtained by the DSTFS process for the microbial production of mevalonic acid. R-Mevalonate is an intermediate of the mevalonate-dependent biosynthetic pathway that converts acetyl-CoA to isopentenyl diphosphate and dimethylallyl diphosphate. Commercially, mevalonate has been used as an additive in cosmetics, for the production of biodegradable polymers, and can have value as a chiral building block for the synthesis of other chemicals.

The products of the mevalonate-dependent pathway are isopentenyl pyrophosphate (IPP) and dimethylallyl diphosphate (DMAPP). IPP and DMAPP are precursors to isoprene as well as isoprenoids. Isoprene (2-methyl-1,3-butadiene) is the monomer of natural rubber and also a common structural motif to an immense variety of other naturally occurring compounds, collectively termed the isoprenoids. Isoprene is additionally the critical starting material for a variety of synthetic polymers, most notably synthetic rubbers.

Materials and Methods

Fermentation was performed in a fed-batch culture in a 15-L bioreactor using a transformed cell line of *E. coli* BL21, labeled MCM1375 (see Table 22), which over expresses the enzymes of the upper mevalonate pathway. Cells were grown and Mevalonic acid (MVA) analyzed using the following methods.

TABLE 22

List of mevalonate-producing strains.

| | |
|---|---|
| CMP680 | HMB GI 1.2 gltA ML ackA-pta ldhA attB::Cm, pCLPtrcUpper(rbs) (pCHL276)) |
| MCM1373 | HMB GI 1.2 gltA ML ackA-pta ldhA attB::Cm + pCL-Ptrc-Upper_Ef |
| MCM1374 | HMB GI 1.2 gltA ML ackA-pta ldhA attB::Cm + pCL-Ptrc-Upper_Ec |
| MCM1375 | HMB GI 1.2 gltA ML ackA-pta ldhA attB::Cm + pCL-Ptrc-Upper_Listeria |
| MCM1376 | HMB GI 1.2 gltA ML ackA-pta ldhA attB::Cm + pCL-Ptrc-Upper_Efaecium |
| MCM1377 | HMB GI 1.2 gltA ML ackA-pta ldhA attB::Cm + pCL-Ptrc-Upper_Eg |

1000× Trace Metal Solution (Per Liter):

Citric Acids*$H_2O$ 40 g, $MnSO_4$*$H_2O$ 30 g, NaCl 10 g, $FeSO_4$*$7H_2O$ 1 g, $CoCl_2$*$6H_2O$ 1 g, $ZnSO$*$7H_2O$ 1 g, $CuSO_4$*$5H_2O$ 100 mg, $H_3BO_3$ 100 mg, $NaMoO_4$*$2H_2O$ 100 mg. Each component was dissolved one at a time in Di $H_2O$, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, D-pantothenic acid 4.8 g, pyridoxine hydrochloride 4.0 g. Each component was dissolved one at a time in Di $H_2O$, pH was adjusted to 3.0 with HCl/NaOH, and then the solution was q.s. to volume and filter sterilized with 0.22 micron filter.

Macro Salt Solution (Per Liter):

$MgSO_4$*$7H_2O$ 296 g, citric acid monohydrate 296 g, ferric ammonium citrate 49.6 g. All components were dissolved in water, q.s. to volume and filter sterilized with 0.22 micron filter.

Feed Solution (Per Kilogram):

DSTFS syrup 984 g, $K_2HPO_4$ 7.4 g, and 100% Foamblast 8.9 g. All components were mixed together and autoclaved. The DSTFS syrup solution had a concentration, as measured by refractive index, of 48% (w/w).

Production of DSTFS Syrup:

Grind corn (40 kg) was mixed into 60 kg water. This solution was mixed for 1 hr at room temperature (RT) with agitation. The mixture pH was adjusted with 10% sulfuric acid to yield a pH of 5.3-5.5. To this mixture was added 13.7 mg of SPEZYME® RSL (Genencor Intl., Palo Alto, Calif.) and 880 µg of TrGA enzyme. The solution was allowed to incubate at RT for 30 min. The temperature was sequentially ramped to 60° C. over a 30 min timeframe and allowed to incubate for 48 hr. The mixture's pH was monitored and maintained at 5.3-5.5. Syrup separation was achieved via addition of 2% Dicalite 476 into the slurry and filtration through a K900 pad under 10 psi of pressure. Syrup evaporation was achieved via a heat ramp to 90° C. Analysis for degree of polymerization of the syrup was performed as above and the results shown in Table 23.

A frozen vial of the *E. coli* strain was thawed and inoculated into tryptone-yeast extract medium for the bioreactor. Cells were grown at 30° C. to an optical density of about 1.0, measured at 550 nm ($OD_{550}$), 500 mL was used to inoculate a 15-L bioreactor and bring the initial tank volume to 5 L. Spectinomycin was used as a selective antibiotic at a concentration of 50 ug/mL in the seed flask and fermentation tank. These steps were carried out at pH 7.0 and 34° C. Induction of genes was achieved by the addition of isopropyl-beta-D-1-thiogalactopyranoside (IPTG) to a final concentration of 400 µM once the carbon dioxide evolution rate (CER) reached the threshold of 25 mmol/L/h. Once the initial batch glucose was depleted, measured by a rise in pH, the DSTFS glucose feed solution was fed in an on-demand manner utilizing a series of feed pulses with each pulse being triggered by a pH rise. This experiment was run twice: the first run used a concentration of 0.458 g glucose/g feed while the second run used glucose feed solution with a concentration of 0.48 g glucose/g feed.

Mevalonic acid concentration was determined using a Waters HPLC (Milford, Mass.) equipped with an Aminex HPX-87H Ion Exclusion Column, 300 mm×7.8 mm (Bio-Rad, Hercules, Calif.). The method utilized 5 mM $H_2SO_4$ in an isocratic flow of 0.6 mL/min with a temperature set point of 50° C.

Results

Analysis of the glucose syrup obtained by the DSTFS process is shown in Table 23.

TABLE 23

Concentration of saccharides following production of syrup by DSTFS process.

| | Kgs Corn | Kgs Water | Kgs TOTAL | Kgs Dp1 | Kgs Dp2 | Kgs Dp3+ | Kgs TTLFS | % Dp1 | % Dp2 | % Dp3+ | % TOTAL |
|---|---|---|---|---|---|---|---|---|---|---|---|
| Corn and Water | 40 | 60 | 100 | | | | 31.54 Assumes 100% starch conversion | | | | |
| To Filtration | 32.4 | 48.6 | 81 | | | | 25.55 | | | | |
| End of DSTFS (slurry) | | | 81 | 18.82 | 2.92 | 1.58 | 23.32 | 23.2% | 3.6% | 2.0% | 28.8% |
| End of Filtration | | | 74 | | | | | | | | |
| End of Evaporation | | | 30 | 18.72 | 2.92 | 0.49 | 22.12 | 62.4% | 9.7% | 1.6% | 73.7% |

Figure 2:
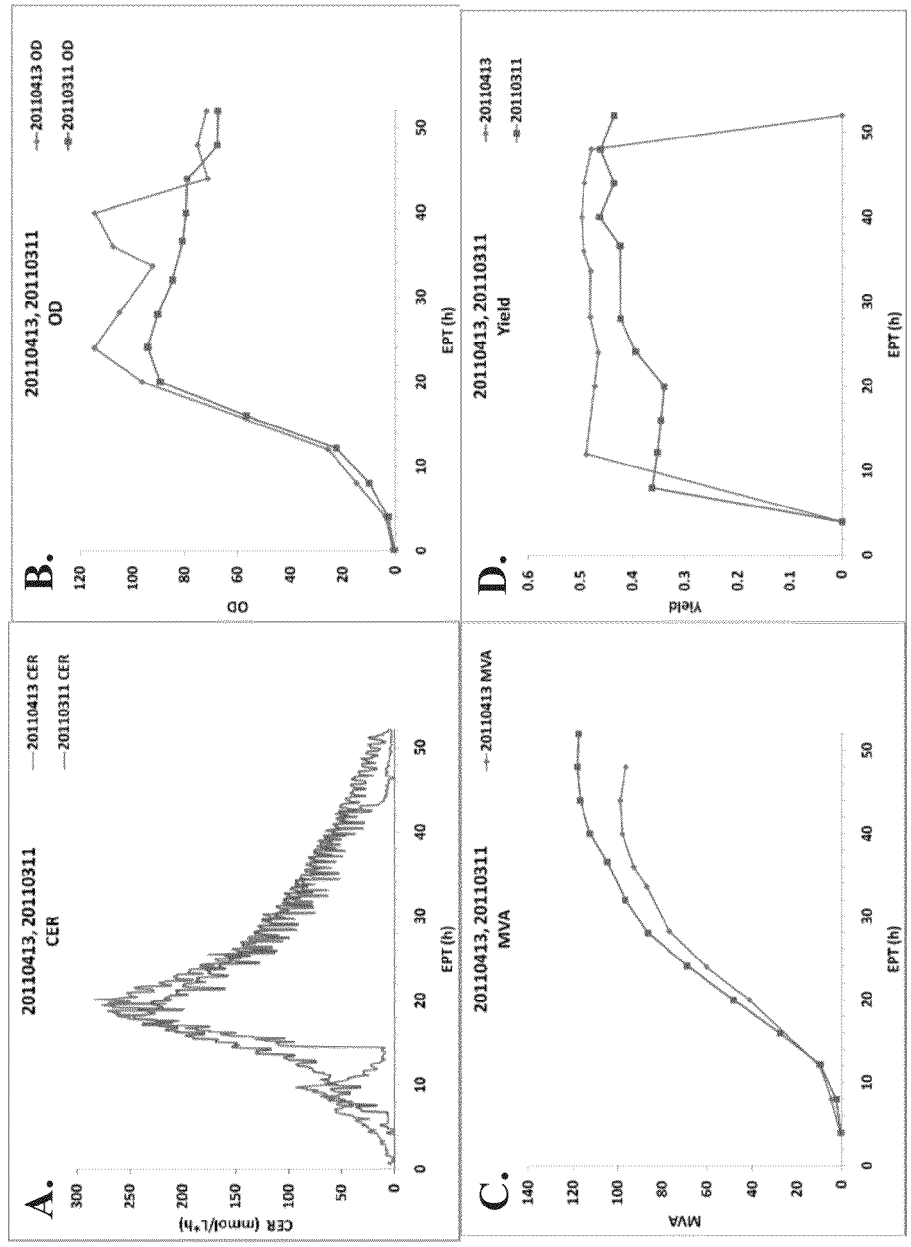
FIG. 2 depicts production of mevalonate by *E. coli* using a feedstock produced by the DSTFS process. (A) Depicts carbon dioxide evolution rate (CER) by the cells during the fermentation. (B) Depicts growth of the cells ($OD_{550}$) during the fermentation. (C) Depicts titer of MVA produced (g/L) during the fermentation. (D) Depicts yield of mevalonate (g MVA/g glucose) produced during the fermentation.
Figure 3:
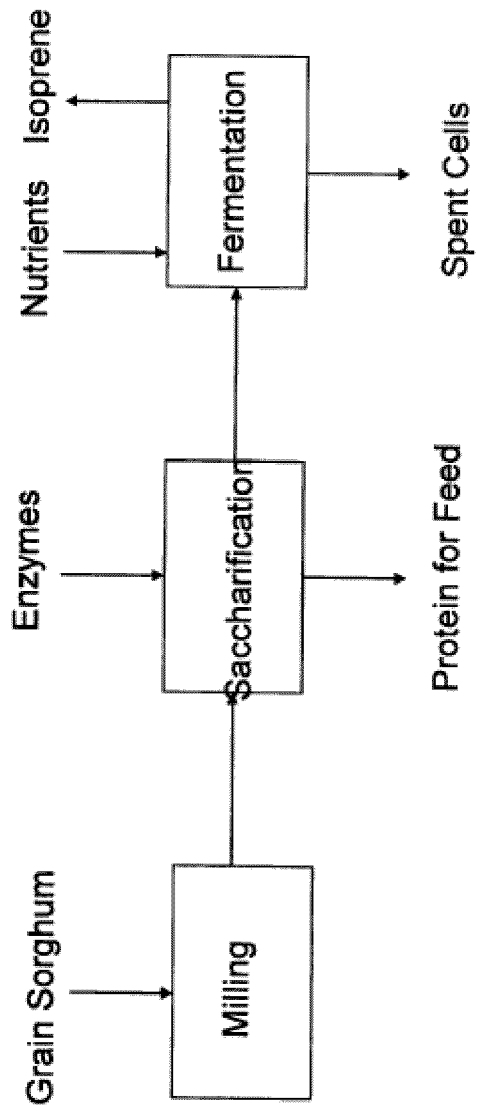
FIG. 3 depicts a schematic illustrating the production of bioisoprene from a grain sorghum feedstock.

A maximum titer of 99.0 g/L of MVA and a maximum yield of 0.475 g MVA/g glucose was produced (FIG. 2).

HPLC analysis of the syrup produced by the DSTFS process indicated that the feedstock contained 82 g/L DP2 saccharides. After completion of fermentation, the remaining fermentation broth was analyzed by HPLC per the methods described above to determine the saccharide profile of the sugars remaining in the broth. The results indicated that approximately 27 g/L DP2 saccharides remained in the broth at the end of the fermentation run—this amount was comparable to what would have accumulated in the fermentation broth for the amount of feed utilized.

Therefore, the results of this experiment suggest that the fermentable sugar feedstocks produced by the DSTFS process can be used by microbes to produce mevalonate, an important intermediate for the production of isoprene, isoprenoid precursor molecules, and/or isoprenoids. However, analysis of the fermentation broth subsequent to completion of the run suggests that the microbes were able to consume little, if any, of the DP2 sugars present in the feedstock.

Example 25

Construction of Isoprene-Producing Strains

A lower mevalonate pathway can be introduced into a mevalonate-producing host cell (see Table 22, supra) by the methods described in U.S. Patent Application Publication No.: 2010/019677 (see Example 8), the disclosure of which is incorporated by reference herein in its entirety. Additionally, these cells are co-electroporated with a variation of plasmid pDW34 (See U.S. Patent Application Publication No: 2010/ 0196977; FIG. 2). The plasmids, which are variants of pDW34, contain an isoprene synthase variant, which is improved for activity. Colonies can be selected on LB+spectinomycin 50 ug/mL+carbenicillin 50 µg/mL.

Example 26

Conversion of DSTFS Feedstock into Isoprene

This example uses glucose syrup obtained by the DSTFS process for the microbial production of isoprene. Preparation of the glucose syrup involves a step for deactivating endogenous DP2 saccharide-producing enzyme activity via exposure of the grain to low pH.

Materials and Methods

Fermentation is performed in a fed-batch culture in a 15-L bioreactor using the transformed isoprene-producing cell lines described in Example 22. Cells are grown and isoprene analyzed using the following methods.

TM3 Media Recipe (Per Liter Fermentation Media):

$K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components are added together and dissolved in $diH_2O$. The pH is adjusted to 6.8 with ammonium hydroxide (30%) and brought to volume. Media is filter-sterilized with a 0.22 micron filter. Glucose 10.0 g, produced by each of the DSTFS process described below, and antibiotics are added after sterilization and pH adjustment.

1000× Trace Metal Solution (Per Liter Fermentation Media):

Citric Acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in $diH_2O$. The pH is adjusted to 3.0 with HCl/NaOH, and then the solution is brought to volume and filter-sterilized with a 0.22 micron filter.

Production of DSTFS Syrup:

Grind corn (40 kg) is mixed into 60 kg water to form a slurry. This solution is mixed for 1 hr at room temperature (RT) with agitation. The slurry can then be split into 2 groups: one can be maintained at pH 5.5 and the other adjusted to pH 3.0 with HCl, followed by incubation at 60° C. for 1 hour in a shaking incubator. The slurry without pH adjustment is incubated at 60° C. in a shaking incubator, while the slurry at pH 3.0 is pH-adjusted with NaOH back to pH 5.5 to continue the incubation. To both slurries are added 13.7 mg of SPEZYME® RSL (Genencor Intl., Palo Alto, Calif.) and 880 µg of TrGA enzyme. The solution is allowed to incubate at RT for 30 min. The temperature can then be sequentially ramped to 60° C. over a 30 min timeframe and is allowed to incubate for 48 hr. The mixtures' pH is monitored and maintained at 5.3-5.5. Syrup separation can be achieved via addition of 2% Dicalite 476 into the slurry and filtration through a K900 pad under 10 psi of pressure. Syrup evaporation can be accomplished via a heat ramp to 90° C. The DP2 content of the syrups produced by both slurries is assessed by HPLC as described above.

Production of DSTFS Syrup:

Grind corn (40 kg) is mixed into 60 kg water to form a slurry. This solution is mixed for 1 hr at room temperature (RT) with agitation. The slurry can then be split into 2 groups: one can be maintained at pH 5.5 and the other adjusted to pH 3.0 with HCl, followed by incubation at 60° C. for 1 hour in a shaking incubator. The slurry without pH adjustment is incubated at 60° C. in a shaking incubator, while the slurry at pH 3.0 is pH-adjusted with NaOH back to pH 5.5 to continue the incubation. To both slurries are added 13.7 mg of SPEZYME® RSL (Genencor Intl., Palo Alto, Calif.) and 880 μg of TrGA enzyme. The solution is allowed to incubate at RT for 30 min. The temperature can then be sequentially ramped to 60° C. over a 30 min timeframe and is allowed to incubate for 48 hr. The mixtures' pH is monitored and maintained at 5.3-5.5. Syrup separation can be achieved via addition of 2% Dicalite 476 into the slurry and filtration through a K900 pad under 10 psi of pressure. Syrup evaporation can be accomplished via a heat ramp to 90° C. The DP2 content of the syrups produced by both slurries is assessed by HPLC as described above.

Cells are grown overnight in Luria-Bertani broth+antibiotics. The day after, they are diluted to an OD600 of 0.05 in 20 mL TM3 medium containing 50 ug/ml of spectinomycin and 50 ug/mL carbenicillin (in a 250-mL baffled Erlenmeyer flask), and incubated at 34° C. and 200 rpm. After 2 h of growth, OD600 is measured and 200 uM IPTG is added. Samples are taken regularly during the course of the fermentation. At each timepoint, $OD_{600}$ is measured. Also, offgas analysis of isoprene is performed using a gas chromatograph-mass spectrometer (GC-MS) (Agilent) headspace assay. One hundred microliters of whole broth are placed in a sealed GC vial and incubated at 34° C. and 200 rpm for a fixed time of 30 minutes. Following a heat kill step, consisting of incubation at 70° C. for 5 minutes, the sample is loaded on the GC. The reported specific productivity is the amount of isoprene in μg/L read by the GC divided by the incubation time (30 min) and the measured $OD_{600}$.

Results

The amount of isoprene produced during fermentation runs using feedstocks produced by grain slurries with and without endogenous enzyme activity is assayed in addition to increased specific productivity, yield, CPI and/or titer of isoprene. Additionally, the fermentation broth remaining after completion of fermentation can be analyzed by HPLC to determine the saccharide profile remaining.

Example 27

Construction of Amorphadiene- or Farnesene-Producing Strains

A lower mevalonate pathway can be introduced into a mevalonate-producing host cell (see Table 22, supra) by the methods described in U.S. Patent Application Publication No.: 2010/019677 (see Example 8), the disclosure of which is incorporated by reference herein in its entirety. Farnesyl diphosphate synthase (ispA) is overexpressed, either by altering the promoter and/or rbs on the chromosome, or by expressing it from a plasmid by co-electroporating. The plasmids, which are variants of pDW34 contain the farnesene synthase codon optimized for *E. coli* or amorphadiene synthase codon optimized for *E. coli*, instead of isoprene synthase. Colonies are selected on LB+spectinomycin 50 ug/mL+carbenicillin 50 ug/mL.

Example 28

Conversion of DSTFS Feedstock into Amorphadiene or Farnesene

This example uses glucose syrup obtained by the DSTFS process for the microbial production of the isoprenoids amorphadiene and farnesene. Preparation of the glucose syrup involves a step for deactivating endogenous DP2 saccharide-producing enzyme activity via exposure of the grain to low pH.

Isoprenoids are compounds derived from the isoprenoid precursor molecules IPP and DMAPP. Over 29,000 isoprenoid compounds have been identified and new isoprenoids are being discovered each year. Isoprenoids can be isolated from natural products, such as microorganisms and species of plants that use isoprenoid precursor molecules as a basic building block to form the relatively complex structures of isoprenoids.

Materials and Methods

TM3 Media Recipe (Per Liter Fermentation Media):

$K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components are added together and dissolved in $diH_2O$. The pH is adjusted to 6.8 with ammonium hydroxide (30%) and brought to volume. Media is then filter-sterilized with a 0.22 micron filter. Glucose 10.0 g, produced by each of the DSTFS process described below, and antibiotics are added after sterilization and pH adjustment.

1000× Trace Metal Solution (Per Liter Fermentation Media):

Citric Acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in $diH_2O$. The pH is adjusted to 3.0 with HCl/NaOH, and then the solution is brought to volume and filter-sterilized with a 0.22 micron filter.

Production of DSTFS Syrup:

Grind corn (40 kg) is mixed into 60 kg water to form a slurry. This solution is mixed for 1 hr at room temperature (RT) with agitation. The slurry can then be split into 2 groups: one can be maintained at pH 5.5 and the other adjusted to pH 3.0 with HCl, followed by incubation at 60° C. for 1 hour in a shaking incubator. The slurry without pH adjustment is incubated at 60° C. in a shaking incubator, while the slurry at pH 3.0 is pH-adjusted with NaOH back to pH 5.5 to continue the incubation. To both slurries are added 13.7 mg of SPEZYME® RSL (Genencor Intl., Palo Alto, Calif.) and 880 μg of TrGA enzyme. The solution is allowed to incubate at RT for 30 min. The temperature can then be sequentially ramped to 60° C. over a 30 min timeframe and is allowed to incubate for 48 hr. The mixtures' pH is monitored and maintained at 5.3-5.5. Syrup separation can be achieved via addition of 2% Dicalite 476 into the slurry and filtration through a K900 pad under 10 psi of pressure. Syrup evaporation can be accomplished via a heat ramp to 90° C. The DP2 content of the syrups produced by both slurries is assessed by HPLC as described above Cells are grown overnight in Luria-Bertani broth+antibiotics. The day after, they are diluted to an OD600 of 0.05 in 20 mL TM3 medium containing 50 ug/ml of spectinomycin and 50 ug/mL carbenicillin (in a 250-mL baffled Erlenmeyer flask), and incubated at 34° C. and 200 rpm. Prior to inoculation, an overlay of 20% (v/v) dodecane (Sigma-Aldrich) is added to each culture flask to trap the volatile sesquiterpene product as described previously (Newman et. al., 2006).

After 2 h of growth, $OD_{600}$ is measured and 0.05-0.40 mM isopropyl β-d-1-thiogalactopyranoside (IPTG) is added. Samples are taken regularly during the course of the fermentation. At each timepoint, $OD_{600}$ is measured. Also, amorphadiene or farnesene concentration in the organic layer is assayed by diluting the dodecane overlay into ethyl acetate. Dodecane/ethyl acetate extracts are analyzed by GC-MS methods as previously described (Martin et. al., Nat. Biotechnol. 2003, 21:96-802) by monitoring the molecular ion (204 m/z) and the 189 m/z fragment ion for amorphadiene or the molecular ion (204 m/z) for farnesene. Amorphadiene or farnesene samples of known concentration are injected to produce standard curves for amorphadiene or farnesene, respectively. The amount of amorphadiene or farnesene in samples is calculated using the amorphadiene or farnesene standard curves, respectively.

Results

The amount of amorphadiene and farnesene produced during fermentation runs using feedstocks produced by grain slurries with and without endogenous enzyme activity is assayed in addition to increased specific productivity, yield, CPI and/or titer. Additionally, the fermentation broth remaining after completion of fermentation can be analyzed by HPLC to determine the saccharide profile remaining.

REFERENCES

Newman, J. D., Marshal, J. L., Chang, M. C. Y., Nowroozi, F., Paradise, E. M., Pitera, D. J., Newman, K. L., Keasling, J. D., 2006. High-level production of amorpha-4,11-diene in a two-phase partitioning bioreactor of metabolically engineered E. coli. Biotechnol. Bioeng. 95:684-691.

Martin, V. J., Pitera, D. J., Withers, S. T., Newman, J. D., Keasling, J. D., 2003. Engineering a mevalonate pathway in E. coli for production of terpenoids. Nat. Biotechnol. 21:796-802.

Example 29

Effects of Phytase Addition to Corn in a Granular Starch Hydrolysis (GSH) Process This example was conducted to determine if phytase addition to corn in a granular starch hydrolysis (GSH) process with alpha amylase and gluco-amylase will increase starch solubilization.

In a GSH process, the goals are to have ideally 100% solubilization of starch and produce >95% glucose. Generally, phytase may be added to the liquefaction process to hydrolyze phytic acid. When phytic acid is hydrolyzed, alpha amylase may work better and/or there may be more starch that becomes available for enzymes. In addition, phytic acid decreases alpha amylase activity at high temperature by chelating calcium, sodium, and other ions. With the natural amount of phytic acid present in corn, it is thought that by hydrolyzing phytic acid with the addition of phytase in a GSH process, the solubilization may increase.

Materials and Methods

The materials for this example were: (1) 32% ds ground corn; (2) 32% ds corn flour slurry; (3) SPEZYME Xtra enzyme (Sticker #2010-0556 and activity 13,249 AAUs/g); (4) BP111 enzyme (Sticker #2009-0005 and activity 63,480 FTUs/g); (5) HGA enzyme (Sticker #2009-1615 and activity 440 GAUs/g); and (6) 25% v/v $NH_4OH$, 6N HCl.

Whole ground corn of 500 g at 32% ds was made with DI water. The slurry was mixed and the pH was adjusted to 5.4 using 25% v/v ammonium hydroxide. Then, 200 grams of the slurry were poured into 2 separate 250 mL flasks. The two runs were dosed with 1) 10 AAUs Xtra and 0.2 GAUs HGA, and 2) 10 AAUs Xtra+10 FTUs BP111+0.2 GAUs HGA. The samples were placed in shakers at 60° C. and 200 rpm for 48 hours. All samples were run in duplicate, and an additional run was completed with 17 AAUs Xtra+0.2 GAUs HGA to determine if a high amount of alpha amylase would achieve the same solubilization (but at faster rate) as a run with a lower amount of alpha amylase.

Samples were taken at 3, 20, 26, and 48 hours for saccharide distribution. A sample was measured into a 2.0 mL centrifuge tube and centrifuged at 13.2 k rpm for approximately 4 minutes. After centrifugation, the refractive index of the supernatant was determined at 30° C. The remaining supernatant was filtered into a separate centrifuge tube through a 3 mL syringe with a 0.45 μm GHP membrane and boiled for 10 minutes to terminate the alpha amylase activity. The boiled sample was prepared for HPLC analysis, where 0.5 mL of filtrate was mixed with 4.5 mL of RO water and placed into HPLC vials.

Samples were taken for complete solubility testing any time after 24 hours from the start of the experiment. This was done by adding 1 drop of SPEZYME FRED into a 2.0 mL centrifuge tube and filling the rest of the tube with sample. The sample was then boiled for 10 minutes and the refractive index was determined at 30° C. The total dry solids are determined by this refractive index. Solubility was determined by taking the supernatant % ds divided by the total % ds and multiplied by 100.

Results and Discussion

Figure 4:
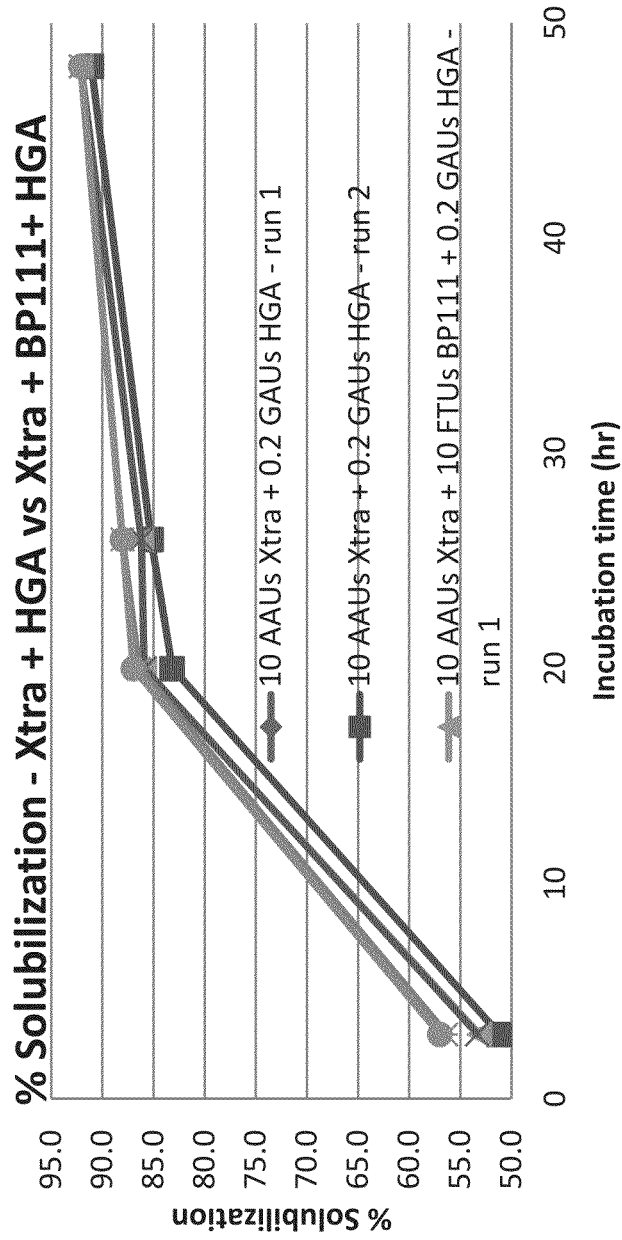
FIG. 4 depicts the percent of starch solubilization versus incubation time for a representative experiment illustrating the effect of phytase added to corn in a granular starch hydrolysis process.

FIGS. 4 and 5 show the % solubilization of the three different runs at 60° C. FIG. 4 shows the % solubilization over 48 hours for the GSH process. Table 24 summarizes the % DP1 and solubilization results for the GSH process.

As can be seen from FIG. 5, the run with 17 AAUs Xtra+0.2 GAUs HGA and the run with 10 AAUs Xtra+10 FTUs BP111+0.2 GAUs HGA reached the same percent solubilization of 92.1 at 48 hours. This was higher than 10 AAUs Xtra+0.2 GAUs HGA run by 1%.

Results on the increased solubilization with phytase are not conclusive since there could be two reasons for the higher solubility: 1) alpha amylase works better when phytic acid is hydrolyzed, or 2) more starch becomes available for enzymes to work on from breaking the phytic acid and starch complex. This experiment should be repeated with a GA only GSH process to remove alpha-amylase as a dependent variable.

TABLE 24

The % DP1 and solubilization results for the GSH process

| Name | hr | % DP1 | % Solubilization |
|---|---|---|---|
| 10 AAUs Xtra + 0.2 GAUs HGA - run 2 | 3 | 63.387 | 51.2 |
| | 20 | 83.664 | 83.2 |
| | 26 | 85.324 | 85.2 |
| | 48 | 86.214 | 91.1 |

TABLE 24-continued

The % DP1 and solubilization results for the GSH process

| Name | hr | % DP1 | % Solubilization |
|---|---|---|---|
| 10 AAUs Xtra + 10 FTUs BP111 + 0.2 GAUs HGA - run 2 | 3 | 61.458 | 53.3 |
| | 20 | 83.412 | 85.9 |
| | 26 | 84.56 | 86.2 |
| | 48 | 85.85 | 92.1 |
| 17 AAUs Xtra + 0.2 GAUs HGA - run 2 | 3 | 60.478 | 57.0 |
| | 20 | 82.387 | 87.0 |
| | 26 | 83.064 | 88.0 |
| | 48 | 85.82 | 92.1 |

Example 30

Effects of Phytase Addition in a Granular Starch Hydrolysis (GSH) Process

This example was conducted in order to determine if phytase addition in a granular starch hydrolysis process will increase the solubilization of starch.

In a GSH process, the goals are to have as close to 100% solubilization of starch and produce >95% glucose. Generally, phytase may be added to the liquefaction process to hydrolyze phytic acid. When phytic acid is hydrolyzed, the alpha amylase enzyme may work better and/or there may be more starch that becomes available for enzymes. In addition, phytic acid decreases alpha amylase activity at high temperature by chelating calcium, sodium, and other ions.

A model system was prepared with starch and added phytic acid as substrate for GSH. With an addition of phytic acid to starch in this example, it was hypothesized that hydrolyzing phytic acid with addition of phytase in a GSH process may increase the solubilization. One experiment was performed with alpha amylase and gluco-amylase while a second experiment was performed with only gluco-amylase to remove alpha-amylase as the dependent factor.

Materials and Methods

The materials for this example were: (1) Gel starch (89.15% ds); (2) Phytic acid sodium salt hydrate; (3) SPEZYME Xtra enzyme sticker (Sticker #2010-0556 and activity 13,249 AAUs/g); (4) BP111 enzyme (Sticker #2009-0005 and activity 63,480 FTUs/g); (5) HGA enzyme (Sticker #2009-1615 and activity 440 GAUs/g); and (6) 25% v/v $NH_4OH$, 6N HCl.

GSH Process Using Alpha Amylase and Gluco-Amylase

Corn has around 1% phytic acid on a dry basis. A model system with starch+1% phytic acid was tested for effect on solubility. The main objective was to determine if increased solubility comes from enhanced alpha amylase activity or from breaking the phytic acid and starch complex. To test this, a GSH process with only gluco-amylase was performed where alpha amylase was not added to the starch slurry.

Raw starch was made up to 400 grams with DI water at 32% ds. Then, 1% phytic acid salt on a dry basis was added to starch and incubated overnight on a stir plate at room temperature to allow phytic acid to bind to starch. After 24 hours of mixing, the starch sample was adjusted to pH 5.4 with 25% v/v ammonium hydroxide. Then, 100 grams of the sample were poured into 3 separate 100 mL bottles, with extra starch left over. Each 100 gram sample was dosed separately with: 1) 10 AAUs SPEZYME Xtra+0.2 GAUs HGA; 2) 10 AAUs Xtra+10 FTUs BP111+0.2 GAUs HGA; and 3) 17 AAUs Xtra+0.2 GAUs HGA. The samples were placed in 60° C. water bath and stirred for 48 hours.

Samples were taken at 2, 18, 24, and 48 hours for saccharide distribution. A sample was measured into a 2.0 mL centrifuge tube and centrifuged at 13.2 k rpm for approximately 4 minutes. After centrifugation, the refractive index of the supernatant was determined at 30° C. The remaining supernatant was filtered into a separate centrifuge tube through a 3 mL syringe with a 0.45 μm GHP membrane and then boiled for 10 minutes to terminate the amylase activity. The boiled sample was prepared for HPLC analysis, where 0.5 mL of filtrate was mixed with 4.5 mL of RO water and placed into HPLC vials.

Samples were taken for complete solubility testing any time after 24 hours from the start. This was done by adding 1 drop of SPEZYME FRED into a 2.0 mL centrifuge tube and filling the rest of the tube with sample. It was then boiled for 10 minutes and the refractive index was determined at 30° C. The total dry solids are determined by this refractive index. Solubility was determined by taking the supernatant % ds divided by the total % ds and multiplied by 100.

GSH Process Using Only Gluco-Amylase

The objective of this example was to study the effect of additional 5% phytic acid on starch solubility compared to a GA only GSH. Then it was tested if the solubility would increase if phytase is also added with phytic acid.

Starch slurries were prepared with and without phytic acid. A 200 g, 32% ds starch slurry was made up and mixed overnight on stir plate with 5% phytic acid. Another set of starch slurries were prepared at 32% ds without phytic acid. All of the starch slurries were adjusted to ph 5.4 with 25% v/v ammonium hydroxide.

The starch slurry with 5% phytic acid was dosed with and without phytase: 1) 1 GAU HGA, and 2) 1 GAU HGA+10 FTUs BP111. The starch slurry without any phytic acid was dosed with 1 GAU HGA only. The samples were then placed in 60° C. water bath and stirred for 48 hours.

Samples were taken at 4, 25, 30, and 48 hours for percent solubilization. A sample was measured into a 2.0 mL centrifuge tube and centrifuged at 13.2 k rpm for approximately 4 minutes. After centrifugation, the refractive index of the supernatant was determined at 30° C. Samples were also taken for complete solubility testing any time after 24 hours from the start of the experiment. This was done by adding 1 drop of SPEZYME FRED into a 2.0 mL centrifuge tube and filling the rest of the tube with sample. It was then boiled for 10 minutes and the refractive index was determined at 30° C. The total dry solids are determined by this refractive index. Solubility was determined by taking the supernatant % ds divided by the total % ds and multiplied by 100.

Results and Discussion

GSH Process with Alpha Amylase and Gluco-Amylase

Figure 6:
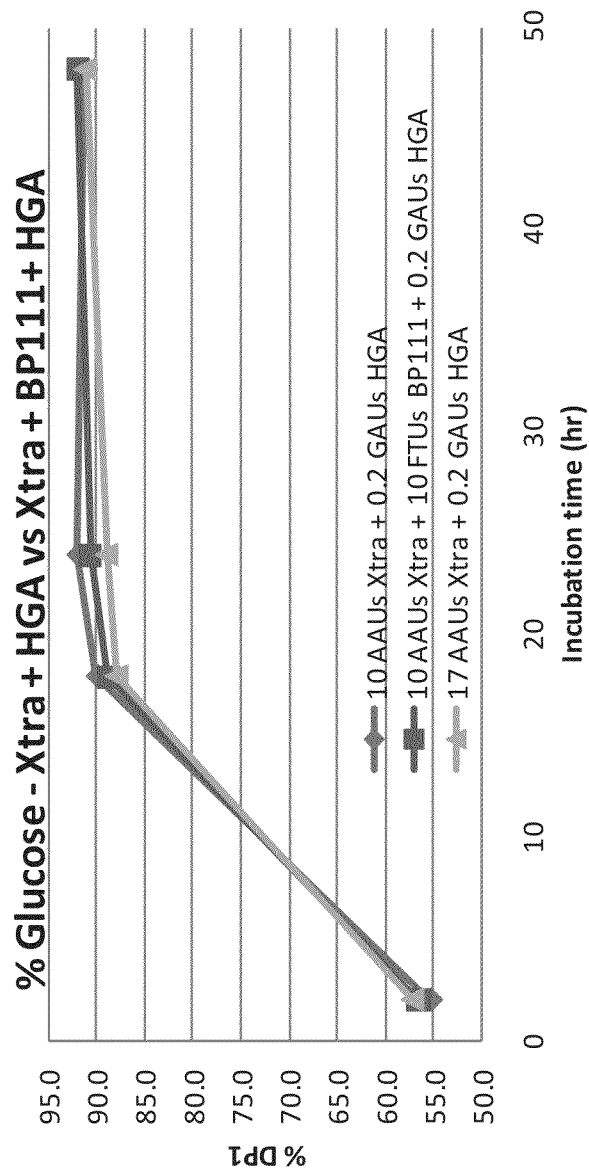
FIG. 6 depicts the percent of glucose (DP1) solubilization versus incubation time for a representative experiment illustrating the effect of phytase with alpha amylase and glucoamylase in a granular starch hydrolysis process.
Figure 7:
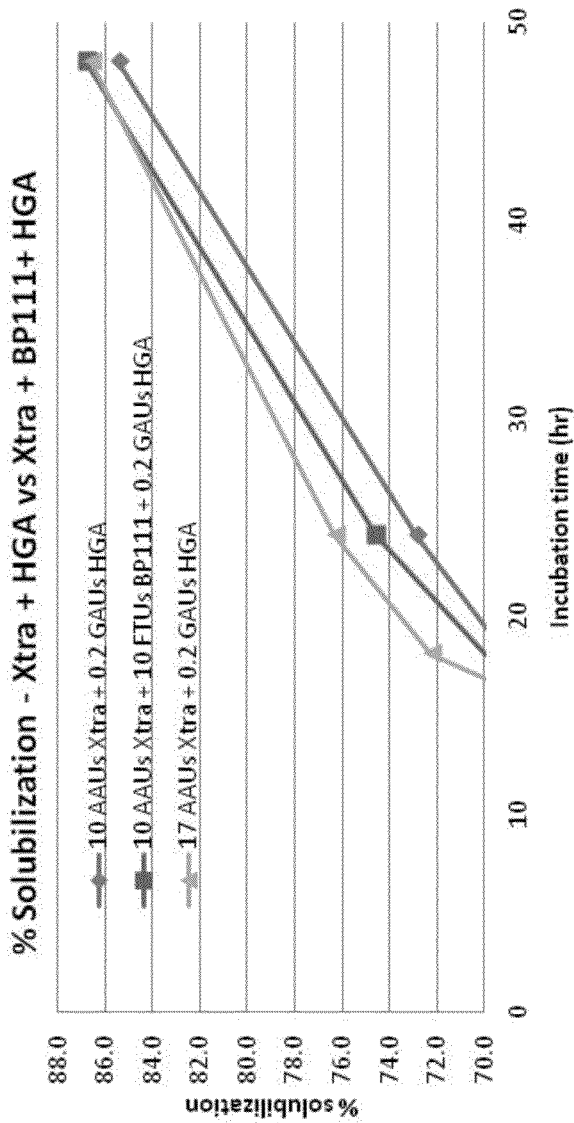
FIG. 7 depicts a zoomed-in view of FIG. 6.

FIGS. 6 and 7 show the % solubilization of the three different runs at 60° C. As can be seen from FIG. 7, the run with 17 AAUs Xtra+0.2 GAUs HGA and the run with 10 AAUs Xtra+10 FTUs BP111+0.2 GAUs HGA reached approximately the same percent solubilization of 86.6-86.8 at 48 hours. This was higher than the 10 AAUs Xtra+0.2 GAUs HGA run by 1.2-1.4%. The glucose levels for all three runs went to 91.2-92.0%. Table 25 summarizes the % solubilization and DP1 results.

Results on the increased solubilization with phytase are not conclusive since there may be two reasons for the higher solubility: 1) alpha amylase works better when phytic acid is hydrolyzed, or 2) more starch becomes available for enzymes to work on from breaking the phytic acid and starch complex. Accordingly, the next part of the example was performed to determine the reasons for increased solubilization with phytase.

TABLE 25

The % DP1 and solubilization for GSH process with alpha amylase and gluco-amylase

| Name | hr | % DP1 | % Solubilization |
|---|---|---|---|
| 10 AAUs Xtra + 0.2 GAUs HGA | 2 | 55.19 | 40.68 |
|  | 18 | 89.99 | 69.09 |
|  | 24 | 92.01 | 72.87 |
|  | 48 | 91.21 | 85.43 |
| 10 AAUs Xtra + 10 FTUs BP111 + 0.2 GAUs HGA | 2 | 56.50 | 39.18 |
|  | 18 | 88.82 | 69.92 |
|  | 24 | 90.68 | 74.57 |
|  | 48 | 91.96 | 86.80 |

TABLE 25-continued

The % DP1 and solubilization for GSH process with alpha amylase and gluco-amylase

| Name | hr | % DP1 | % Solubilization |
|---|---|---|---|
| 17 AAUs Xtra + 0.2 GAUs HGA | 2 | 57.08 | 42.20 |
|  | 18 | 87.95 | 72.23 |
|  | 24 | 89.00 | 76.30 |
|  | 48 | 91.19 | 86.57 |

GSH Process with Gluco-Amylase

Figure 8:
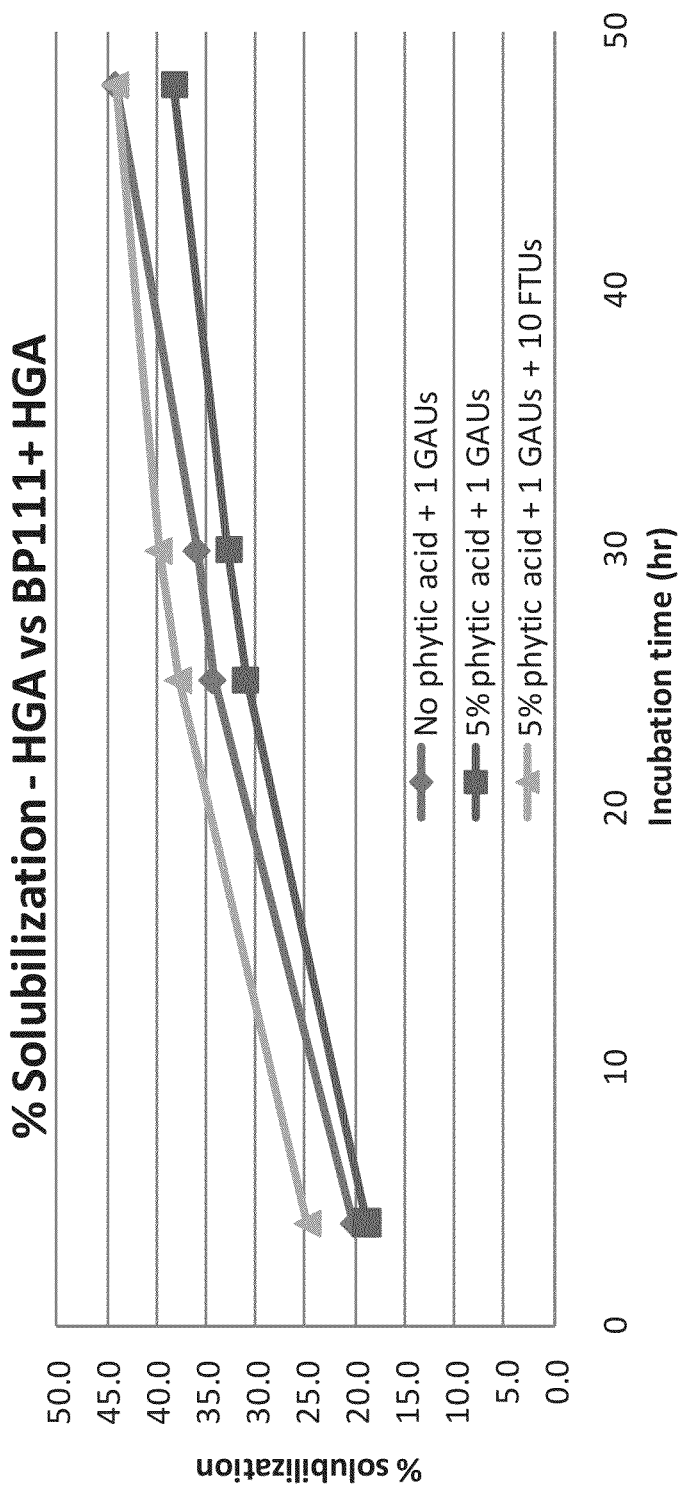
FIG. 8 depicts the percent of starch solubilization versus incubation time for a representative experiment illustrating the effect of phytase with gluco-amylase in a granular starch hydrolysis process.
Figure 9:
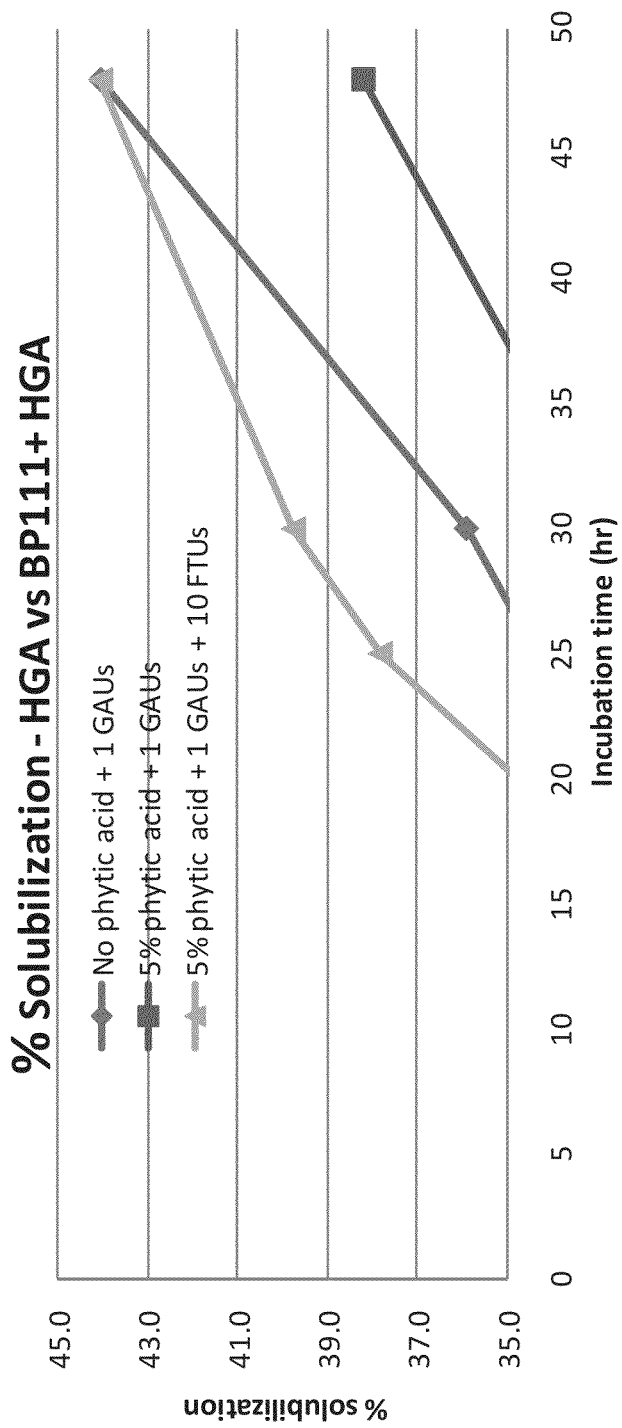
FIG. 9 depicts a zoomed-in view of FIG. 8.

FIGS. 8 and 9 show the % solubilization of the three different runs at 60° C. As shown in the two graphs, the run with no phytic acid+1 GAUs HGA and the run with 5% phytic acid+1 GAUs HGA+10 FTUs BP111 both reached same percent solubilization at the end of 48 hours with 44.1%. This was 5.9% higher solubilization compared to the run with 5% phytic acid+1 GAUs HGA (no phytase addition). Higher solubilization achieved with phytase addition allowed for more starch to become available by hydrolyzing phytic acid that is bound to starch.

What is claimed is:

1. A method for the production of isoprene by recombinant microbial host cells in culture, wherein the host cells comprise one or more heterologous nucleic acids encoding an isoprene synthase polypeptide and one or more mevalonate (MVA) pathway polypeptides, the method comprising:
   a. inactivating endogenous enzyme activity in a whole or fractionated grain, wherein the endogenous enzyme activity is capable of producing kojibiose or nigerose, wherein said inactivation comprises temporarily lowering the pH of an aqueous slurry of the whole or fractionated grain to about pH 1 to 4;
   b. treating the whole or fractionated grain of step (a) with a starch solubilizing alpha amylase and a glucoamylase, wherein the treatment is at a temperature at or below the initial gelatinization temperature of the starch in the grain, wherein the pH is adjusted to about pH 4.0 to 6.5, wherein the concentration of the alpha amylase is between about 5 to 25 AAU/gds, and wherein the treatment produces a fermentable sugar feedstock, wherein the fermentable sugar feedstock comprises a reduced concentration of DP-2 saccharides in comparison to fermentable sugar feedstocks that are not made by the inactivation of step (a) and the treatment of step (b), wherein said reduced concentration of DP-2 saccharides comprises reduced concentration of kojibiose or nigerose;
   c. culturing the recombinant host cells in culture media comprising the fermentable sugar feedstock; and
   d. producing isoprene.

2. The method of claim 1, wherein the treatment of step (b) is at a temperature of about 0 to about 30° C. below the initial gelatinization temperature of the starch in the grain.

3. The method of claim 1, wherein the concentration of alpha amylase is about 6 AAU/g ds to about 10 AAU/g ds.

4. The method of claim 1, wherein the isoprene synthase polypeptide is a plant isoprene synthase polypeptide.

5. The method of claim 4, wherein the plant isoprene synthase polypeptide is a kudzu isoprene synthase polypeptide.

6. The method of claim 1, wherein the isoprene synthase polypeptide is a polypeptide from *Pueraria* or *Populus* or a hybrid of *Populus alba×Populus tremula*.

7. The method of claim 6, wherein the isoprene synthase polypeptide is from *Pueraria montana, Pueraria lobata, Populus tremuloides, Populus alba, Populus nigra*, or *Populus trichocarpa*.

8. The method of claim 1, wherein the recombinant cells further comprise one or more heterologous nucleic acids encoding a 1-Deoxyxylulose-5-phosphate synthase (DXS) polypeptide.

9. The method of claim 1, wherein said one or more heterologous nucleic acids is placed under the control of an inducible promoter or a constitutive promoter.

10. The method of claim 1, wherein said one or more heterologous nucleic acids is cloned into a multicopy plasmid.

11. The method of claim 1, wherein said one or more heterologous nucleic acids is integrated into a chromosome of the cells.

12. The method of claim 1, wherein the host cells are bacterial, algal, fungal or yeast cells.

13. The method of claim 12, wherein the bacterial cells are gram-positive bacterial cells or gram-negative bacterial cells.

14. The method of claim 13, wherein the bacterial cells are selected from the group consisting of *Escherichia coli, Pantoea citrea, Bacillus (B.) subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, Strepto-*

*myces* (*S.*) *albus, S. lividans, S. coelicolor, S. griseus, Pseudomonas* (*P.*) sp., and *P. alcaligenes* cells.

15. The method of claim 12, wherein the algal cells are selected from the group consisting of green algae, red algae, glaucophytes, chlorarachniophytes, euglenids, chromista, and dinoflagellates.

16. The method of claim 12, wherein the host cells are fungal cells.

17. The method of claim 16, wherein the fungal cells are filamentous fungi.

18. The method of claim 12, wherein the host cells are yeast cells.

19. The method of claim 18, wherein the yeast cells are selected from the group consisting of *Saccharomyces* sp., *Schizosaccharomyces* sp., *Pichia* sp., and *Candida* sp.

20. The method of claim 19, wherein the yeast cells are *Saccharomyces cerevisiae*.

21. The method of claim 1, wherein the whole or fractionated grain is whole crown corn or corn endosperm.

22. The method of claim 1, wherein endogenous enzyme activity is inactivated in step (a) at a temperature of about 37 to about 80° C.

23. The method of claim 1, wherein greater than about 90% of the starch from the whole or fractionated grain is solubilized.

24. The method of claim 23, wherein the solubilized starch comprises greater than about 90% fermentable sugars.

25. The method of claim 1, further comprising treating the whole or fractionated grain with one or more enzymes selected from the group consisting of: cellulases, hemicellulases, pullulanases, pectinases, phytases, and proteases.

26. The method of claim 1, wherein the alpha amylase is an acid fungal alpha amylase.

27. The method of claim 1, wherein the alpha amylase is derived from a *Bacillus* species.

28. The method of claim 1, wherein the treatment of step (b) is at a temperature of about 55 to about 65° C.

29. The method of claim 1, wherein glucoamylase is at a concentration of about 0.025 GAU/g ds to about 0.075 GAU/g ds.

30. The method of claim 1, wherein glucoamylase is at a concentration of about 0.075 GAU/g ds to about 0.2 GAU/g ds.

31. The method of claim 1, further comprising recovering the isoprene.

32. A method for the production of isoprenoids by recombinant microbial host cells in culture, wherein the host cells comprise one or more heterologous nucleic acids encoding one or more mevalonate (MVA) pathway polypeptides and one or more polyprenyl pyrophosphate synthase polypeptides, the method comprising:
  a. inactivating endogenous enzyme activity in a whole or fractionated grain, wherein the endogenous enzyme activity is capable of producing kojibiose or nigerose, wherein said inactivation comprises temporarily lowering the pH of an aqueous slurry of the whole or fractionated grain to about pH 1 to 4;
  b. treating the whole or fractionated grain of step (a) with a starch solubilizing alpha amylase and a glucoamylase, wherein the treatment is at a temperature below the gelatinization temperature of the starch in the grain, wherein the pH is adjusted to about pH 4.0 to 6.5, wherein the concentration of the alpha amylase is between about 5 to 25 AAU/gds, and wherein the treatment produces a fermentable sugar feedstock, wherein the fermentable sugar feedstock comprises a reduced concentration of DP-2 saccharides in comparison to fermentable sugar feedstocks that are not made by the inactivation of step (a) and the treatment of step (b), wherein said reduced concentration of DP-2 saccharides comprises reduced concentration of kojibiose or nigerose;
  c. culturing the recombinant host cells in culture media comprising the fermentable sugar feedstock; and
  d. producing isoprenoids.

33. The method of claim 32, further comprising recovering the isoprenoids.

34. The method of claim 32 or 33, wherein the isoprenoid is selected from group consisting of monoterpenes, diterpenes, triterpenes, tetraterpenes, sequiterpene, polyterpene, abietadiene, amorphadiene, carene, α-famesene, β-farnesene, farnesol, geraniol, geranylgeraniol, linalool, limonene, myrcene, nerolidol, ocimene, patchoulol, β-pinene, sabinene, γ-terpinene, terpindene and valencene.

35. The method of claim 32, wherein the treatment in step (b) is at a temperature of about 0 to about 30° C. below the initial gelatinization temperature of the starch in the grain.

36. The method of claim 32, wherein the concentration of alpha amylase is about 6 AAU/g ds to about 10 AAU/g ds.

37. The method of claim 32, wherein the host cells are bacterial, algal, fungal or yeast cells.

38. A method for the production of mevalonate by recombinant microbial host cells in culture, wherein the host cells comprise one or more heterologous nucleic acids encoding one or more mevalonate (MVA) pathway polypeptides, the method comprising:
  a. inactivating endogenous enzyme activity in a whole or fractionated grain, wherein the endogenous enzyme activity is capable of producing kojibiose or nigerose, wherein said inactivation comprises temporarily lowering the pH of an aqueous slurry of the whole or fractionated grain to about pH 1 to 4;
  b. treating the whole or fractionated grain of step (a) with a starch solubilizing alpha amylase and a glucoamylase, wherein the treatment is at a temperature below the gelatinization temperature of the starch in the grain, wherein the pH is adjusted to about pH 4.0 to 6.5, wherein the concentration of the alpha amylase is between about 5 to 25 AAU/gds, and wherein the treatment produces a fermentable sugar feedstock, wherein the fermentable sugar feedstock comprises a reduced concentration of DP-2 saccharides in comparison to fermentable sugar feedstocks that are not made by the inactivation of step (a) and the treatment of step (b), wherein said reduced concentration of DP-2 saccharides comprises reduced concentration of kojibiose or nigerose;
  c. culturing the recombinant host cells in culture media comprising the fermentable sugar feedstock; and
  d. producing mevalonate.

39. The method of claim 38, further comprising recovering the mevalonate.

40. The method of claim 38, wherein the treatment in step (b) is at a temperature of about 0 to about 30° C. below the initial gelatinization temperature of the starch in the grain.

41. The method of claim 38, wherein the concentration of alpha amylase is about 6 AAU/g ds to about 10 AAU/g ds.

42. The method of claim 38, wherein the host cells are bacterial, algal, fungal or yeast cells.

43. The method of any one of claims 1, 32, and 38, wherein step b further comprises treating the whole or fractionated grain with phytase.

* * * * *